(12) United States Patent
Miller et al.

(10) Patent No.: US 12,344,872 B2
(45) Date of Patent: *Jul. 1, 2025

(54) ENGINEERED LIGASE VARIANTS

(71) Applicant: Codexis, Inc., Redwood City, CA (US)

(72) Inventors: Mathew G. Miller, San Carlos, CA (US); Jonathan Vroom, South San Francisco, CA (US); Nikki Dellas, Mountain View, CA (US); Donald S. Baskerville, Burlingame, CA (US); Sandy M. Gomes, Redwood City, CA (US); David Elgart, San Mateo, CA (US); Judy Victoria Antonio Viduya, South San Francisco, CA (US)

(73) Assignee: Codexis, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/972,919

(22) Filed: May 7, 2018

(65) Prior Publication Data

US 2018/0320162 A1   Nov. 8, 2018

Related U.S. Application Data

(60) Provisional application No. 62/587,030, filed on Nov. 16, 2017, provisional application No. 62/540,734, filed on Aug. 3, 2017, provisional application No. 62/503,075, filed on May 8, 2017.

(51) Int. Cl.
| | | |
|---|---|---|
| *C12P 19/34* | (2006.01) | |
| *C12N 9/00* | (2006.01) | |
| *C12Q 1/6806* | (2018.01) | |
| *C40B 40/10* | (2006.01) | |

(52) U.S. Cl.
CPC ............... *C12N 9/93* (2013.01); *C12P 19/34* (2013.01); *C12Q 1/6806* (2013.01); *C12Y 605/01001* (2013.01)

(58) Field of Classification Search
CPC .................................. C12N 9/00; C12P 19/34
See application file for complete search history.

(56) References Cited

U.S. PATENT DOCUMENTS

| | | |
|---|---|---|
| 4,582,802 A | 4/1986 | Zimmerman et al. |
| 5,605,793 A | 2/1997 | Stemmer |
| 5,811,238 A | 9/1998 | Stemmer et al. |
| 5,830,721 A | 11/1998 | Stemmer et al. |
| 5,834,252 A | 11/1998 | Stemmer et al. |
| 5,837,458 A | 11/1998 | Minshull et al. |
| 5,928,905 A | 7/1999 | Stemmer et al. |
| 6,096,548 A | 8/2000 | Stemmer |
| 6,117,679 A | 9/2000 | Stemmer |
| 6,132,970 A | 10/2000 | Stemmer |
| 6,165,793 A | 12/2000 | Stemmer |
| 6,180,406 B1 | 1/2001 | Stemmer |
| 6,251,674 B1 | 6/2001 | Tobin et al. |
| 6,265,201 B1 | 7/2001 | Wackett et al. |
| 6,277,638 B1 | 8/2001 | Stemmer |
| 6,287,861 B1 | 9/2001 | Stemmer et al. |
| 6,287,862 B1 | 9/2001 | delCardayre et al. |
| 6,291,242 B1 | 9/2001 | Stemmer |
| 6,297,053 B1 | 10/2001 | Stemmer |
| 6,303,344 B1 | 10/2001 | Patten et al. |
| 6,309,883 B1 | 10/2001 | Minshull et al. |
| 6,319,713 B1 | 11/2001 | Patten et al. |
| 6,319,714 B1 | 11/2001 | Crameri et al. |
| 6,323,030 B1 | 11/2001 | Stemmer |
| 6,326,204 B1 | 12/2001 | delCardayre et al. |
| 6,335,160 B1 | 1/2002 | Patten et al. |
| 6,335,198 B1 | 1/2002 | delCardayre et al. |
| 6,337,186 B1 | 1/2002 | Krebber |
| 6,344,356 B1 | 2/2002 | Stemmer |
| 6,352,859 B1 | 3/2002 | delCardayre et al. |
| 6,355,484 B1 | 3/2002 | Patten et al. |
| 6,358,740 B1 | 3/2002 | Patten et al. |
| 6,358,742 B1 | 3/2002 | Stemmer |
| 6,365,377 B1 | 4/2002 | Patten et al. |
| 6,365,408 B1 | 4/2002 | Stemmer |
| 6,368,861 B1 | 4/2002 | Crameri et al. |
| 6,372,497 B1 | 4/2002 | Stemmer |
| 6,376,246 B1 | 4/2002 | Crameri et al. |
| 6,379,964 B1 | 4/2002 | delCardayre et al. |
| 6,387,702 B1 | 5/2002 | Stemmer |
| 6,391,552 B2 | 5/2002 | Stemmer |
| 6,391,640 B1 | 5/2002 | Minshull et al. |
| 6,395,547 B1 | 5/2002 | Stemmer |

(Continued)

FOREIGN PATENT DOCUMENTS

| | | | |
|---|---|---|---|
| WO | 95/22625 A1 | 8/1995 | |
| WO | 95/33836 A1 | 12/1995 | |

(Continued)

OTHER PUBLICATIONS

Tanabe et al., From Structure-Function Analyses to Protein Engineering for Practical Applications of DNA Ligase, Archaea, 2015, 1-21. (Year: 2015).*
STIC, Sequence Search Results, USPTO, 20200520_1122_us15972919-6.rapbm, The Scientific Technical and Information Center, 2020, 1-18. (Year: 2020).*
Worthington, DNA Ligase, T4, Worthington Enzyme Manuel, 1993, 1-3. Obtained online at http://worthington-biochem.com/DNAT4L/default.html on Dec. 21, 2020. (Year: 1993).*
Stevenson, L., Development of a Novel Selection Strategy to Enable Directed Evolution of DNA Ligase Enzymes, School of Biological Sciences, Cell & Molecular Biology Seminar Series 2014, 1-3. (Year: 2014).*
Wilson et al., Engineered DNA Ligases with Improved Activities In Vitro, Protein Engineering, Design & Selection, 2013, 26(7), 471-478. (Year: 2013).*

(Continued)

*Primary Examiner* — Amy M Bunker
(74) *Attorney, Agent, or Firm* — Eric Grant Lee

(57) ABSTRACT

The present invention provides engineered ligase polypeptides and compositions thereof, as well as polynucleotides encoding the engineered ligase polypeptides. The invention also provides methods for use of the compositions comprising the engineered ligase polypeptides for diagnostic and other purposes.

1 Claim, 6 Drawing Sheets

Specification includes a Sequence Listing.

(56) References Cited

U.S. PATENT DOCUMENTS

| | | |
|---|---|---|
| 6,406,855 B1 | 6/2002 | Patten et al. |
| 6,406,910 B1 | 6/2002 | Patten et al. |
| 6,413,745 B1 | 7/2002 | Patten et al. |
| 6,413,774 B1 | 7/2002 | Stemmer |
| 6,420,175 B1 | 7/2002 | Stemmer |
| 6,423,542 B1 | 7/2002 | Crameri et al. |
| 6,426,224 B1 | 7/2002 | Crameri et al. |
| 6,436,675 B1 | 8/2002 | Welch et al. |
| 6,444,468 B1 | 9/2002 | Stemmer et al. |
| 6,455,253 B1 | 9/2002 | Patten et al. |
| 6,479,652 B1 | 11/2002 | Crameri et al. |
| 6,482,647 B1 | 11/2002 | Stemmer |
| 6,483,011 B1 | 11/2002 | Stemmer et al. |
| 6,484,105 B2 | 11/2002 | Zhang |
| 6,489,146 B2 | 12/2002 | Stemmer et al. |
| 6,500,617 B1 | 12/2002 | Stemmer et al. |
| 6,500,639 B2 | 12/2002 | Subramanian |
| 6,506,602 B1 | 1/2003 | Stemmer |
| 6,506,603 B1 | 1/2003 | Stemmer |
| 6,518,065 B1 | 2/2003 | Stemmer |
| 6,519,065 B1 | 2/2003 | Colbourne et al. |
| 6,521,453 B1 | 2/2003 | Crameri et al. |
| 6,528,311 B1 | 3/2003 | delCardayre et al. |
| 6,537,746 B2 | 3/2003 | Arnold et al. |
| 6,573,098 B1 | 6/2003 | Stemmer |
| 6,576,467 B1 | 6/2003 | Stemmer |
| 6,579,678 B1 | 6/2003 | Patten et al. |
| 6,586,182 B1 | 7/2003 | Patten et al. |
| 6,602,986 B1 | 8/2003 | Stemmer et al. |
| 6,605,430 B1 | 8/2003 | Affholter et al. |
| 6,613,514 B2 | 9/2003 | Patten et al. |
| 6,653,072 B1 | 11/2003 | Patten et al. |
| 6,686,515 B1 | 2/2004 | Lassner et al. |
| 6,703,240 B1 | 3/2004 | Stemmer et al. |
| 6,716,631 B1 | 4/2004 | delCardayre et al. |
| 6,825,001 B2 | 11/2004 | Wackett et al. |
| 6,902,922 B2 | 6/2005 | Ness et al. |
| 6,917,882 B2 | 7/2005 | Selfinov et al. |
| 6,946,296 B2 | 9/2005 | Patten et al. |
| 6,961,664 B2 | 11/2005 | Selfinov et al. |
| 6,995,017 B1 | 2/2006 | Stemmer |
| 7,024,312 B1 | 4/2006 | Selfinov et al. |
| 7,058,515 B1 | 6/2006 | Selfinov et al. |
| 7,105,297 B2 | 9/2006 | Minshull et al. |
| 7,148,054 B2 | 12/2006 | delCardayre et al. |
| 7,220,566 B2 | 5/2007 | Ness et al. |
| 7,288,375 B2 | 10/2007 | Stemmer et al. |
| 7,384,387 B1 | 6/2008 | Raillard et al. |
| 7,421,347 B2 | 9/2008 | Selfinov et al. |
| 7,430,477 B2 | 9/2008 | Selfinov et al. |
| 7,462,469 B2 | 12/2008 | Bass et al. |
| 7,534,564 B2 | 5/2009 | Patten et al. |
| 7,620,500 B2 | 11/2009 | Mundorff et al. |
| 7,620,502 B2 | 11/2009 | Selfinov et al. |
| 7,629,157 B2 | 12/2009 | Davis et al. |
| 7,629,170 B2 | 12/2009 | delCardayre et al. |
| 7,702,464 B1 | 4/2010 | Emig et al. |
| 7,747,391 B2 | 6/2010 | Gustafsson et al. |
| 7,747,393 B2 | 6/2010 | Fox |
| 7,751,986 B2 | 7/2010 | Gustafsson et al. |
| 7,776,598 B2 | 8/2010 | Patten et al. |
| 7,783,428 B2 | 8/2010 | Gustafsson et al. |
| 7,795,030 B2 | 9/2010 | Minshull et al. |
| 7,853,410 B2 | 12/2010 | Selfinov et al. |
| 7,868,138 B2 | 1/2011 | Stemmer et al. |
| 7,873,477 B1 | 1/2011 | Gustafsson et al. |
| 7,873,499 B2 | 1/2011 | Selfinov et al. |
| 7,904,249 B2 | 3/2011 | Selfinov et al. |
| 7,957,912 B2 | 6/2011 | Selfinov et al. |
| 7,981,614 B2 | 7/2011 | Stemmer et al. |
| 8,014,961 B2 | 9/2011 | Bass et al. |
| 8,029,988 B2 | 10/2011 | Crameri et al. |
| 8,048,674 B2 | 11/2011 | Minshull et al. |
| 8,058,001 B2 | 11/2011 | Crameri et al. |
| 8,076,138 B2 | 12/2011 | delCardayre et al. |
| 8,108,150 B2 | 1/2012 | Mundorff et al. |
| 8,170,806 B2 | 5/2012 | Selfinov et al. |
| 8,224,580 B2 | 7/2012 | Mundorff et al. |
| 8,377,681 B2 | 2/2013 | delCardayre et al. |
| 8,383,346 B2 | 2/2013 | Colbeck et al. |
| 8,457,903 B1 | 6/2013 | Emig et al. |
| 8,504,498 B2 | 8/2013 | Fox |
| 8,589,085 B2 | 11/2013 | Selfinov et al. |
| 8,728,725 B2 | 5/2014 | Paul et al. |
| 8,762,066 B2 | 6/2014 | Fox |
| 8,768,871 B2 | 7/2014 | Fox |
| 9,499,811 B2 | 11/2016 | Kucera et al. |
| 9,593,326 B2 | 3/2017 | Clark et al. |
| 10,837,009 B1 | 11/2020 | Ong et al. |
| 2008/0220990 A1 | 9/2008 | Fox |
| 2009/0312196 A1 | 12/2009 | Colbeck et al. |
| 2012/0214208 A1* | 8/2012 | Patrick .................... C12N 9/93 |
| | | 435/91.52 |
| 2014/0187447 A1 | 7/2014 | Kucera et al. |
| 2015/0010525 A1 | 1/2015 | Wells et al. |
| 2015/0133307 A1* | 5/2015 | Zhang .................... G16B 35/00 |
| | | 506/1 |
| 2016/0186164 A1* | 6/2016 | Christians .......... C07K 14/4702 |
| | | 435/91.52 |
| 2016/0244787 A1 | 8/2016 | Chan et al. |
| 2017/0226498 A1* | 8/2017 | Zheng ............. C12Y 605/01002 |
| 2018/0023122 A1* | 1/2018 | Crameri ................. C07H 21/00 |
| | | 435/91.2 |

FOREIGN PATENT DOCUMENTS

| | | |
|---|---|---|
| WO | 96/00787 A1 | 1/1996 |
| WO | 97/0078 A1 | 1/1997 |
| WO | 97/35966 A1 | 10/1997 |
| WO | 98/27230 A1 | 6/1998 |
| WO | 00/42651 A1 | 7/2000 |
| WO | 01/75767 A2 | 10/2001 |
| WO | 2009/152336 A1 | 12/2009 |
| WO | 2010/144103 A1 | 12/2010 |
| WO | 2011/034449 A1 | 3/2011 |
| WO | 2014/145269 A1 | 9/2014 |

OTHER PUBLICATIONS

Suzuki et al., Efficient DNA Ligation by Selective Heating of DNA Ligase with a Radio Frequency Alternating Magnetic Field, Biochemistry and Biophysics Reports, 2016, 8, 360-364. (Year: 2016).*

Madrid et al., T4 DNA Ligase Synthesizes Dinucleoside Polyphosphates; FEBS Letters, 1998, 433, 283-286. (Year: 1998).*

Wang et al., The Phage T4 DNA Ligase In Vivo Improves the Survival-Coupled Bacterial Mutagenesis, Microbial Cell Factories, 2019, 18(107), 1-8. (Year: 2019).*

Wilson, R., Accelerating Drug Development and Manufacturing with Engineered Enzymes, Pharma's Almanac, epub Apr. 1, 2016, 1-8 obtained online at https://www.pharmasalmanac.com/articles/q2-codexis-accelerating-drug-development-and-manufacturing-with-engineered-enzymes on Apr. 6, 2021. (Year: 2016).*

Promega, Cloning Enzymes, Enzyme Resource Guide, 1999, 1-40. (Year: 1999).*

Wilson et al., Engineered DNA ligases with improved activities in vitro, Protein Engineering and Design, 2013, 26(7), 471-478. (Year: 2013).*

Tanabe et al., From Structure-Function Analyses to Protein Engineering for Practical Applications of DNA Ligase, Archaea, 2015, 267570, 1-20. (Year: 2015).*

Kuhn et al., Template-independent ligation of single-stranded DNA by T4 DNA ligase; The FEBS Journal, 2005, 272, 5991-6000. (Year: 2005).*

Altschul, S.F., et al., "Gapped BLAST and PSI-BLAST: a new generation of protein database search programs," Nucleic Acids Res., 25(17):3389-3402 (1997).

Altschul, S., et al., "Basic local alignment search tool," J. Mol. Biol., 215: 403-410 (1990).

Beaucage, S.L., et al., "Deoxynucleoside phosphoamidites—A new class of key intermediates for deoxypolynucleotide synthesis," Tetrahedron Letters, 22(20):1859-62 (1981).

(56) References Cited

OTHER PUBLICATIONS

Black, M.E., et al., "Creation of drug-specific herpes simplex virus type 1 thymidine kinase mutants for gene therapy," Proc Natl Acad Sci USA, 93:3525-3529 (1996).
Botstein, D., et al., "Strategies and applications of in vitro mutagenesis," Science, 229(4719):1193-1201, 1985.
Caldwell, R.C., et al., "Mutagenic PCR," PCR Methods Appl., 3:S136-S140 [1994].
Carter, P., "Site-directed mutagenesis," Biochem. J., 237:1-7 (1986).
Christians, F.C., et al., "Directed evolution of thymidine kinase for AZT phosphorylation using DNA family shuffling," Nat. Biotechnol., 17:259-264 (1999).
Crameri, A., et al., "DNA shuffling of a family of genes from diverse species accelerates directed evolution", Nature, 391:288-291 (1998).
Crameri, A., et al., "Improved green fluorescent protein by molecular evolution using DNA shuffling,"Nat. Biotechnol., 14(3):315-319 (1996).
Crameri, A., et al., "Molecular evolution of an arsenate detoxification pathway by DNA shuffling," Nat. Biotechnol., 15 (5):436-438 (1997).
Dale, S.J., et al., "Oligonucleotide-directed random mutagenesis using the phosphorothioate method," Methods Mol. Biol., 57:369-74 (1996).
De Boer, H.A., et al., "The tac promoter: A functional hybrid derived from the trp and lac promoters," Proc. Natl Acad. Sci. USA, 80: 21-25 (1983).
Guo, Z., et al., "3'-End-Forming Signals of Yeast mRNA, " Mol. Cell. Biol., 15(11):5983-5990 [1995].
Henikoff, S., et al., "Amino acid substitution matrices from protein blocks," Proc. Natl. Acad. Sci. USA, 89:10915-10919 [1992].
Kramer, B., et al., "Different base/base mismatches are corrected with different efficiencies by the methyl-directed DNA mismatch-repair system of E. coli," Cell, 38(3):879-887, 1984.
Ling, M.M., et al., "Approaches to DNA Mutagenesis: An Overview," Anal. Biochem., 254(2):157-78 [1997].
Matsumura, I, "Why Johnny can't clone: Common pitfallsand not so common solutions," Biotechn., 59: IV-XIII [2015].
Matthes, H.W.D., et al., "Simultaneous rapid chemical synthesis of over one hundred oligonucleotides on a microscale," EMBO J., 3(4):801-05 (1984).
Minshull, J., et al., "Protein evolution by molecular breeding," Curr. Op. Chem. Biol., 3(3):284-290 (1999).
Needleman, S., et al., "A general method applicable to the search for similarities in the amino acid sequence of two proteins," J. Mol. Biol. 48:443-453 (1970).
Pearson, W.R., "Improved tools for biological sequence comparison," Proc. Nat'l. Acad. Sci. USA, 85:2444-2448 (1988).
Pheiffer, B.H., et al., "Polymer-stimulated ligation: enhanced blunt- or cohesive-end ligation of DNA or deoxyribooligonudcleotides by T4 DNA Ugase in polymer solutions," Nucl. Acids Res., 11(22): 7853-7871 [1983].
Romanos, M.A., et al., "Foreign gene expression in yeast: a review," Yeast 8:423-488 [1992].
Simonen, M., et al., "Protein Secretion in Bacillus Species," Microbiological Reviews, 57:109-137 (1993).
Smith, M., "In vitro mutagenesis," Ann. Rev. Genet., 19:423-462 (1985).
Smith, T., et al., "Comparison of Biosequences," Adv. Appl. Math, 2:482-489 (1981).
Stemmer, W., "DNA Shuffling by Random Fragmentation and Reassembly: In vitro Recombination for Molecular Evolution," Proc. Natl. Acad. Sci. USA, 91:10747-10751 (1994).
Stemmer, W.P.C., "Rapid evolution of a protein in vitro by DNA shuffling", Nature, 370:389-391 (1994).
Villa-Komaroff, L., et al., "A bacterial clone synthesizing proinsulin," Proc. Natl Acad. Sci. USA, 75:3727-3731 (1978).
Wells, J.A., et al., "Cassette mutagenesis: an efficient method for generation of multiple mutations at defined sites," Gene, 34:315-323 (1985).
Wilson, R.H., et al., "Engineered DNA ligases with improved activities in vitro," Prot. Engin. Des. Select., 26(7):471-478 [2013].
Zhang, J-H., et al., "Directed evolution of a fucosidase from a galactosidase by DNA shuffling and screening, "Proc. Nat. Acad. Sci., U.S.A., 94:4504-4509 (1997).
Zhao, H., et al., "Molecular evolution by staggered extension process (StEP) in vitro recombination," Nat. Biotechnol., 16:258-261 (1998).
Bullard, D.R., et al., "Direct comparison of nick-joining activity of the nucleic acid ligases from bacteriophage T4," Biochem. J., 398:135-144 [2006].
Islam, S., "Efficient ligation of DNA on RNA templates using a mutated T4 DNA ligase," Master's Thesis, University of Uppsala, pp. 1-21 [2008].
UniProt Accession No. A0A0A7HC26 dated Mar. 4, 2015.
UniProt Accession No. E3SF16 dated Jan. 11, 2011.
UniProt Accession No. A0A097J5X7 dated Jan. 18, 2017.
UniProt Accession No. P19088 dated Jan. 18, 2017.
Takahashi, F., et al., "Activity-based in vitro selection of T4 DNA ligase," Biochemical and Biophysical Research Communications, 336(3):987-993 [2005].
European Partial Search Report from EP Corresponding Application No. 21191485.8 dated Dec. 20, 2021.
Saiful Islam, "Efficient ligation of DNA on RNA templates using a mutated T4 DNA ligase," Uppsala Universitet Masters Thesis (2008).
Fumio Takahashi, et al., "Activity-based in vitro selection of T4 DNA ligase," Biochemical and Biophysical Research Communications 336:987-993 (2005).
Uniprot, Accession No. A0A0A7HC26 (rest.uniprot.org/uniprotkb/A0A0A7HC26.txt.
Uniprot, Accession No. A0A097J5X7 (rest.uniprot.org/unisave/A0A097J5X7?from=A0A097J5X7&versions=9&format=txt.
Uniprot, Accession No. P19088 (rest.uniprot.org/unisave/P19088?fromP19088&versions=72&format=txt.

* cited by examiner

US 12,344,872 B2

ENGINEERED LIGASE VARIANTS

The present application claims priority to U.S. Prov. Pat. Appln. Ser. No. 62/503,075, filed May 8, 2017, U.S. Prov. Pat. Appln. Ser. No. 62/540,734, filed Aug. 3, 2017, and U.S. Prov. Pat. Appln. Ser. No. 62/587,030, filed Nov. 16, 2017, each of which is incorporated by reference in its entirety and for all purposes.

REFERENCE TO SEQUENCE LISTING, TABLE OR COMPUTER PROGRAM

The Sequence Listing concurrently submitted herewith under 37 C.F.R. § 1.821 in a computer readable form (CRF) via EFS-Web as file name CX9-160WO1_ST25.txt is herein incorporated by reference. The electronic copy of the Sequence Listing was created on May 7, 2018, with a file size of 100 Kbytes.

FIELD OF THE INVENTION

The present invention provides engineered ligase polypeptides and compositions thereof, as well as polynucleotides encoding the engineered ligase polypeptides. The invention also provides methods for use of the compositions comprising the engineered ligase polypeptides for diagnostic and other purposes.

BACKGROUND OF THE INVENTION

DNA ligases catalyze the formation of new phosophodiester bonds in nucleic acid molecules, through the condensation of adjacent 3'-hydroxyl and 5'-phosphate termini. The enzyme joins blunt and cohesive "sticky" end termini and will also repair single stranded nicks in duplex DNA and some DNA/RNA hybrids. There are various ligases that find use, one of which is the DNA ligase from bacteriophage T4. T4 DNA ligase is one of the most widely-used enzymes in biotechnology. While there are various DNA ligases that have found use, there remains a need in the art for improved ligases for diagnostic and research purposes.

SUMMARY OF THE INVENTION

The present invention provides engineered ligase polypeptides and compositions thereof, as well as polynucleotides encoding the engineered ligase polypeptides. The invention also provides methods for use of the compositions comprising the engineered ligase polypeptides for diagnostic and other purposes.

The present invention provides engineered ligases comprising polypeptide sequences having at least 85%, 90%, 91%, 92%, 93%, 94%, 95%, 96%, 97%, 98%, 99%, or more sequence identity to the reference sequence of SEQ ID NOS:2, 6, 32, 34, and/or 38, or a functional fragment thereof, wherein the engineered ligases comprise at least one substitution or substitution set in their polypeptide sequences, and wherein the amino acid positions of the polypeptide sequences are numbered with reference to SEQ ID NO: 2, 6, 32, 34, or 38.

The present inventon also provides engineered ligases comprising at least one substitution or substitution set, wherein the at least one substitution or substitution set is selected from 52/56/404, 52/56/404/412, 127/207, 127/213, 127/213/276/339, 140/181/234, 165/181/299, 165/181/281/ 299, 238/241/404/412/462, and 462, and/or any combinations thereof, wherein the amino acid positions are numbered with reference to SEQ ID NO: 2. In some embodiments, the substitution(s) or substitution sets comprise substitutions or substitution sets selected from 52E/ 56R/404K, 52E/56V/404K/412T, 127K/207R, 127K/213M, 127K/213M/276G/339V, 140A/181T/234M, 165A/181T/ 299P, 165A/181T/281A/299A, 238L/241L/404K/412T/ 462K, and 462K, wherein the amino acid positions are numbered with reference to SEQ ID NO: 2. In some further embodiments, the the substitutions or substitution sets comprise substitutions or substitution sets selected from K52E/ A56R/N404K, K52E/A56V/N404K/K412T, P127K/I207R, P127K/L213M, P127K/L213M/C276G/I339V, S140A/ S181T/L234M, C165A/S181T/K299P, C165A/S181T/ V281A/K299A, Y238L/N241L/N404K/K412T/I462K, and I462K, wherein the amino acid positions are numbered with reference to SEQ ID NO: 2.

The present invention further provides engineered ligases, comprising at least one substitution or substitution set comprising substitution(s) at amino acid positions selected from 52/127/140/181/462, 52/127/140/181/238, 52/127/181/462, 52/127/276/372/462, 52/127/404, 52/140/181/238/276/293/ 404, 52/140/181/276/299/404/462, 52/140/207/299/372/ 404/462, 52/140/238/276/299/372/404, 52/181, 52/181/238/ 276, 52/181/238/299/404, 52/181/293, 52/207/238/293/299/ 404/462, 52/276/299/404, 52/238/404/462, 52/293/299/404/ 462, 52/404/462, 58/63/89, 58/88/89/226/440, 58/88/199/ 225/226, 58/88/226/306, 58/88/306/470, 58/440/470, 58/451, 63/88/89, 63/88/451, 63/89/226/440/451, 63/89/ 451, 63/199/297/375, 88/225/440/451, 88/306/440/451, 88/470, 89, 127, 127/140/238, 127/140/276, 127/140/299/ 372/462, 127/181/207, 127/181/238/372, 127/181/276, 127/ 181/404, 127/207/238/372, 127/238/293/462, 127/238/293/ 299/372/404, 127/238/293/299/404, 127/238/372/462, 127/ 293, 127/293/372/462, 127/293/404/462, 127/462, 140/238/ 372/462, 140/276/293/404, 140/285/293/404, 140/299/372/ 404/462, 140/372, 140,181/207/238, 181/207/238/276/293/ 372/404, 181/207/238/372, 181/238/276, 181/238/299/404, 181/238/462, 181/276, 181/293, 181/462, 238/293/299/372/ 462, 238/293/372, 238/299/404, 238/404/462, 276/293/462, 276/404, 293/372, 299/372/462, 299/404/462, 372, 372/462, 404, 451, and 462, and/or any combinations thereof, wherein the amino acid positions are numbered with reference to SEQ ID NO: 6. In some embodiments, the substitution(s) or substitution sets comprise substitutions or substitution sets selected from 2E/127K/I40A/181T/462K, 52E/127K/I40A/ 181T/238L, 52E/127K/I81T/462K, 52E/127K/276G/372I/ 462K, 52E/127K/404K, 52E/140A/181T/238L/276G/293E/ 404K, 52E/140A/181T/276G/299P/404K/462K, 52E/140A/ 207R/299P/372I/404K/462K, 52E/140A/238L/276G/299P/ 372I/404K, 52E/181T, 52E/181T/238L/276G, 52E/181T/ 238L/299P/404K, 52E/181T/293E, 52E/207R/238L/293E/ 299P/404K/462K, 52E/276G/299P/404K, 52E/238L/404K/ 462K, 52E/293E/299P/404K/462K, 52E/404K/462K, 58K/ 63R/89K, 58K/88R/89K/226E/440K, 58K/88R/199E/225A/ 226E, 58K/88R/226E/306A, 58K/88R/306A/470E, 58K/ 440K/470E, 58K/451K, 63R/88R/89K, 63R/88R/451K, 63R/89K/226E/440K/451K, 63R/89K/451K, 63R/199E/ 297G/375E, 88R/225A/440K/451K, 88R/306A/440K/ 451K, 88R/470E, 89K, 127K, 127K/I40A/238L, 127K/ I40A/276G, 127K/I40A/299P/372I/462K, 127K/I81T/ 207R, 127K/I81T/238L/372I, 127K/I81T/276G, 127K/ I81T/404K, 127K/207R/238L/372I, 127K/238L/293E/ 462K, 127K/238L/293E/299P/372I/404K, 127K/238L/ 293E/299P/404K, 127K/238L/372I/462K, 127K/293E, 127K/293E/372I/462K, 127K/293E/404K/462K, 127K/ 462K, 140A/238L/372I/462K, 140A/276G/293E/404K, 140A/285A/293E/404K, 140A/299P/372I/404K/462K, 140A/372I, 140T, 181T/207R/238L, 181T/207R/238L/
276G/293E/372I/404K, 181T/207R/238L/372I, 181T/238L/
276G, 181T/238L/299P/404K, 181T/238L/462K, 181T/
276G, 181T/293E, 181T/462K, 238L/293E/299P/372I/
462K, 238L/293E/372I, 238L/299P/404K, 238L/404K/
462K, 276G/293E/462K, 276G/404K, 293E/372I, 299P/
372I/462K, 299P/404K/462K, 372I, 372I/462K, 404K,
451K, and 462K, wherein the amino acid positions are
numbered with reference to SEQ ID NO: 6. In some
additional embodiments, the substitution(s) or substitution
sets comprise substitutions or substitution sets selected from
K52E/P127K/S140A/S181T/I462K, K52E/P127K/S140A/
S181T/Y238L, K52E/P127K/S181T/I462K, K52E/P127K/
C276G/V372I/I462K, K52E/P127K/N404K, K52E/S140A/
S181T/Y238L/C276G/L293E/N404K, K52E/S140A/
S181T/C276G/K299P/N404K/I462K, K52E/S140A/
I207R/K299P/V372I/N404K/I462K, K52E/S140A/Y238L/
C276G/K299P/V372I/N404K, K52E/S181T, K52E/S181T/
Y238L/C276G, K52E/S181T/Y238L/K299P/N404K,
K52E/S181T/L293E, K52E/I207R/Y238L/L293E/K299P/
N404K/I462K, K52E/C276G/K299P/N404K, K52E/
Y238L/N404K/I462K, K52E/L293E/K299P/N404K/
I462K, K52E/N404K/I462K, Q58K/L63R/E89K, Q58K/
E88R/E89K/K226E/E440K, Q58K/E88R/K199E/K225A/
K226E, Q58K/E88R/K226E/K306A, Q58K/E88R/K306A/
K470E, Q58K/E440K/K470E, Q58K/T451K, L63R/E88R/
E89K, L63R/E88R/T451K, L63R/E89K/K226E/E440K/
T451K, L63R/E89K/T451K, L63R/K199E/R297K/K375E,
E88R/K225A/E440K/T451K, E88R/K306A/E440K/
T451K, E88R/K470E, E89K, P127K, P127K/S140A/
Y238L, P127K/S140A/C276G, P127K/S140A/K299P/
V372I/I462K, P127K/S181T/I207R, P127K/S181T/Y238L/
V372I, P127K/S181T/C276G, P127K/S181T/N404K,
P127K/I207R/Y238L/V372I, P127K/Y238L/L293E/
I462K, P127K/Y238L/L293E/K299P/V372I/N404K,
P127K/Y238L/L293E/K299P/N404K, P127K/Y238L/
V372I/I462K, P127K/L293E, P127K/L293E/V372I/I462K,
P127K/L293E/N404K/I462K, P127K/I462K, S140A/
Y238L/V372I/I462K, S140A/C276G/L293E/N404K,
S140A/V285A/L293E/N404K, S140A/K299P/V372I/
N404K/I462K, S140A/V372I, S140T, S181T/I207R/
Y238L, S181T/I207R/Y238L/C276G/L293E/V372I/
N404K, S181T/I207R/Y238L/V372I, S181T/Y238L/
C276G, S181T/Y238L/K299P/N404K, S181T/Y238L/
I462K, S181T/C276G, S181T/L293E, S181T/I462K,
Y238L/L293E/K299P/V372I/I462K, Y238L/L293E/V372I,
Y238L/K299P/N404K, Y238L/N404K/I462K, C276G/
L293E/I462K, C276G/N404K, L293E/V372I, K299P/
V372I/I462K, K299P/N404K/I462K, V372I, V372I/
I462K, N404K, T451K, and I462K, wherein the amino acid
positions are numbered with reference to SEQ ID NO: 6.

The present invention further provides engineered ligases,
comprising at least one substitution or substitution set comprising substitution(s) at amino acid positions selected from
19, 19/127/199, 19/127/306, 19/238, 89, 89/127, 89/127/
238/306, 127, 127/133/238/375, 127/177/238/293/306, 127/
238, 127/306, 127/385, 176/244/247/373/438, 176/250/373/
438/480, 238, 238/306/372, 244, 244/247, 244/247/250,
244/250/438, 244/438, 247/373/427/438, 297, 306, 372,
404, and 438, and/or any combinations thereof, wherein the
amino acid positions are numbered with reference to SEQ
ID NO: 32. In some embodiments, the substitution(s) or
substitution sets comprise substitutions or substitution sets
selected from 19K, 19K/I27K/I99S, 19K/I27K/306A, 19K/
238L, 89K, 89K/I27K, 89K/I27K/238L/306A, 127K, 127K/
I33H/238L/375R, 127K/I77A/238L/293P/306A, 127K/
238L, 127K/306A, 127K/385E, 176G/244S/247K/373A/
438D, 176G/250S/373A/438D/480S, 238L, 238L/306A/
372I, 244S, 244S/247K, 244S/247K/250S, 244S/250S/
438D, 244S/438D, 247K/373A/427K/438D, 297S, 306A,
372I, 404K, and 438D, wherein the amino acid positions are
numbered with reference to SEQ ID NO: 32. In some
additional embodiments, the substitution(s) or substitution
sets comprise substitutions or substitution sets selected from
Q19K, Q19K/P127K/K199S, Q19K/P127K/K306A, Q19K/
Y238L, E89K, E89K/P127K, E89K/P127K/Y238L/K306A,
P127K, P127K/Q133H/Y238L/K375R, P127K/V177A/
Y238L/L293P/K306A, P127K/Y238L, P127K/K306A,
P127K/D385E, D176G/A244S/F247K/D373A/E438D,
D176G/V250S/D373A/E438D/D480S, Y238L, Y238L/
K306A/V372I, A244S, A244S/F247K, A244S/F247K/
V250S, A244S/V250S/E438D, A244S/E438D, F247K/
D373A/E427K/E438D, R297S, K306A, V372I, N404K,
and E438D, wherein the amino acid positions are numbered
with reference to SEQ ID NO: 32.

The present invention further provides engineered ligases,
comprising at least one substitution or substitution set comprising substitution(s) at amino acid positions selected from
51, 56, 60, 63, 86, 149, 174, 184, 199, 207, 233, 237, 238,
240, 314, 329, 371, 373, 385, 427, 438, 439, 446, 448, 451,
452, 453, 454, 461, 466, 476, and 485, and/or any combinations thereof, wherein the amino acid positions are numbered with reference to SEQ ID NO: 32. In some embodiments, the substitution(s) or substitution sets comprise
substitutions or substitution sets selected from 51R, 56S,
60G/V, 63T, 86R, 149R, 174P, 184A, 199T, 207Q/V, 233A/
T, 237N/R, 238L, 240P, 314V, 329G/L, 371V/W, 373A/G,
385A/W, 427L/R, 438D/F/G, 439S, 446R, 448A/G/P, 451G,
452P/V, 453G/L/R/T, 454L, 461C, 466G/P, 476A, and
485G/Y, wherein the amino acid positions are numbered
with reference to SEQ ID NO: 32. In some additional
embodiments, the substitution(s) or substitution sets comprise substitutions or substitution sets selected from P51R,
A56S, F60G/V, L63T, A86R, N149R, L174P, G184A,
K199T, I207Q/V, F233A/T, A237N/R, Y238L, E240P,
Y314V, D329G/L, D371V/W, D373A/G, D385A/W, E427L/
R, E438D/F/G, C439S, K446R, D448A/G/P, K451G,
D452P/V, Y453G/L/R/T, V454L, A461C, E466G/P, D476A,
and T485G/Y, wherein the amino acid positions are numbered with reference to SEQ ID NO: 32.

The present invention further provides engineered ligases,
comprising at least one substitution or substitution set comprising substitution(s) at amino acid positions selected from
7, 17, 52, 54, 59, 74, 85, 183, 199, 240, 241, 242, 280, 321,
235, 237, 371, 404, 405, 451, 452, 453, 454, 462, and 483,
and/or any combinations thereof, wherein the amino acid
positions are numbered with reference to SEQ ID NO: 32.
In some embodiments, the substitution(s) or substitution sets
comprise substitutions or substitution sets selected from 7L,
17R, 52G, 54E, 59M, 74G/T, 85T, 183N, 199G, 240P, 241G,
242H, 280L, 321A/R, 235R, 237G, 371G, 4045/G, 405G,
451G, 452P, 453L, 454A, 462Q, and 483G/Q, wherein the
amino acid positions are numbered with reference to SEQ
ID NO: 32. In some additional embodiments, the substitution(s) or substitution sets comprise substitutions or substitution sets selected from N7L, Q17R, K52G, G54E, S59M,
F74G/T, A85T, A183N, K199G, E240P, N241G, S242H,
Q280L, E321A/R, F235R, A237G, D371G, N4045, A405G,
K451G, D452P, Y453L, V454A, I462Q, and E483G/Q,
wherein the amino acid positions are numbered with reference to SEQ ID NO: 32.

The present invention further provides engineered ligases,
comprising at least one substitution or substitution set comprising substitution(s) at amino acid positions selected from 7, 11, 13, 14, 54, 62, 89, 149, 183, 184, 185, 186, 231, 232, 233, 238, 239, 240, 385, 386, 413, and 453, and/or any combinations thereof, wherein the amino acid positions are numbered with reference to SEQ ID NO: 6. In some embodiments, the substitution(s) or substitution sets comprise substitutions or substitution sets selected from 7K, 11K, 13K, 14K, 54K, 62K, 89K, 149K, 183K, 184K, 185K, 186K, 231K, 232K, 233K, 238K, 239K, 240K, 385K, 386K, 413K, and 453K, wherein the amino acid positions are numbered with reference to SEQ ID NO: 6. In some additional embodiments, the substitution(s) or substitution sets comprise substitutions or substitution sets selected from N7K, 511K, G13K, S14K, G54K, M62K, E89K, N149K, A183K, G184K, N185K, E186K, L231K, D232K, F233K, Y238K, P239K, E240K, D385K, P386K, A413K and Y453K, wherein the amino acid positions are numbered with reference to SEQ ID NO: 6.

The present invention further provides engineered ligases, comprising at least one substitution or substitution set comprising substitution(s) at amino acid positions selected from 19/63/233/237/371/452, 19/237/453, 63/89/448/452/453, 63/149/240/371/452, 63/233/240/452/454, 86/89/149/233/237/240, 86/89/149/233/237/314/452, 86/89/233/237/240/448, 89/233/237/240/448/453/454, 89/240/454, 149/233/237/454, 149/237/240, 149/237/240/329/404/453, 233/237/371/404/452/454, and 233/237/404, and/or any combinations thereof, wherein the amino acid positions are numbered with reference to SEQ ID NO: 34. In some embodiments, the substitution(s) or substitution sets comprise substitutions or substitution sets selected from 19K/63T/233A/237R/371W/452P, 19K/237N/453G, 63T/89K/448A/452P/453G, 63T/I49R/240P/371W/452P, 63T/233A/240P/452P/454L, 86R/89K/I49R/233A/237N/240P, 86R/89K/I49R/233A/237R/314V/452P, 86R/89K/233A/237N/240P/448A, 89K/233A/237R/240P/448A/453G/454L, 89K/240P/454L, 149R/233A/237N/454L, 149R/237N/240P, 149R/237N/240P/329G/404K/453G, 233A/237N/371W/404K/452P/454L, and 233A/237R/404K, wherein the amino acid positions are numbered with reference to SEQ ID NO: 34. In some additional embodiments, the substitution(s) or substitution sets comprise substitutions or substitution sets selected from Q19K/L63T/F233A/A237R/D371W/D452P, Q19K/A237N/Y453G, L63T/E89K/D448A/D452P/Y453G, L63T/N149R/E240P/D371W/D452P, L63T/F233A/E240P/D452P/V454L, A86R/E89K/N149R/F233A/A237N/E240P, A86R/E89K/N149R/F233A/A237R/Y314V/D452P, A86R/E89K/F233A/A237N/E240P/D448A, E89K/F233A/A237R/E240P/D448A/Y453G/V454L, E89K/E240P/V454L, N149R/F233A/A237N/V454L, N149R/A237N/E240P, N149R/A237N/E240P/D329G/N404K/Y453G, F233A/A237N/D371W/N404K/D452P/V454L, and F233A/A237R/N404K, wherein the amino acid positions are numbered with reference to SEQ ID NO: 34.

The present invention further provides engineered ligases, comprising at least one substitution or substitution set comprising substitution(s) at amino acid positions selected from 13/89/183/231, 13/89/183/232/386/451, 13/183/232/329/453/466, 13/183/232/386/451, 13/232/385/451, 89/183/329/451/453, 149/183, 183, 183/207/386, 183/207/386/427/453, 183/207/439, 183/231/373, 183/231/385/427, 183/231/427/466, 183/373/386, 183/385, 183/385/427, 183/413/427, 183/427/451, and 385/453/466, and/or any combinations thereof, wherein the amino acid positions are numbered with reference to SEQ ID NO: 38. In some embodiments, the substitution(s) or substitution sets comprise substitutions or substitution sets selected from 13K/89K/I83K/231K, 13K/89K/I83K/232K/329G/453G/466G, 13K/I83K/232K/386K/451G, 13K/232K/385K/451G, 89K/I83K/329G/451G/453R, 149R/183K, 183K, 183K/207V/386K, 183K/207V/386K/427R/453G, 183K/207V/439S, 183K/231K/373G, 183K/231K/385K/427R, 183K/231K/427R/466G, 183K/373A/386K, 183K/385K, 183K/385K/427R, 183K/413K/427R, 183K/427R/451G, and 385K/453R/466G, wherein the amino acid positions are numbered with reference to SEQ ID NO: 38. In some additional embodiments, the substitution(s) or substitution sets comprise substitutions or substitution sets selected from G13K/E89K/A183K/L231K, G13K/E89K/A183K/D232K/P386K/K451G, G13K/A183K/D232K/D329L/Y453G/E466G, G13K/A183K/D232K/P386K/K451G, G13K/D232K/D385K/K451G, E89K/A183K/D329G/K451G/Y453R, N149R/A183K, A183K, A183K/I207V/P386K, A183K/I207V/P386K/E427R/Y453G, A183K/I207V/C439S, A183K/L231K/D373G, A183K/L231K/D385K/E427R, A183K/L231K/E427R/E466G, A183K/D373A/P386K, A183K/D385K, A183K/D385K/E427R, A183K/A413K/E427R, A183K/E427R/K451G, and D385K/Y453R/E466G, wherein the amino acid positions are numbered with reference to SEQ ID NO: 38.

The present invention further provides engineered ligases, comprising at least one substitution or substitution set comprising substitution(s) at amino acid positions selected from 13/19/63/88/127/183/225/232/233/237/329/371/440/451/452/453/466, 13/19/63/88/127/183/225/232/233/237/371/386/440/451/452, 19/63/88/127/183/225/231/233/237/371/427/440/451/452/466, 19/63/88/127/183/225/233/237/371/373/386/440/451/452, 19/63/88/127/225/233/237/371/385/440/451/452/453/466, 19/63/88/127/225/233/237/371/440/451/452, 63/88/127/149/225/240/371/440/451/452, 86/88/89/127/149/225/233/237/240/440/451, 88/89/127/225/233/237/240/440/448/451/453/454, 88/127/149/225/233/237/440/451/454, 88/127/225/440/451, and 88/225/440/451, and/or any combinations thereof, wherein the amino acid positions are numbered with reference to SEQ ID NO: 6. In some embodiments, the substitution(s) or substitution sets comprise substitutions or substitution sets selected from 13K/I9K/63T/88R/127K/I83K/225A/232K/233A/237R/329L/371W/440K/451K/452P/453G/466G, 13K/I9K/63T/88R/127K/I83K/225A/232K/233A/237R/371W/386K/440K/451G/452P, 19K/63T/88R/127K/I83K/225A/231K/233A/237R/371W/427R/440K/451K/452P/466G, 19K/63T/88R/127K/I83K/225A/233A/237R/371W/373A/386K/440K/451K/452P, 19K/63T/88R/127K/225A/233A/237R/371W/385K/440K/451K/452P/453R/466G, 19K/63T/88R/127K/225A/233A/237R/371W/440K/451K/452P, 63T/88R/127K/I49R/225A/240P/371W/440K/451K/452P, 86R/88R/89K/I27K/I49R/225A/233A/237N/240P/440K/451K, 88R/89K/I27K/225A/233A/237R/240P/440K/448A/451K/453G/454L, 88R/127K/I49R/225A/233A/237N/440K/451K/454L, 88R/127K/225A/440K/451K, and 88R/225A/440K/451K, wherein the amino acid positions are numbered with reference to SEQ ID NO: 6. In some additional embodiments, the substitution(s) or substitution sets comprise substitutions or substitution sets selected from G13K/Q19K/L63T/E88R/P127K/A183K/K225A/D232K/F233A/A237R/D329L/D371W/E440K/T451K/D452P/Y453G/E466G, G13K/Q19K/L63T/E88R/P127K/A183K/K225A/D232K/F233A/A237R/D371W/P386K/E440K/T451G/D452P, Q19K/L63T/E88R/P127K/A183K/K225A/L231K/F233A/A237R/D371W/E427R/E440K/T451K/D452P/E466G, Q19K/L63T/E88R/P127K/A183K/K225A/F233A/A237R/D371W/D373A/P386K/E440K/T451K/D452P, Q19K/L63T/E88R/P127K/K225A/F233A/A237R/D371W/D385K/E440K/T451K/D452P/Y453R/E466G, Q19K/

L63T/E88R/P127K/K225A/F233A/A237R/D371W/ E440K/T451K/D452P. L63T/E88R/P127K/N149R/K225A/ E240P/D371W/E440K/T451K/D452P, A86R/E88R/E89K/ P127K/N149R/K225A/F233A/A237N/E240P/E440K/ T451K, E88R/E89K/P127K/K225A/F233A/A237R/E240P/ E440K/D448A/T451K/Y453G/V454L, E88R/P127K/ N149R/K225A/F233A/A237N/E440K/T451K/V454L, E88R/P127K/K225A/E440K/T451K, and E88R/K225A/ E440K/T451K, wherein the amino acid positions are numbered with reference to SEQ ID NO: 6.

The present invention also provides engineered ligases comprising polypeptide sequences that are at least 85%, 90%, 91%, 92%, 93%, 94%, 95%, 96%, 97%, 98%, 99% or more identical to the sequence of at least one engineered ligase variant set forth in Table 4.1, 4.2, 4.3, 5.1, 5.2, 5.3, 5.4, 5.5, and/or 6.1. In some embodiments, engineered ligase is a variant engineered ligase provided in Table 4.1, 4.2, 4.3, 5.1, 5.2, 5.3, 5.4, 5.5, and/or 6.1. In some further embodiments, the engineered ligase has DNA ligase activity. In some additional embodiments, the engineered ligase has at least one improved property, as compared to wild-type T4 DNA ligase. In some further embodiments, the engineered ligases of the present invention have at least one improved property, as compared to wild-type T4 DNA ligase, wherein the improved property is selected from exhibiting greater activity with low DNA substrate concentrations, and production of fewer adapter dimers. In some further embodiments, the engineered ligases of the present invention are more thermostable than wild-type T4 DNA ligase. In yet some further embodiments, the engineered ligases of the present invention are stable over a broader pH range than wild-type T4 DNA ligase. In some additional embodiments, the engineered ligases of the present invention are purified.

The present invention also provides polynucleotide sequences encoding at least one engineered ligase provided herein. In some embodiments, the polynucleotide sequence encodes at least one engineered ligase having at least 85%, 90%, 91%, 92%, 93%, 94%, 95%, 96%, 97%, 98%, 99%, or more sequence identity to the reference sequence of SEQ ID NOS:2, 6, 32, 34, and/or 37, or a functional fragment thereof, wherein the engineered polypeptide comprises at least one substitution at one or more amino acid positions. In some embodiments, the polynucleotide sequence comprises a sequence having at least 85%, 90%, 91%, 92%, 93%, 94%, 95%, 96%, 97%, 98%, 99%, or more sequence identity to the reference sequence of SEQ ID NOS:1, 5, 31, 33, and/or 37. In some further embodiments, the polynucleotide sequence comprises SEQ ID NOS:1, 5, 31, 33, and/or 37. In yet some additional embodiments, the polynucleotide sequence is operably linked to a control sequence. In some further embodiments, the polynucleotide sequence is codon-optimized.

The present invention also provides expression vectors comprising at least one polynucleotide sequence provided herein. The present invention also provides host cells transformed with at least expression vector provided herein.

The present invention further provides methods of producing an engineered ligase polypeptide in a host cell comprising culturing a host cell provided herein, under suitable culture conditions, such that at least one engineered ligase is produced. In some embodiments, the methods further comprise recovering at least one engineered ligase from the culture and/or host cells. In some additional embodiments, the methods further comprise the step of purifying the at least one engineered ligase.

The present invention also provides compositions comprising at least one engineered ligase provided herein. It is not intended that the composition comprise any engineered ligases provided herein that have been produced using any particular method. It is intended that the present invention be limited to engineered ligases produced using any specific method.

The present invention also provides methods to produce at least one ligation product, comprising at least one engineered ligase provided herein, and a reaction mixture comprising at least two nucleic acid fragments, combining at least one engineered polypeptide and the reaction mixture under conditions such that ligation of the nucleic acid fragments occurs and at least one ligation product is produced. In some embodiments of the methods, the input double-stranded DNA comprises blunt ended DNA fragments.

The present invention also provides methods to produce a ligation product, comprising at least one engineered ligase provided herein, and a reaction mixture comprising at least two nucleic acid fragments, combining at least one engineered polypeptide and the reaction mixture under conditions such that ligation of the nucleic acid fragments occurs and at least one ligation product is produced. In some embodiments of the methods, the input double-stranded DNA comprises blunt ended DNA fragments.

The present invention also provides methods for producing product comprising a DNA library, comprising providing at least one engineered ligase provided herein and a reaction mixture composition comprising input double-stranded DNA, at least one T-tailed adapter oligonucleotide, adenosine, and a reaction buffer; exposing the at least one engineered ligase and the reaction mixture under conditions such that an adenosine is added to the 3' ends of both strands of the DNA, and ligation of the T-tailed adapter to the ends of the input DNA, to produce a DNA library. In some embodiments of the methods, the input double-stranded DNA comprises blunt ended DNA fragments.

The present invention also provides methods for producing product comprising a plurality of DNA fragment suitable for sequencing, comprising providing at least one engineered ligase provided herein, and a reaction mixture comprising input double-stranded DNA, an oligonucleotide comprising single-base deoxyadenine 3' overhangs and 5' monophosphate ends, an adapter oligonucleotide comprising a 5' deoxythymidine overhang and 5' phosphate at the ligation compatible end, and; exposing the at least one engineered ligase and the reaction mixture under conditions such that ligation of the oligonucleotide, adapter oligonucleotide, and input double-stranded DNA occurs, producing a product comprising plurality of DNA fragments suitable for sequencing.

In some embodiments of the methods utilizing the engineered ligase of the present invention, the exposure is performed in the presence of a crowding agent. In some embodiments of the methods, the product is transformed into *E. coli* after heat inactivation of the product. In some additional embodiments, the product is used to generate a library of DNA molecules. In some further embodiments, the library of DNA molecules is subjected to sequencing. In yet some additional embodiments, the reaction mixture comprises at least one compound that inhibits ligation. In yet some further embodiments, the methods comprise at least one compound that inhibits ligation comprises a sub-optimal buffer for ligation. In some embodiments, the method produces more product than the same methods in which wild-type T4 DNA ligase is used. In some additional embodiments, the reaction mixture comprises at least one enzyme. In some further embodiments, the enzyme is selected from polymerases, poly nucleotide kinases, exonucleases, endonucleases, and cytidine deaminases. In yet some additional embodiments, the input double-stranded DNA concentration is less than 100 nM, less than 50 nM, less than 10 nM, less than 1 nM, or less than 100 pM. In some further embodiments, the adapter concentration is less than 10-fold, less than 5-fold, less than 3-fold, or less than 2-fold excess of the concentration of inserts in the reaction. In yet some additional embodiments, the methods further comprise the step of amplifying the product. In some further embodiments, the methods further comprise the step of sequencing the product. In yet some additional embodiments, the methods further comprise the steps of amplifying and sequencing the product. In some additional embodiments, no steps are taken to remove adapter dimer from the product. In some further embodiments, the input double-stranded DNA is selected from isolated cell-free DNA, circulating tumor DNA, DNA isolated from circulating tumor cells, circulating fetal DNA, and fine-needle aspirates. In some embodiments, the input double-stranded DNA is provided in a crude sample. In some further embodiments, the input double-stranded DNA is purified prior to its inclusion in the reaction mixture. In yet some additional embodiments, the input double-stranded DNA is derived from a sample comprising nucleic acid, including single-stranded DNA, single-stranded RNA, double-stranded DNA, double-stranded RNA, and/or any other synthetic or naturally-occurring sequence of nucleic acid. Indeed, it is not intended that the present invention be limited to any particular starting sample DNA. In some embodiments, the method is conducted under conditions selected from in a microfluidic devices and droplets. In some further embodiments, the volume of the combination of the reaction mixture and the engineered ligase is less than 5000 pL, less than 1000 pL, less than 100 pL, less than 10 pL, or less than 1 pL. In some additional embodiments, the double-stranded input DNA is immobilized, while in some alternative embodiments, the engineered ligase is immobilized. In yet some further embodiments, the double-stranded input DNA and the engineered ligase are immobilized. In some further embodiments, at least one compound in the reaction mixture is immobilized, in addition to or instead of immobilized DNA and/or immobilized engineered ligase. In some further embodiments, the product is used to generate libraries for DNA sequencing, high-throughput screening, genetic selections, phage display, yeast display, ribosomal display, cell-based assays, biochemical assays, imaging-based high-content screening, or chromatin conformation capture (C3).

In some embodiments of the methods of the present invention, the time length of exposing is less than 30 minutes. In some further embodiments, the time length of exposing is less than 15 minutes. In some additional embodiments, the time length of exposing is less than 10, 9, 8, 7, 6, 5, 4, 3 or 2 minutes. In yet some additional embodiments, the time length of exposing is less than 5 minutes.

In some embodiments of the present invention, the product comprises fewer adapter dimers than ligation methods in which the time length of exposing is 15 minutes or more. Thus, in some embodiments, the present invention provides methods that are quicker and produce fewer adapter dimers, resulting in more productive reads per sample analyzed, as compared to wild-type T4 DNA ligase, and in some embodiments, other ligases. In some additional embodiments, the methods of the present invention are cell-free.

The present invention also provides methods for producing a ligation product, comprising providing at least one engineered ligase provided herein, a substrate comprising at least two nucleic acid fragments, and a reaction mixture; combining at least one engineered ligase, the substrate, and the reaction mixture under conditions such that ligation of the nucleic acid fragments occurs and at least one ligation product is produced.

The present invention also provides methods for producing a DNA library, comprising providing at least one engineered ligase provided herein, a substrate comprising input double-stranded DNA, and a reaction mixture composition comprising at least one T-tailed adapter oligonucleotide, adenosine, and a reaction buffer; combining at least one engineered ligase, the substrate, and the reation mixture under conditions such that an adenosine is added to the 3' ends of both strands of the DNA, and ligation of the T-tailed adapter to the ends of the input DNA, to producing a product comprising a DNA library. In some embodiments, the input double-stranded DNA comprises blunt ended DNA fragments.

The present invention also provides methods for producing a plurality of DNA fragments suitable for sequencing, comprising providing at least one engineered ligase provided herein, a substrate comprising input double-stranded DNA, and a reaction mixture comprising an oligonucleotide comprising single-base deoxyadenine 3' overhangs and 5' monophosphate ends, an adapter oligonucleotide comprising a 5' deoxythymidine overhang and 5' phosphate at the ligation compatible end; and combining at least one engineered ligase, the substrate, and the reaction mixture under conditions such that ligation of the oligonucleotide, adapter oligonucleotide, and input double-stranded DNA occurs, producing a product comprising plurality of DNA fragments suitable for sequencing.

The present invention also provides methods for producing a plurality of DNA fragments suitable for sequencing, comprising providing at least one engineered ligase provided herein, a substrate comprising input double-stranded DNA, and a reaction mixture comprising an oligonucleotide comprising single-base deoxyadenine 3' overhangs and 5' monophosphate ends, an adapter oligonucleotide comprising a 5' deoxythymidine overhang and 5' phosphate at the ligation compatible end; and combining at least one engineered ligase, the substrate, and the reaction mixture under conditions such that ligation of the oligonucleotide, adapter oligonucleotide, and input double-stranded DNA occurs, producing a product comprising plurality of DNA fragments suitable for sequencing, wherein the concentration of the adapter oligonucleotide in the reaction mixture is less than a 20-fold molar excess of the substrate concentration.

In some embodiments of the methods provided herein, the exposing is performed in the presence of a crowding agent. In some further embodiments, the product is transformed into E. coli after heat inactivation of the product. In some additional embodiments, the product is used to generate a library of DNA molecules. In yet some further embodiments, the library of DNA molecules is subjected to sequencing. In still some further embodiments, the reaction mixture comprises at least one compound that inhibits ligation. In some embodiments, at least one compound that inhibits ligation comprises a sub-optimal buffer for ligation. In some particularly preferred embodiments, the methods produce more product than the same methods comprising wild-type T4 DNA ligase. In some additional embodiments, the reaction mixture comprises at least one enzyme. In some embodiments, the enzyme is selected from polymerases, poly nucleotide kinases, exonucleases, endonucleases, and cytidine deaminases. In some embodiments, the enzyme is incompatible with ligase buffer. In yet some further embodiments utilizing input double-strand DNA, the input double-stranded DNA concentration is less than 100 nM, less than 50 nM, less than 10 nM, less than 1 nM, or less than 100 pM. In some embodiments, utilizing adapters, the adapter concentration is less than 10-fold, less than 5-fold, less than 3-fold, or less than 2-fold excess of the concentration of inserts in the reaction. In some additional embodiments, the methods further comprise the step of amplifying the product. In still some further embodiments, the methods further comprise the step of sequencing the product. In yet some additional embodiments, the methods further comprise the steps of amplifying and sequencing the product. In some embodiments, no steps are taken to remove adapter dimer from the product. In yet some further embodiments, the substrate is selected from isolated cell-free DNA, circulating tumor DNA, DNA isolated from leukemia cells, DNA isolated from lymphoma cells, DNA isolated from circulating tumor cells, DNA isolated from virally-infected cells, circulating fetal DNA, and fine-needle aspirates. In some embodiments, the substrate comprises input double-stranded DNA provided in a crude sample. In some alternative embodiments, the substrate comprises input double-stranded DNA that is purified prior to its inclusion in the reaction mixture. In some additional embodiments, the methods are conducted under conditions utilizing microfluidic devices and/or droplets. In some embodiments, the volume of the combination of reaction mixture and engineered ligase is less than 5000 pL, less than 1000 pL, less than 100 pL, less than 10 pL, or less than 1 pL. In some embodiments, the substrate comprises immobilized double-stranded input DNA. In some alternative embodiments, the engineered ligase is immobilized. In yet some additional embodiments, a substrate comprising double-stranded input DNA and the engineered ligase are immobilized. In yet some further embodiments, at least one compound in the reaction mixture is immobilized. In some additional embodiments, the product of the methods is used to generate libraries for DNA sequencing, high-throughput screening, genetic selections, phage display, yeast display, ribosomal display, cell-based assays, biochemical assays, imaging-based high-content screening, or chromatin conformation capture (C3). In some embodiments, the time length of combining is less than 30 minutes. In some further embodiments, the time length of combining is less than 15 minutes. In yet some additional embodiments, the time length of combining is less than 10, 9, 8, 7, 6, 5, 4, 3 or 2 minutes. In some embodiments, the time length of combining is less than 5 minutes. In some additional embodiments of the methods, the product comprises fewer adapter dimers than ligation methods in which the time length of combining is 15 minutes or more. In yet some further embodiments, the methods are cell-free. In some embodiments, the substrate is cell-free DNA extracted from a fluid obtained from a patient. In some further embodiments, the fluid comprises serum or plasma. In some additional embodiments, the substrate comprises nucleic acids with differing sequences at their 3' and 5' ends. In yet some additional embodiments, the methods achieve low bias in the ligation. In yet some further embodiments, the combining is conducted at a temperature in the range between about 10° to about 40° C. In some embodiments, the temperature range is about 16° to about 37° C. In some embodiments, using a temperature in the range of 16° to 37° provides improved conversion to product, as compared with other ligases (e.g., wild-type T4 DNA ligase or other ligases known in the art). In some embodiments, the combining is conducted at a pH in the range of about pH 7 to about pH 10. In some embodiments, the combining is conducted at a pH between about 7.5 and about 9. In some embodiments, the pH of the methods is in the range of 7.5 to 9, wherein recovery is possible in a buffer that is incompatible for use with wild-type T4 DNA ligase or other ligases (e.g., other ligases known in the art). It is not intended that the present invention be limited to methods in which the pH is in the range of 7.5 to 9, as other pHs find use in the present invention. It is also not intended that the present invention be limited to any specific buffer(s), as various buffers find use in the present invention. In some additional embodiments, the use of adapter concentrations less than a 20-fold molar excess of the substrate concentrations find use in achieving both efficient library conversion and/or avoiding carry-over of adapter molecules into downstream steps in which the products are used. It is not intended that the methods of the present invention be limited to such a 20-fold molar substrate excess, as other substrate concentrations find use in the methods of the present invention. In some embodiments, the engineered ligase finds use in preventing index hopping.

DESCRIPTION OF THE INVENTION

Figure 1:
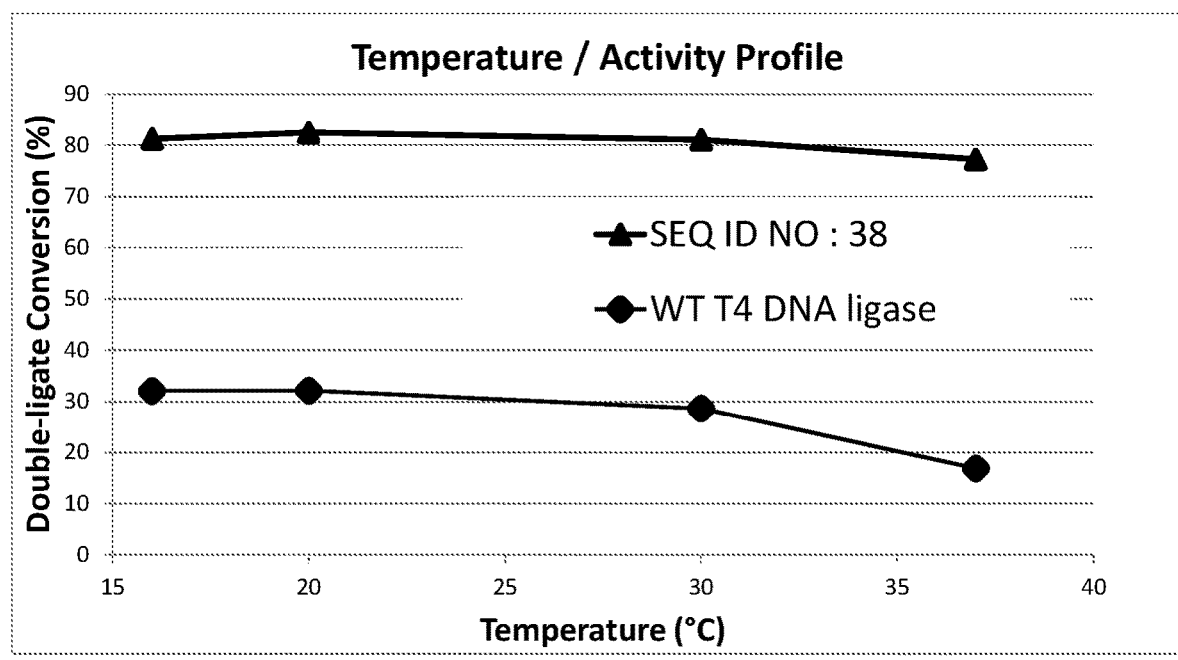
FIG. 1 provides a graph showing the temperature/activity profile for conversion to double-end ligated products for multiple temperature conditions by the polypeptide of SEQ ID NO: 38 and wild-type T4 DNA ligase, as described in Example 9.

The present invention provides engineered ligase polypeptides and compositions thereof, as well as polynucleotides encoding the engineered ligase polypeptides. The invention also provides methods for use of the compositions comprising the engineered ligase polypeptides for diagnostic and other purposes. In some embodiments, the engineered ligase polypeptides are optimized to provide enhanced ligation activity, particularly under conditions involving low concentrations of DNA input and other conditions unfavorable to production of ligated DNA products, especially DNA suitable for high-throughput analysis and/or sequencing reactions. In some embodiments, the present invention provides methods and compositions comprising the engineered ligases for diagnostic and research purposes. The present invention also provides engineered ligase polypeptides, mutants, biologically active fragments and analogues thereof, and compositions comprising the same.

DNA ligases catalyze the formation of new phosphodiester bonds in nucleic acid molecules, through the condensation of adjacent 3'-hydroxyl and 5'-phosphate termini. The native substrate for T4 DNA ligase is a nicked double-stranded ("ds") DNA intermediate generated during DNA replication. In practical in vitro applications such as molecular cloning and DNA sequencing library preparation, T4 DNA ligase is commonly used for its relative efficiency, as compared to other naturally-occurring ligases, for joining cohesive- or blunt-ended ds DNA fragments.

Ligation efficiency is affected by substrate concentrations and the properties of the double-stranded DNA substrates being joined. T4 DNA ligase has very low absolute affinity (Km ~50 µM) for substrates in double-stranded end-joining reactions. However, it is often employed in reactions containing DNA concentrations as low as 1 nm (Matsumura, Biotechn., 95: IV-XIII [2015]). While T4 DNA ligase will join blunt-ended and single-base cohesive overhangs (e.g., a T/A overhang), the efficiency of these reactions is significantly reduced, relative to that between substrates with longer cohesive ends which can form transiently annealed intermediates at 16-20° C. Next-Generation Sequencing (NGS) library preparation workflows depend on ligating double-stranded adapter molecules to the input DNA, presenting perhaps the most demanding conditions for ligation: single-base or blunt-ended insert and adapter substrates and low input DNA concentrations (e.g., from cell-free DNA, single cells, fine-needle aspirates or other low-yield DNA samples.)

Several approaches to improve DNA ligation rate and efficiency have been developed. Currently, the most commonly used approach involves the addition of non-specific polymers (e.g., crowding agents) to the reaction. The addition of polyethylene glycol (PEG; molecular weight 1000-8000) and Ficoll 70 can improve both rate and overall substrate conversion (See, Pheiffer and Zimmerman, Nucl. Acids Res., 11: 7853-7871 [1983]). Ligation buffers containing PEG6000 are widely used in fast ligation cloning and NGS library preparation kits (e.g., kits available from commercial suppliers such as Promega [Promega, Inc., Madison, WI] and New England Biolabs [New England Biolabs, Ipswich, MA]). However, at higher concentrations of crowding agent, several undesirable outcomes increase, including the formation of higher molecular-weight concatamers, and ligation of mismatched substrates, such as adapter dimers formed in NGS reactions. In addition, crowding agents may be incompatible with other enzymatic reactions performed in single-tube or microfluidics workflows. For example, heat inactivation of DNA ligase is commonly performed before *E. coli* transformation, but heat-inactivation in the presence of PEG significantly reduces transformation efficiency. Buffers and ligation master mixes containing high concentrations of crowding agents can also be very viscous, which complicates automated liquid handling and high-throughput sample processing.

Lower molecular-weight ligation enhancers (e.g., 1,2-propanediol), have been used to improve ligation efficiency in cloning and NGS workflows (See e.g., US Pat. Appln. Publ. No. 2014/0187447, incorporated herein by reference). The use of a 1,2-propanediol ligation buffer increased NGS library conversion 5-fold relative to a PEG buffer using a low-concentration DNA input (5 ng *E. coli* DNA). While 1,2-propanediol and other small-molecule enhancers are compatible with heat-inactivation, they may be incompatible with other enzymes or steps in single-tube NGS workflows or microfluidic sample preparation.

Engineered improved T4 DNA ligase variants have been developed by generating various peptide fusions with dsDNA binding domains (See, Wilson et al., Prot. Engin. Des. Select., 7:471-478 [2013]). Several of these ligase variants expressed well and exhibited improved activity on cohesive-end substrates at a concentration of ~40 nM or blunt-ended substrates at a concentration of ~30 nM. However, none of these ligases were reported to have been tested at the low substrate concentrations typically used for cell-free DNA inputs (1-5 nM) or other low-input NGS applications.

The sensitivity of NGS-based sequencing reactions is currently limited by the fractional conversion of fragmented input DNA into double-end adapter-ligated fragments, which can be as low as 5%, using low concentration substrate inputs. While various ligases, crowding agents, and ligation enhancers have found use, the sensitivity of NGS-based sequencing assays and robustness of other molecular biology workflows are limited by the current methods available. The engineered ligases, compositions, and methods of the present invention address the needs in the art for improved NGS-based sequencing and other diagnostic methods and procedures.

In some embodiments, the engineered ligases of the present invention find use in diagnostic and research applications using small amounts of DNA from patient samples, including cell-free DNA, circulating tumor DNA, DNA isolated from circulating tumor cells, circulating fetal DNA, DNA isolated from virally infected cells, fine-needle aspirates, or single cells isolated by FACS (fluorescence activated cell sorting), laser-capture microscopy, or microfluidic devices. However, it is not intended that the sample used with the present invention be limited to any particular sample type, as any suitable sample, including those with low DNA concentrations finds use in the present invention.

In some embodiments, the engineered ligases of the present invention find use in the construction of DNA sequencing libraries for intermediate to high-concentration DNA samples. The engineered ligases provided herein require lower concentrations of adapter to achieve double-adapter ligation conversion equivalent to the WT DNA ligases (e.g., wild-type T4 DNA ligase). As a result of using lower adapter concentrations, the production of adapter dimers is minimized. In some embodiments, adapters are used in limiting concentrations, such that the desired double adapter-ligated product occurs in a high molar excess relative to adapter dimer, and cleanup steps which are otherwise required to remove adapter dimer, are eliminated. This simplifies many standard sequencing workflows, such as genome resequencing. Lower adapter concentrations also reduce the amount of adapter required for the ligation, which can reduce the cost contribution of the adapter for the overall workflow. This is particularly helpful for costly adapters such as methylated adapters used for bisulfate or methylome sequencing.

In some embodiments, the engineered ligases of the present invention find use in molecular cloning applications, particularly those where the DNA concentration is low compared to the Km of naturally occurring enzymes. In some embodiments, this applies to high-throughput cloning applications where sample is prepared in small volumes, or any low-concentration DNA sample such as environmental samples, patient samples, or ancient DNA.

In some embodiments, the engineered ligases of the present invention find use in simplified molecular biology workflows, included automated workflows, which remove cleanup steps between operations. Because engineered ligases are active on low-concentration substrates, a smaller volume (or a dilution) of the substrate sample containing inhibitor can be added to the ligation reaction. Relevant inhibitor-containing DNA samples may include DNA in PCR buffer, DNA in electrophoresis buffer, or DNA in crude extracts. Engineered ligases of the present invention are capable of efficiently ligate diluted samples, as compared to native ligases. Alternatively, in other embodiments, engineered ligases of the present invention find use on undiluted samples containing inhibitor(s). By virtue of their higher specific activity, the ligation performance of these engineered ligases exceeds that of wild-type ligases (e.g., wild-type T4 DNA ligase), in the presence of inhibitors.

Heat inactivation of T4 DNA ligase is commonly performed on ligation reactions prior to transformation of *E. coli*. This step is convenient compared to column or bead-based cleanups, and dramatically increases the efficiency of plasmid transformation. Poly ethylene glycol (PEG) is often used to increase the rate and efficiency of T4 DNA ligase (and other native ligases), but heat inactivation of the ligase in the presence of PEG is strongly inhibitory for transformation. Thus, PEG ligations require more involved cleanup steps, negating the convenience and speed of the PEG rapid-ligation strategy. In some embodiments, the engineered ligases of the present invention perform rapid and efficient ligation in the absence of PEG, and may be inactivated by heat transformation prior to transformation. Thus, use of these engineered ligases achieves both rapid ligation and convenient cleanup prior to transformation.

In some embodiments, the engineered ligases of the present invention find use in microfluidics applications, including those that are incompatible with highly viscous ligation enhancers or crowding agents (e.g., PEG, Ficoll, or high concentrations of glycerol). The engineered ligases of the present invention efficiently convert low-concentration substrates in the absence of the crowding agents that would be required to achieve similar efficiency using native T4 DNA ligase or other ligases.

In some embodiments, the engineered ligases of the present invention find use in single-pot multi-enzyme reactions, performed in microfluidic droplets, or wellplates. The high specific activity of the ligases allow for buffer formulations selected for the performance of other enzymes in the reaction, which achieving ligation performance that is not limiting for the overall workflow.

In some embodiments, the engineered ligases of the present invention find use in the construction of DNA libraries. These libraries may be used for DNA sequencing, high-throughput screening, genetic selections, phage display, yeast display, ribosomal display, cell-based assays, biochemical assays, or imaging-based high-content screening. In some embodiments, the engineered ligases of the present invention find particular utility when the library size, diversity, or fidelity is limited by ligation substrate concentration when a wild-type ligase is used.

In some embodiments, the engineered ligases of the present invention find use in the performance of chromatin conformation capture (C3)-based assays, including 3C, 4C, 5C, and Hi-C. These assays depend on the efficient ligation of digested substrates, under very dilute conditions which are required to promote intramolecular ligation. In some embodiments, the engineered ligases of the present invention perform more efficiently than wild-type T4 DNA ligase under these conditions.

Abbreviations and Definitions:

Unless defined otherwise, all technical and scientific terms used herein generally have the same meaning as commonly understood by one of ordinary skill in the art to which this invention pertains. Generally, the nomenclature used herein and the laboratory procedures of cell culture, molecular genetics, microbiology, organic chemistry, analytical chemistry and nucleic acid chemistry described below are those well-known and commonly employed in the art. Such techniques are well-known and described in numerous texts and reference works well known to those of skill in the art. Standard techniques, or modifications thereof, are used for chemical syntheses and chemical analyses.

All patents, patent applications, articles and publications mentioned herein, both supra and infra, are hereby expressly incorporated herein by reference.

Although any suitable methods and materials similar or equivalent to those described herein find use in the practice of the present invention, some methods and materials are described herein. It is to be understood that this invention is not limited to the particular methodology, protocols, and reagents described, as these may vary, depending upon the context they are used by those of skill in the art. Accordingly, the terms defined immediately below are more fully described by reference to the application as a whole. All patents, patent applications, articles and publications mentioned herein, both supra and infra, are hereby expressly incorporated herein by reference.

As used herein, the singular "a", "an," and "the" include the plural references, unless the context clearly indicates otherwise.

Numeric ranges are inclusive of the numbers defining the range. Thus, every numerical range disclosed herein is intended to encompass every narrower numerical range that falls within such broader numerical range, as if such narrower numerical ranges were all expressly written herein. It is also intended that every maximum (or minimum) numerical limitation disclosed herein includes every lower (or higher) numerical limitation, as if such lower (or higher) numerical limitations were expressly written herein.

The term "about" means an acceptable error for a particular value. In some instances "about" means within 0.05%, 0.5%, 1.0%, or 2.0%, of a given value range. In some instances, "about" means within 1, 2, 3, or 4 standard deviations of a given value.

Furthermore, the headings provided herein are not limitations of the various aspects or embodiments of the invention which can be had by reference to the application as a whole. Accordingly, the terms defined immediately below are more fully defined by reference to the application as a whole. Nonetheless, in order to facilitate understanding of the invention, a number of terms are defined below.

Unless otherwise indicated, nucleic acids are written left to right in 5' to 3' orientation; amino acid sequences are written left to right in amino to carboxy orientation, respectively.

As used herein, the term "comprising" and its cognates are used in their inclusive sense (i.e., equivalent to the term "including" and its corresponding cognates).

As used herein, the "EC" number refers to the Enzyme Nomenclature of the Nomenclature Committee of the International Union of Biochemistry and Molecular Biology (NC-IUBMB). The IUBMB biochemical classification is a numerical classification system for enzymes based on the chemical reactions they catalyze.

As used herein, "ATCC" refers to the American Type Culture Collection whose biorepository collection includes genes and strains.

As used herein, "NCBI" refers to National Center for Biological Information and the sequence databases provided therein.

As used herein, the term "DNA" refers to deoxyribonucleic acid.

As used herein, the term "RNA" refers to ribonucleic acid.

As used herein, the terms "fusion protein," and "chimeric protein" and "chimera" refer to hybrid proteins created through the joining of two or more genes that originally encoded separate proteins. In some embodiments, fusion proteins are created by recombinant technology (e.g., molecular biology techniques known in the art).

As used herein, the term "ligase" refers to a class of enzymes that is commonly used to join polynucleotides together or to join the ends of a single polynucleotide. Ligases include ATP-dependent double-strand polynucleotide ligases, NAD⁺-dependent double-strand DNA or RNA ligases and single-strand polynucleotide ligases. In some embodiments, the present invention provides bacteriophage ligases (e.g., T3 DNA ligase, T4 DNA ligase, and T7 DNA ligase) and variants thereof. In some further embodiments, the present invention provides fusion or chimeric ligases. DNA ligases often find use with restriction enzymes for the insertion of DNA fragments (e.g., genes) into plasmids. For ligation of cohesive-ended fragments, controlling the optimal temperature is important in performing efficient recombination. T4 DNA ligase is most active at 37° C., but for optimal ligation efficiency with cohesive-ended fragments, the optimal temperature for the enzyme must be balanced with the melting temperature of the ends being ligated; the shorter the overhang, the lower the melting temperature of the fragments. Ligation reactions tend to be most efficient when the cohesive ends are already stably annealed. For ligation of blunt-ended DNA fragments, the melting temperature is not a factor to take into consideration when the reaction occurs within the normal temperature ranges used for ligation. In these reactions, the limiting factor is the number of alignments between DNA fragment ends that can occur, rather than the ligase activity. Thus, the most efficient temperature for ligation of blunt-ended DNA fragments is the temperature at which the greatest number of alignments can occur in the reaction.

As used herein, the term "adapter" refers to a single or double-stranded oligonucleotide with compatible DNA ends for ligation. The ends of an adapter may be single or double-stranded, and may contain overhangs compatible with complementary overhangs on processed library insert DNA. Adapters may have both single-stranded and double-stranded regions. In some embodiments, the term "adapter" is used to refer to full-length adapters used in NGS (i.e., next-generation sequencing) reactions which may include primer biding sites, barcodes and other features, as well as referring to simplified model adapters used in HTP screening and ligation assays, having the same ligation-compatible ends as full-length adapters, but lacking these additional features. NGS adapters designed for use on the Illumina® sequencing platform have deoxythymidine 3' overhangs compatible for ligation with deoxyadenosine 3' overhangs present on A-tailed insert fragments. T-tailed adapters are not efficiently ligated to one another due to the selectivity of wild-type T4 DNA ligase against non-complementary DNA ends. Adapter dimerization will occur as a result of extreme ligation conditions including long incubation periods, high adapter concentrations, or high concentrations of crowding agent. Importantly, nuclease contaminants in the ligation reaction can remove overhangs on the adaptor ends, resulting in blunt-ended substrates, which are compatible for self-ligation.

As used herein, the term "compatible ends" refers to the ends of two DNA duplex fragments with 5' or 3' overhangs that hybridize in a 5' to 3' antiparallel orientation, such that all bases on the overhangs are complementary. In the context of ligation, at least one DNA fragment must have a 5' phosphate on a nucleotide that is placed adjacent to a 3' hydroxyl of a nucleotide from another molecule upon hybridization of the 3' or 5' overhang. Ligation results in the covalent linkage of the two substrate molecules at the compatible ends. In some embodiments involving library preparation for DNA sequencing, two DNA molecules such as an adapter and an insert fragment must have compatible ends, and both strands of the adapter/insert hybrid must be ligated in order to enable productive library amplification via PCR or sequencing via polymerase extension of a primer hybridized to the adapter.

As used herein, the term "overhang" refers to a region of one or more unpaired polynucleotides occurring at the end of a double-stranded DNA fragment. Either a 5' or a 3' DNA end can be present in the unpaired region. The double-stranded DNA fragment can be a duplex of two complementary single-stranded polynucleotides, or it may be a single polynucleotide with self-complementarity that forms a region of double-stranded DNA.

As used herein, the terms "duplex" and "ds" refer to a double-stranded nucleic acid (e.g., DNA) molecule comprised of two single-stranded polynucleotides that are complementary in their sequence (A pairs to T, C pairs to G), arranged in an antiparallel 5' to 3' orientation, and held together by hydrogen bonds between the nucleobases (i.e., adenine [A], guanine [G], cytosine [C], and thymine [T]).

As used herein, the term "blunt" refers to the end of a DNA duplex or single-stranded ("ss") DNA with self-complementarity that does not have a 5' or 3' overhang. Blunt ends may have 5' phosphates on one or both strands, which make them compatible for ligation via a ligase such as T4 DNA ligase.

As used herein, the term "adapter dimer" refers to any covalent ligation product between two adapters. Adapter dimers may formed during ligation reactions.

As used herein, the terms "library insert" and "insert" refer to a double-stranded DNA fragment that has been processed via end repair and/or A-tailing to present compatible ends for use in adapter ligation.

As used herein, the term "end repair" refers to methods for repairing DNA (e.g., fragmented or damaged DNA or DNA molecules that are incompatible with other DNA molecules). In some embodiments, the process involves two functions: 1) conversion of double-stranded DNA with overhangs to double-stranded DNA without overhangs by an enzyme such as T4 DNA polymerase and/or Klenow fragment; and 2) addition of a phosphate group to the 5' ends of DNA (single- or double-stranded), by an enzyme such as polynucleotide kinase.

As used herein, the term "A-tailing" refers to the addition of a single deoxyadenosine residue to the end of a blunt-ended double-stranded DNA fragment to form a 3' deoxyadenosine single-base overhang. A-tailed fragments are not compatible for self-ligation (i.e., self-circularization and concantenation of the DNA), but they are compatible with 3' deoxythymidine-overhangs such as those present on adapters.

As used herein, the term "amino blocked" refers to a single- or double-stranded DNA end for which the 3' hydroxyl has been replaced by a 6-carbon linker terminating in an amino moiety. DNA ligases cannot catalyze ligation reactions in the absence of the 3' hydroxyl.

"Protein," "polypeptide," and "peptide" are used interchangeably herein to denote a polymer of at least two amino acids covalently linked by an amide bond, regardless of length or post-translational modification (e.g., glycosylation or phosphorylation).

"Amino acids" are referred to herein by either their commonly known three-letter symbols or by the one-letter symbols recommended by IUPAC-IUB Biochemical Nomenclature Commission. Nucleotides, likewise, may be referred to by their commonly accepted single letter codes.

The terms "engineered," "recombinant," "non-naturally occurring," and "variant," when used with reference to a cell, a polynucleotide or a polypeptide refers to a material or a material corresponding to the natural or native form of the material that has been modified in a manner that would not otherwise exist in nature or is identical thereto but produced or derived from synthetic materials and/or by manipulation using recombinant techniques.

As used herein, "wild-type" and "naturally-occurring" refer to the form found in nature. For example a wild-type polypeptide or polynucleotide sequence is a sequence present in an organism that can be isolated from a source in nature and which has not been intentionally modified by human manipulation.

As used herein, "coding sequence" refers to that part of a nucleic acid (e.g., a gene) that encodes an amino acid sequence of a protein.

As used herein, the term "percent (%) sequence identity" refers to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman (Smith and Waterman, Adv. Appl. Math., 2:482 [1981]), by the homology alignment algorithm of Needleman and Wunsch (Needleman and Wunsch, J. Mol. Biol., 48:443 [1970]), by the search for similarity method of Pearson and Lipman (Pearson and Lipman, Proc. Natl. Acad. Sci. USA 85:2444 [1988]), by computerized implementations of these algorithms (e.g., GAP, BESTFIT, FASTA, and TFASTA in the GCG Wisconsin Software Package), or by visual inspection, as known in the art. Examples of algorithms that are suitable for determining percent sequence identity and sequence similarity include, but are not limited to the BLAST and BLAST 2.0 algorithms (See e.g., Altschul et al., J. Mol. Biol., 215: 403-410 [1990]; and Altschul et al., Nucleic Acids Res., 3389-3402 [1977]). Software for performing BLAST analyses is publicly available through the National Center for Biotechnology Information website. This algorithm involves first identifying high scoring sequence pairs (HSPs) by identifying short words of length "W" in the query sequence, which either match or satisfy some positive-valued threshold score "T," when aligned with a word of the same length in a database sequence. T is referred to as the neighborhood word score threshold (See, Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters "M" (reward score for a pair of matching residues; always >0) and "N" (penalty score for mismatching residues; always <0). For amino acid sequences, a scoring matrix is used to calculate the cumulative score. Extension of the word hits in each direction are halted when: the cumulative alignment score falls off by the quantity "X" from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (See e.g., Henikoff and Henikoff, Proc. Natl. Acad. Sci. USA 89:10915 [1989]). Exemplary determination of sequence alignment and % sequence identity can employ the BESTFIT or GAP programs in the GCG Wisconsin Software package (Accelrys, Madison WI), using default parameters provided.

As used herein, "reference sequence" refers to a defined sequence used as a basis for a sequence comparison. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, at least 100 residues in length or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides or polypeptides over a "comparison window" to identify and compare local regions of sequence similarity. In some embodiments, a "reference sequence" can be based on a primary amino acid sequence, where the reference sequence is a sequence that can have one or more changes in the primary sequence. For instance, the phrase "a reference sequence based on SEQ ID NO: 4, having a valine at the residue corresponding to X39" refers to a reference sequence in which the corresponding residue at position X39 in SEQ ID NO: 4 (e.g., an alanine), has been changed to valine.

As used herein, "comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

As used herein, "corresponding to", "reference to," and "relative to" when used in the context of the numbering of a given amino acid or polynucleotide sequence refer to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered ligase, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned. In some embodiments, the sequence is tagged (e.g., with a histidine tag).

As used herein, "amino acid difference" and "residue difference" refer to a difference in the amino acid residue at a position of a polypeptide sequence relative to the amino acid residue at a corresponding position in a reference sequence. The positions of amino acid differences generally are referred to herein as "Xn," where n refers to the corresponding position in the reference sequence upon which the residue difference is based. For example, a "residue difference at position X91 as compared to SEQ ID NO: 4" refers to a difference of the amino acid residue at the polypeptide position corresponding to position 91 of SEQ ID NO: 4. Thus, if the reference polypeptide of SEQ ID NO: 4 has a alanine at position 91, then a "residue difference at position X91 as compared to SEQ ID NO: 4" refers to an amino acid substitution of any residue other than alanine at the position of the polypeptide corresponding to position 91 of SEQ ID NO: 4. In most instances herein, the specific amino acid residue difference at a position is indicated as "XnY" where "Xn" specified the corresponding residue and position of the reference polypeptide (as described above), and "Y" is the single letter identifier of the amino acid found in the engineered polypeptide (i.e., the different residue than in the reference polypeptide). In some instances (e.g., in the Tables in the Examples), the present disclosure also provides specific amino acid differences denoted by the conventional notation "AnB", where A is the single letter identifier of the residue in the reference sequence, "n" is the number of the residue position in the reference sequence, and B is the single letter identifier of the residue substitution in the sequence of the engineered polypeptide. In some instances, a polypeptide of the present disclosure can include one or more amino acid residue differences relative to a reference sequence, which is indicated by a list of the specified positions where residue differences are present relative to the reference sequence. In some embodiments, where more than one amino acid can be used in a specific residue position of a polypeptide, the various amino acid residues that can be used are separated by a "/" (e.g., X307G/X307Q or X307G/Q). The present disclosure includes engineered polypeptide sequences comprising one or more amino acid differences that include either/or both conservative and non-conservative amino acid substitutions.

As used herein, the terms "amino acid substitution set" and "substitution set" refers to a group of amino acid substitutions within a polypeptide sequence. In some embodiments, substitution sets comprise 1, 2, 3, 4, 5, 6, 7, 8, 9, 10, 11, 12, 13, 14, 15, or more amino acid substitutions. In some embodiments, a substitution set refers to the set of amino acid substitutions that is present in any of the variant ligase polypeptides listed in any of the Tables in the Examples. In these substitution sets, the individual substitutions are separated by a semicolon (";"; e.g., C165A; S181T;K299P) or slash ("/"; e.g., C165A/S181T/K299P).

As used herein, "conservative amino acid substitution" refers to a substitution of a residue with a different residue having a similar side chain, and thus typically involves substitution of the amino acid in the polypeptide with amino acids within the same or similar defined class of amino acids. By way of example and not limitation, an amino acid with an aliphatic side chain may be substituted with another aliphatic amino acid (e.g., alanine, valine, leucine, and isoleucine); an amino acid with hydroxyl side chain is substituted with another amino acid with a hydroxyl side chain (e.g., serine and threonine); an amino acids having aromatic side chains is substituted with another amino acid having an aromatic side chain (e.g., phenylalanine, tyrosine, tryptophan, and histidine); an amino acid with a basic side chain is substituted with another amino acid with a basis side chain (e.g., lysine and arginine); an amino acid with an acidic side chain is substituted with another amino acid with an acidic side chain (e.g., aspartic acid or glutamic acid); and a hydrophobic or hydrophilic amino acid is replaced with another hydrophobic or hydrophilic amino acid, respectively.

As used herein, "non-conservative substitution" refers to substitution of an amino acid in the polypeptide with an amino acid with significantly differing side chain properties. Non-conservative substitutions may use amino acids between, rather than within, the defined groups and affect: (a) the structure of the peptide backbone in the area of the substitution (e.g., proline for glycine); (b) the charge or hydrophobicity; and/or (c) the bulk of the side chain. By way of example and not limitation, exemplary non-conservative substitutions include an acidic amino acid substituted with a basic or aliphatic amino acid; an aromatic amino acid substituted with a small amino acid; and a hydrophilic amino acid substituted with a hydrophobic amino acid.

As used herein, "deletion" refers to modification to the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the reference enzyme while retaining enzymatic activity and/or retaining the improved properties of an engineered transaminase enzyme. Deletions can be directed to the internal portions and/or terminal portions of the polypeptide. In various embodiments, the deletion can comprise a continuous segment or can be discontinuous.

As used herein, "insertion" refers to modification to the polypeptide by addition of one or more amino acids from the reference polypeptide. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

As used herein, "functional fragment" and "biologically active fragment" are used interchangeably herein, to refer to a polypeptide that has an amino-terminal and/or carboxy-terminal deletion(s) and/or internal deletions, but where the remaining amino acid sequence is identical to the corresponding positions in the sequence to which it is being compared (e.g., a full length engineered ligase of the present invention) and that retains substantially all of the activity of the full-length polypeptide.

As used herein, "isolated polypeptide" refers to a polypeptide which is substantially separated from other contaminants that naturally accompany it (e.g., protein, lipids, and polynucleotides). The term embraces polypeptides which have been removed or purified from their naturally-occurring environment or expression system (e.g., host cell or in vitro synthesis). The recombinant ligase polypeptides may be present within a cell, present in the cellular medium, or prepared in various forms, such as lysates or isolated preparations. As such, in some embodiments, the recombinant ligase polypeptides provided herein are isolated polypeptides.

As used herein, "substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure ligase composition will comprise about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species. In some embodiments, the isolated recombinant ligase polypeptides are substantially pure polypeptide compositions.

As used herein, "improved enzyme property" refers to an engineered ligase polypeptide that exhibits an improvement in any enzyme property as compared to a reference ligase polypeptide, such as a wild-type ligase polypeptide (e.g., the wild-type T4 ligase of SEQ ID NO: 2) or another engineered ligase polypeptide. Improved properties include but are not limited to such properties as increased protein expression, increased thermoactivity, increased thermostability, increased stability, increased enzymatic activity, increased substrate specificity and/or affinity, increased specific activity, increased resistance to substrate and/or end-product inhibition, increased chemical stability, improved chemoselectivity, improved solvent stability, increased tolerance to acidic pH, increased tolerance to proteolytic activity (i.e., reduced sensitivity to proteolysis), increased solubility, and altered temperature profile.

As used herein, "increased enzymatic activity" and "enhanced catalytic activity" refer to an improved property of the engineered ligase polypeptides, which can be represented by an increase in specific activity (e.g., product produced/time/weight protein) and/or an increase in percent conversion of the substrate to the product (e.g., percent conversion of starting amount of substrate to product in a specified time period using a specified amount of ligase) as compared to the reference ligase enzyme (e.g., wild-type T4 ligase and/or another engineered ligase). Exemplary methods to determine enzyme activity are provided in the Examples. Any property relating to enzyme activity may be affected, including the classical enzyme properties of $K_m$, $V_{max}$ or $k_{cat}$, changes of which can lead to increased enzymatic activity. Improvements in enzyme activity can be from about 1.1 fold the enzymatic activity of the corresponding wild-type enzyme, to as much as 2-fold, 5-fold, 10-fold, 20-fold, 25-fold, 50-fold, 75-fold, 100-fold, 150-fold, 200-fold or more enzymatic activity than the naturally occurring ligase or another engineered ligase from which the ligase polypeptides were derived.

The terms "proteolytic activity" and "proteolysis" used interchangeably herein refer to the breakdown of proteins into smaller polypeptides or amino acids. The breakdown of proteins is generally the result of hydrolysis of the peptide bond by protease (proteinase) enzymes. Protease enzymes include but are not limited to pepsin, trypsin, chymotrypsin, elastase; carboxypeptidase A and B, and peptidases (e.g., amino peptidase, dipeptidase and enteropeptidase).

The phrases "reducing sensitivity to proteolysis" and "reducing proteolytic sensitivity" are used interchangeably herein mean that an engineered ligase polypeptide according to the invention will have a higher enzyme activity compared to a reference ligase in a standard assay (e.g., as disclosed in the Examples) after treatment with one or more proteases.

As used herein, "conversion" refers to the enzymatic conversion (or biotransformation) of substrate(s) to the corresponding product(s). "Percent conversion" refers to the percent of the substrate that is converted to the product within a period of time under specified conditions. Thus, the "enzymatic activity" or "activity" of a ligase polypeptide can be expressed as "percent conversion" of the substrate to the product in a specific period of time.

As used herein, "hybridization stringency" relates to hybridization conditions, such as washing conditions, in the hybridization of nucleic acids. Generally, hybridization reactions are performed under conditions of lower stringency, followed by washes of varying but higher stringency. The term "moderately stringent hybridization" refers to conditions that permit target-DNA to bind a complementary nucleic acid that has about 60% identity, preferably about 75% identity, about 85% identity to the target DNA, with greater than about 90% identity to target-polynucleotide. Exemplary moderately stringent conditions are conditions equivalent to hybridization in 50% formamide, 5× Denhart's solution, 5×SSPE, 0.2% SDS at 42° C., followed by washing in 0.2×SSPE, 0.2% SDS, at 42° C. "High stringency hybridization" refers generally to conditions that are about 10° C. or less from the thermal melting temperature $T_m$ as determined under the solution condition for a defined polynucleotide sequence. In some embodiments, a high stringency condition refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in conditions equivalent to 50% formamide, 5× Denhart's solution, 5×SSPE, 0.2% SDS at 42° C., followed by washing in 0.1×SSPE, and 0.1% SDS at 65° C. Another high stringency condition is hybridizing in conditions equivalent to hybridizing in 5×SSC containing 0.1% (w:v) SDS at 65° C. and washing in 0.1×SSC containing 0.1%

SDS at 65° C. Other high stringency hybridization conditions, as well as moderately stringent conditions, are described in the references cited above.

As used herein, "codon optimized" refers to changes in the codons of the polynucleotide encoding a protein to those preferentially used in a particular organism such that the encoded protein is more efficiently expressed in that organism. Although the genetic code is degenerate, in that most amino acids are represented by several codons, called "synonyms" or "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome. In some embodiments, the polynucleotides encoding the ligase enzymes are codon optimized for optimal production from the host organism selected for expression.

As used herein, "control sequence" refers herein to include all components that are necessary or advantageous for the expression of a polynucleotide and/or polypeptide of the present disclosure. Each control sequence may be native or foreign to the nucleic acid sequence encoding the polypeptide. Such control sequences include, but are not limited to, leaders, polyadenylation sequences, propeptide sequences, promoter sequences, signal peptide sequences, initiation sequences, and transcription terminators. At a minimum, the control sequences include a promoter, and transcriptional and translational stop signals. In some embodiments, the control sequences are provided with linkers for the purpose of introducing specific restriction sites facilitating ligation of the control sequences with the coding region of the nucleic acid sequence encoding a polypeptide.

"Operably linked" is defined herein as a configuration in which a control sequence is appropriately placed (i.e., in a functional relationship) at a position relative to a polynucleotide of interest such that the control sequence directs or regulates the expression of the polynucleotide encoding a polypeptide of interest.

As used herein, "promoter sequence" refers to a nucleic acid sequence that is recognized by a host cell for expression of a polynucleotide of interest, such as a coding sequence. The promoter sequence contains transcriptional control sequences that mediate the expression of a polynucleotide of interest. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

As used herein, "suitable reaction conditions" refers to those conditions in the enzymatic conversion reaction solution (e.g., ranges of enzyme loading, substrate loading, temperature, pH, buffers, co-solvents, etc.) under which a ligase polypeptide of the present disclosure is capable of converting a substrate to the desired product compound, Exemplary "suitable reaction conditions" are provided herein (See, the Examples).

As used herein, "loading", such as in "compound loading" or "enzyme loading" refers to the concentration or amount of a component in a reaction mixture at the start of the reaction. "Substrate" in the context of an enzymatic conversion reaction process refers to the compound or molecule acted on by the ligase polypeptide.

As used herein, "product" in the context of an enzymatic conversion process refers to the compound or molecule resulting from the action of the ligase polypeptide on the substrate.

As used herein, "culturing" refers to the growing of a population of microbial cells under suitable conditions using any suitable medium (e.g., liquid, gel, or solid).

Recombinant polypeptides (e.g., ligase enzyme variants) can be produced using any suitable methods known the art. For example, there is a wide variety of different mutagenesis techniques well known to those skilled in the art. In addition, mutagenesis kits are also available from many commercial molecular biology suppliers. Methods are available to make specific substitutions at defined amino acids (site-directed), specific or random mutations in a localized region of the gene (regio-specific), or random mutagenesis over the entire gene (e.g., saturation mutagenesis). Numerous suitable methods are known to those in the art to generate enzyme variants, including but not limited to site-directed mutagenesis of single-stranded DNA or double-stranded DNA using PCR, cassette mutagenesis, gene synthesis, error-prone PCR, shuffling, and chemical saturation mutagenesis, or any other suitable method known in the art. Non-limiting examples of methods used for DNA and protein engineering are provided in the following patents: U.S. Pat. Nos. 6,117,679; 6,420,175; 6,376,246; 6,586,182; 7,747,391; 7,747,393; 7,783,428; and 8,383,346. After the variants are produced, they can be screened for any desired property (e.g., high or increased activity, or low or reduced activity, increased thermal activity, increased thermal stability, and/or acidic pH stability, etc.). In some embodiments, "recombinant ligase polypeptides" (also referred to herein as "engineered ligase polypeptides," "variant ligase enzymes," and "ligase variants") find use.

As used herein, a "vector" is a DNA construct for introducing a DNA sequence into a cell. In some embodiments, the vector is an expression vector that is operably linked to a suitable control sequence capable of effecting the expression in a suitable host of the polypeptide encoded in the DNA sequence. In some embodiments, an "expression vector" has a promoter sequence operably linked to the DNA sequence (e.g., transgene) to drive expression in a host cell, and in some embodiments, also comprises a transcription terminator sequence.

As used herein, the term "expression" includes any step involved in the production of the polypeptide including, but not limited to, transcription, post-transcriptional modification, translation, and post-translational modification. In some embodiments, the term also encompasses secretion of the polypeptide from a cell.

As used herein, the term "produces" refers to the production of proteins and/or other compounds by cells. It is intended that the term encompass any step involved in the production of polypeptides including, but not limited to, transcription, post-transcriptional modification, translation, and post-translational modification. In some embodiments, the term also encompasses secretion of the polypeptide from a cell.

As used herein, an amino acid or nucleotide sequence (e.g., a promoter sequence, signal peptide, terminator sequence, etc.) is "heterologous" to another sequence with which it is operably linked if the two sequences are not associated in nature.

As used herein, the terms "host cell" and "host strain" refer to suitable hosts for expression vectors comprising DNA provided herein (e.g., a polynucleotide sequences encoding at least one ligase variant). In some embodiments, the host cells are prokaryotic or eukaryotic cells that have been transformed or transfected with vectors constructed using recombinant DNA techniques as known in the art.

As used herein, the term "analogue" means a polypeptide having more than 70% sequence identity but less than 100% sequence identity (e.g., more than 75%, 78%, 80%, 83%, 85%, 88%, 90%, 91%, 92%, 93%, 94%, 95%, 96%, 97%, 98%, 99% sequence identity) with a reference polypeptide. In some embodiments, analogues include non-naturally occurring amino acid residues including, but not limited, to homoarginine, ornithine and norvaline, as well as naturally occurring amino acids. In some embodiments, analogues also include one or more D-amino acid residues and non-peptide linkages between two or more amino acid residues.

As used herein, the term "effective amount" means an amount sufficient to produce the desired result. One of general skill in the art may determine what the effective amount by using routine experimentation.

The terms "isolated" and "purified" are used to refer to a molecule (e.g., an isolated nucleic acid, polypeptide, etc.) or other component that is removed from at least one other component with which it is naturally associated. The term "purified" does not require absolute purity, rather it is intended as a relative definition.

The term "subject" encompasses mammals such as humans, non-human primates, livestock, companion animals, and laboratory animals (e.g., rodents and lagamorphs). It is intended that the term encompass females as well as males.

As used herein, the term "patient" means any subject that is being assessed for, treated for, or is experiencing disease.

As used herein, "composition" and "formulation" encompass products comprising at least one As used herein, "cell-free DNA" refers to DNA circulating freely in the bloodstream and is not contained by or associated with cells. In some embodiments, cell-free DNA comprises DNA originally derived and released from normal somatic or germ line cells, cancer cells, fetal cells, microbial cells, or viruses.

As used herein, "index hopping" refers to a process whereby sequencing reads are incorrectly assigned to libraries labeled with an index from another library. Index hopping may occur when unligated adapter molecules are not efficiently removed during library cleanup, and are then incorporated into library fragments at later steps into the sequencing workflow.

Engineered Ligase Polypeptides:

When a particular ligase variant (i.e., an engineered ligase polypeptide) is referred to by reference to modification of particular amino acids residues in the sequence of a wild-type ligase or reference ligase, it is to be understood that variants of another ligase modified in the equivalent position(s) (as determined from the optional amino acid sequence alignment between the respective amino acid sequences) are encompassed herein.

The engineered ligase polypeptide variants of the present invention perform single-end ligation capture in plate-capture high throughput assays at a much higher rate that wild-type T4 DNA ligase, as indicated in the Examples. Furthermore, these variant ligases are capable of performing the ligation reactions in the absence of agents such as PEG. In addition, these ligase variants exhibit increased inhibitor tolerance.

The engineered ligase variants of the present invention efficiently create DNA libraries suitable for NGS and other diagnostic methods. These ligase variants find use in solution, as well as in immobilized embodiments.

In some additional embodiments, the engineered ligase polypeptide of the present invention comprises a polypeptide comprising at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 2, 6, 32, 34, and/or 38.

In some embodiments, engineered ligase polypeptides are produced by cultivating a microorganism comprising at least one polynucleotide sequence encoding at least one engineered ligase polypeptide under conditions which are conducive for producing the engineered ligase polypeptide. In some embodiments, the engineered ligase polypeptide is subsequently recovered from the resulting culture medium and/or cells.

The present invention provides exemplary engineered ligase polypeptides having ligase activity. The Examples provide Tables showing sequence structural information correlating specific amino acid sequence features with the functional activity of the engineered ligase polypeptides. This structure-function correlation information is provided in the form of specific amino acid residue differences relative to the reference engineered polypeptide of SEQ ID NO: 2, 6, 32, 34, and/or 38, as well as associated experimentally determined activity data for the exemplary engineered ligase polypeptides.

In some embodiments, the engineered ligase polypeptides of the present invention having ligase activity comprise an amino acid sequence having at least 85% sequence identity to reference sequence SEQ ID NO: 2, 6, 32, 34, and/or 38, and which exhibits at least one improved property, as compared to the reference sequence (e.g., wild-type T4 DNA ligase).

In some embodiments the engineered ligase polypeptides exhibiting at least one improved property have at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO: 2, 6, 32, 34, and/or 38, and an amino acid residue difference at one or more amino acid positions (such as at 1, 2, 3, 4, 5, 6, 7, 8, 9, 10, 11, 12, 14, 15, 20 or more amino acid positions) compared to SEQ ID NO: 2, 6, 32, 34, and/or 38. In some embodiments, the engineered ligase polypeptide is a polypeptide listed in the Tables provided in the Examples.

In some embodiments, the present invention provides functional fragments of engineered ligase polypeptides. In some embodiments, functional fragments comprise at least about 90%, at least about 95%, at least about 96%, at least about 97%, at least about 98%, or at least about 99% of the activity of the engineered ligase polypeptide from which it was derived (i.e., the parent engineered ligase). In some embodiments, functional fragments comprise at least about 90%, at least about 91%, at least about 92%, at least about 93%, at least about 94%, at least about 95%, at least about 96%, at least about 97%, at least about 98%, or at least about 99% of the parent sequence of the engineered ligase. In some embodiments the functional fragment will be truncated by less than 5, less than 10, less than 15, less than 10, less than 25, less than 30, less than 35, less than 40, less than 45, and less than 50 amino acids.

In some embodiments, the present invention provides functional fragments of engineered ligase polypeptides. In some embodiments, functional fragments comprise at least about 95%, 96%, 97%, 98%, or 99% of the activity of the engineered ligase polypeptide from which it was derived (i.e., the parent engineered ligase). In some embodiments, functional fragments comprise at least 90%, 91%, 92%, 93%, 94%, 95%, 96%, 97%, 98%, or 99% of the parent sequence of the engineered ligase. In some embodiments the functional fragment will be truncated by less than 5, less than 10, less than 15, less than 10, less than 25, less than 30, less than 35, less than 40, less than 45, less than 50, less than 55, less than 60, less than 65, or less than 70 amino acids.

In some embodiments, the engineered ligase polypeptides exhibiting at least one improved property have at least 85%, at least 88%, at least 90%, at least 91%, at least 92%, at least 93%, at least 94%, at least 95%, at least 96%, at least 97%, at least 98%, at least 99%, or greater amino acid sequence identity with SEQ ID NO: 2, 6, 32, 34, and/or 38, and an amino acid residue difference at one or more amino acid positions (such as at 1, 2, 3, 4, 5, 6, 7, 8, 9, 10, 11, 12, 14, 15 or more amino acid positions) compared to SEQ ID NO: 2, 6, 32, 34, and/or 38. In some embodiments, the engineered ligases comprise at least 90% sequence identity to SEQ ID NO: 2, 6, 32, 34, and/or 38, and comprise an amino acid difference of at least 1, 2, 3, 4, 5, 6, 7, 8, 9, 10 or more amino acid positions. In some embodiments, the engineered ligase polypeptide consists of the sequence of SEQ ID NO: 6, 32, 34, and/or 38.

Polynucleotides Encoding Engineered Polypeptides, Expression Vectors and Host Cells:

The present invention provides polynucleotides encoding the engineered ligase polypeptides described herein. In some embodiments, the polynucleotides are operatively linked to one or more heterologous regulatory sequences that control gene expression to create a recombinant polynucleotide capable of expressing the polypeptide. In some embodiments, expression constructs containing at least one heterologous polynucleotide encoding the engineered ligase polypeptide(s) is introduced into appropriate host cells to express the corresponding ligase polypeptide(s).

As will be apparent to the skilled artisan, availability of a protein sequence and the knowledge of the codons corresponding to the various amino acids provide a description of all the polynucleotides capable of encoding the subject polypeptides. The degeneracy of the genetic code, where the same amino acids are encoded by alternative or synonymous codons, allows an extremely large number of nucleic acids to be made, all of which encode an engineered ligase polypeptide. Thus, the present invention provides methods and compositions for the production of each and every possible variation of ligase polynucleotides that could be made that encode the ligase polypeptides described herein by selecting combinations based on the possible codon choices, and all such variations are to be considered specifically disclosed for any polypeptide described herein, including the amino acid sequences presented in the Examples (e.g., in the various Tables).

In some embodiments, the codons are preferably optimized for utilization by the chosen host cell for protein production. For example, preferred codons used in bacteria are typically used for expression in bacteria. Consequently, codon optimized polynucleotides encoding the engineered ligase polypeptides contain preferred codons at about 40%, 50%, 60%, 70%, 80%, 90%, or greater than 90% of the codon positions in the full length coding region.

In some embodiments, the ligase polynucleotide encodes an engineered polypeptide having ligase activity with the properties disclosed herein, wherein the polypeptide comprises an amino acid sequence having at least 80%, 85%, 86%, 87%, 88%, 89%, 90%, 91%, 92%, 93%, 94%, 95%, 96%, 97%, 98%, 99% or more identity to a reference sequence selected from SEQ ID NOS: 2, 6, 32, 34, and/or 38, or the amino acid sequence of any variant (e.g., those provided in the Examples), and one or more residue differences as compared to the reference polynucleotide of SEQ ID NOs: 2, 6, 32, 34, and/or 38, or the amino acid sequence of any variant as disclosed in the Examples (for example 1, 2, 3, 4, 5, 6, 7, 8, 9, 10 or more amino acid residue positions). In some embodiments, the reference sequence is selected from SEQ ID NOS: 2, 6, 32, 34, and/or 38. In some embodiments, the engineered ligase variants comprise a polypeptide sequence set forth in SEQ ID NO: 32, 34, 36, 38, 40, 42, 44, 46, 48, 50, 52, and/or 54. In some embodiments, the engineered ligase variants comprise the substitution(s) or substitution set(s) of variant ligases 1 through 261, as provided in the Examples (e.g., Tables 4,1, 4.2, 4.3, 5.1, 5.2, 5.3, 5.4, 5.5, and 6.1).

The present invention provides polynucleotides encoding the engineered ligase variants provided herein. In some embodiments, the polynucleotides comprise a nucleotide sequence having at least 80%, 85%, 86%, 87%, 88%, 89%, 90%, 91%, 92%, 93%, 94%, 95%, 96%, 97%, 98%, 99% or more identity to a reference sequence selected from SEQ ID NOS: 1, 5, 31, 33, and/or 37, or the amino acid sequence of any variant (e.g., those provided in the Examples), and one or more residue differences as compared to the reference polynucleotide of SEQ ID NOs: 1, 5, 31, 37, and/or 38, or the amino acid sequence of any variant as disclosed in the Examples (for example 1, 2, 3, 4, 5, 6, 7, 8, 9, 10 or more amino acid residue positions). In some embodiments, the reference sequence is selected from SEQ ID NOS: 1, 5, 31, 33, and/or 37. In some embodiments, the polynucleotides are capable of hybridizing under highly stringent conditions to a reference polynucleotide sequence selected from SEQ ID NOS: 1, 5, 31, 33, and/or 37, or a complement thereof, or a polynucleotide sequence encoding any of the variant ligase polypeptides provided herein. In some embodiments, the polynucleotide capable of hybridizing under highly stringent conditions encodes a ligase polypeptide comprising an amino acid sequence that has one or more residue differences as compared to SEQ ID NO: 2, 6, 32, 34, and/or 38. In some embodiments, the engineered ligase variants are encoded by a polynucleotide sequence set forth in SEQ ID NO: 31, 33, 35, 37, 39, 41, 43, 45, 47, 49, 51, and/or 53.

In some embodiments, an isolated polynucleotide encoding any of the engineered ligase polypeptides herein is manipulated in a variety of ways to facilitate expression of the ligase polypeptide. In some embodiments, the polynucleotides encoding the ligase polypeptides comprise expression vectors where one or more control sequences is present to regulate the expression of the ligase polynucleotides and/or polypeptides. Manipulation of the isolated polynucleotide prior to its insertion into a vector may be desirable or necessary depending on the expression vector utilized. Techniques for modifying polynucleotides and nucleic acid sequences utilizing recombinant DNA methods are well known in the art. In some embodiments, the control sequences include among others, promoters, leader sequences, polyadenylation sequences, propeptide sequences, signal peptide sequences, and transcription terminators. In some embodiments, suitable promoters are selected based on the host cells selection. For bacterial host cells, suitable promoters for directing transcription of the nucleic acid constructs of the present disclosure, include, but are not limited to promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothennophilus* maltogenic amylase gene (amyM), *Bacillus amyloliquefa-*

*ciens* alpha-amylase gene (amyQ), *Bacillus lichenifonnis* penicillinase gene (penP), *Bacillus subtilis* xylA and xylB genes, and prokaryotic beta-lactamase gene (See e.g., Villa-Kamaroff et al., Proc. Natl Acad. Sci. USA 75: 3727-3731 [1978]), as well as the tac promoter (See e.g., DeBoer et al., Proc. Natl Acad. Sci. USA 80: 21-25 [1983]). Exemplary promoters for filamentous fungal host cells, include, but are not limited to promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (See e.g., WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof. Exemplary yeast cell promoters can be from the genes can be from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are known in the art (See e.g., Romanos et al., Yeast 8:423-488 [1992]).

In some embodiments, the control sequence is also a suitable transcription terminator sequence (i.e., a sequence recognized by a host cell to terminate transcription). In some embodiments, the terminator sequence is operably linked to the 3' terminus of the nucleic acid sequence encoding the ligase polypeptide. Any suitable terminator which is functional in the host cell of choice finds use in the present invention. Exemplary transcription terminators for filamentous fungal host cells can be obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease. Exemplary terminators for yeast host cells can be obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are known in the art (See e.g., Romanos et al., supra).

In some embodiments, the control sequence is also a suitable leader sequence (i.e., a non-translated region of an mRNA that is important for translation by the host cell). In some embodiments, the leader sequence is operably linked to the 5' terminus of the nucleic acid sequence encoding the ligase polypeptide. Any suitable leader sequence that is functional in the host cell of choice find use in the present invention. Exemplary leaders for filamentous fungal host cells are obtained from the genes for *Aspergillus oryzae* TAKA amylase, and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

In some embodiments, the control sequence is also a polyadenylation sequence (i.e., a sequence operably linked to the 3' terminus of the nucleic acid sequence and which, when transcribed, is recognized by the host cell as a signal to add polyadenosine residues to transcribed mRNA). Any suitable polyadenylation sequence which is functional in the host cell of choice finds use in the present invention. Exemplary polyadenylation sequences for filamentous fungal host cells include, but are not limited to the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase. Useful polyadenylation sequences for yeast host cells are known (See e.g., Guo and Sherman, Mol. Cell. Bio., 15:5983-5990 [1995]).

In some embodiments, the control sequence is also a signal peptide (i.e., a coding region that codes for an amino acid sequence linked to the amino terminus of a polypeptide and directs the encoded polypeptide into the cell's secretory pathway). In some embodiments, the 5' end of the coding sequence of the nucleic acid sequence inherently contains a signal peptide coding region naturally linked in translation reading frame with the segment of the coding region that encodes the secreted polypeptide. Alternatively, in some embodiments, the 5' end of the coding sequence contains a signal peptide coding region that is foreign to the coding sequence. Any suitable signal peptide coding region which directs the expressed polypeptide into the secretory pathway of a host cell of choice finds use for expression of the engineered polypeptide(s). Effective signal peptide coding regions for bacterial host cells are the signal peptide coding regions include, but are not limited to those obtained from the genes for *Bacillus* NC1B 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are known in the art (See e.g., Simonen and Palva, Microbiol. Rev., 57:109-137 [1993]). In some embodiments, effective signal peptide coding regions for filamentous fungal host cells include, but are not limited to the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase. Useful signal peptides for yeast host cells include, but are not limited to those from the genes for *Saccharomyces cerevisiae* alpha-factor and *Saccharomyces cerevisiae* invertase.

In some embodiments, the control sequence is also a propeptide coding region that codes for an amino acid sequence positioned at the amino terminus of a polypeptide. The resultant polypeptide is referred to as a "proenzyme," "propolypeptide," or "zymogen." A propolypeptide can be converted to a mature active polypeptide by catalytic or autocatalytic cleavage of the propeptide from the propolypeptide. The propeptide coding region may be obtained from any suitable source, including, but not limited to the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* lactase (See e.g., WO 95/33836). Where both signal peptide and propeptide regions are present at the amino terminus of a polypeptide, the propeptide region is positioned next to the amino terminus of a polypeptide and the signal peptide region is positioned next to the amino terminus of the propeptide region.

In some embodiments, regulatory sequences are also utilized. These sequences facilitate the regulation of the expression of the polypeptide relative to the growth of the host cell. Examples of regulatory systems are those that cause the expression of the gene to be turned on or off in response to a chemical or physical stimulus, including the presence of a regulatory compound. In prokaryotic host cells, suitable regulatory sequences include, but are not limited to the lac, tac, and trp operator systems. In yeast host cells, suitable regulatory systems include, but are not limited to the ADH2 system or GAL1 system. In filamentous fungi, suitable regulatory sequences include, but are not limited to the TAKA alpha-amylase promoter, *Aspergillus niger* glucoamylase promoter, and *Aspergillus oryzae* glucoamylase promoter.

In another aspect, the present invention is directed to a recombinant expression vector comprising a polynucleotide encoding an engineered ligase polypeptide, and one or more expression regulating regions such as a promoter and a terminator, a replication origin, etc., depending on the type of hosts into which they are to be introduced. In some embodiments, the various nucleic acid and control sequences described herein are joined together to produce recombinant expression vectors which include one or more convenient restriction sites to allow for insertion or substitution of the nucleic acid sequence encoding the ligase polypeptide at such sites. Alternatively, in some embodiments, the nucleic acid sequence of the present invention is expressed by inserting the nucleic acid sequence or a nucleic acid construct comprising the sequence into an appropriate vector for expression. In some embodiments involving the creation of the expression vector, the coding sequence is located in the vector so that the coding sequence is operably linked with the appropriate control sequences for expression.

The recombinant expression vector may be any suitable vector (e.g., a plasmid or virus), that can be conveniently subjected to recombinant DNA procedures and bring about the expression of the ligase polynucleotide sequence. The choice of the vector typically depends on the compatibility of the vector with the host cell into which the vector is to be introduced. The vectors may be linear or closed circular plasmids.

In some embodiments, the expression vector is an autonomously replicating vector (i.e., a vector that exists as an extra-chromosomal entity, the replication of which is independent of chromosomal replication, such as a plasmid, an extra-chromosomal element, a minichromosome, or an artificial chromosome). The vector may contain any means for assuring self-replication. In some alternative embodiments, the vector is one in which, when introduced into the host cell, it is integrated into the genome and replicated together with the chromosome(s) into which it has been integrated. Furthermore, in some embodiments, a single vector or plasmid, or two or more vectors or plasmids which together contain the total DNA to be introduced into the genome of the host cell, and/or a transposon is utilized.

In some embodiments, the expression vector contains one or more selectable markers, which permit easy selection of transformed cells. A "selectable marker" is a gene, the product of which provides for biocide or viral resistance, resistance to heavy metals, prototrophy to auxotrophs, and the like. Examples of bacterial selectable markers include, but are not limited to the dal genes from *Bacillus subtilis* or *Bacillus licheniformis*, or markers, which confer antibiotic resistance such as ampicillin, kanamycin, chloramphenicol or tetracycline resistance. Suitable markers for yeast cells include, but are not limited to ADE2, HIS3, LEU2, LYS2, MET3, TRP1, and URA3. Selectable markers for use in filamentous fungal host cells include, but are not limited to, amdS (acetamidase; e.g., from *A. nidulans* or *A. oryzae*), argB (ornithine carbamoyltransferases), bar (phosphinothricin acetyltransferase; e.g., from S. *hygroscopicus*), hph (hygromycin phosphotransferase), niaD (nitrate reductase), pyrG (orotidine-5'-phosphate decarboxylase; e.g., from *A. nidulans* or *A. oryzae*), sC (sulfate adenyltransferase), and trpC (anthranilate synthase), as well as equivalents thereof.

In another aspect, the present invention provides a host cell comprising at least one polynucleotide encoding at least one engineered ligase polypeptide of the present invention, the polynucleotide(s) being operatively linked to one or more control sequences for expression of the engineered ligase enzyme(s) in the host cell. Host cells suitable for use in expressing the polypeptides encoded by the expression vectors of the present invention are well known in the art and include but are not limited to, bacterial cells, such as *E. coli*, *Vibrio fluvialis*, *Streptomyces* and *Salmonella typhimurium* cells; fungal cells, such as yeast cells (e.g., *Saccharomyces cerevisiae* or *Pichia pastoris* (ATCC Accession No. 201178); insect cells such as *Drosophila* S2 and Spodoptera Sf9 cells; animal cells such as CHO, COS, BHK, 293, and Bowes melanoma cells; and plant cells. Exemplary host cells also include various *Escherichia coli* strains (e.g., W3110 (ΔfhuA) and BL21).

Accordingly, in another aspect, the present invention provides methods of producing the engineered ligase polypeptides, where the methods comprise culturing a host cell capable of expressing a polynucleotide encoding the engineered ligase polypeptide under conditions suitable for expression of the polypeptide. In some embodiments, the methods further comprise the steps of isolating and/or purifying the ligase polypeptides, as described herein.

Appropriate culture media and growth conditions for host cells are well known in the art. It is contemplated that any suitable method for introducing polynucleotides for expression of the ligase polypeptides into cells will find use in the present invention. Suitable techniques include, but are not limited to electroporation, biolistic particle bombardment, liposome mediated transfection, calcium chloride transfection, and protoplast fusion.

Engineered ligase polypeptides with the properties disclosed herein can be obtained by subjecting the polynucleotide encoding the naturally occurring or engineered ligase polypeptide to any suitable mutagenesis and/or directed evolution methods known in the art, and/or as described herein. An exemplary directed evolution technique is mutagenesis and/or DNA shuffling (See e.g., Stemmer, Proc. Natl. Acad. Sci. USA 91:10747-10751 [1994]; WO 95/22625; WO 97/0078; WO 97/35966; WO 98/27230; WO 00/42651; WO 01/75767 and U.S. Pat. No. 6,537,746). Other directed evolution procedures that can be used include, among others, staggered extension process (StEP), in vitro recombination (See e.g., Zhao et al., Nat. Biotechnol., 16:258-261 [1998]), mutagenic PCR (See e.g., Caldwell et al., PCR Methods Appl., 3:S136-S140 [1994]), and cassette mutagenesis (See e.g., Black et al., Proc. Natl. Acad. Sci. USA 93:3525-3529 [1996]).

Mutagenesis and directed evolution methods can be readily applied to ligase-encoding polynucleotides to generate variant libraries that can be expressed, screened, and assayed. Any suitable mutagenesis and directed evolution methods find use in the present invention and are well known in the art (See e.g., U.S. Pat. Nos. 5,605,793, 5,811,238, 5,830,721, 5,834,252, 5,837,458, 5,928,905, 6,096,548, 6,117,679, 6,132,970, 6,165,793, 6,180,406, 6,251,674, 6,265,201, 6,277,638, 6,287,861, 6,287,862, 6,291,242, 6,297,053, 6,303,344, 6,309,883, 6,319,713, 6,319,714, 6,323,030, 6,326,204, 6,335,160, 6,335,198, 6,344,356, 6,352,859, 6,355,484, 6,358,740, 6,358,742, 6,365,377, 6,365,408, 6,368,861, 6,372,497, 6,337,186, 6,376,246, 6,379,964, 6,387,702, 6,391,552, 6,391,640, 6,395,547, 6,406,855, 6,406,910, 6,413,745, 6,413,774, 6,420,175, 6,423,542, 6,426,224, 6,436,675, 6,444,468, 6,455,253, 6,479,652, 6,482,647, 6,483,011, 6,484,105, 6,489,146, 6,500,617, 6,500,639, 6,506,602, 6,506,603, 6,518,065, 6,519,065, 6,521,453, 6,528,311, 6,537,746, 6,573,098, 6,576,467, 6,579,678, 6,586,182, 6,602,986, 6,605,430, 6,613,514, 6,653,072, 6,686,515, 6,703,240, 6,716,631, 6,825,001, 6,902,922, 6,917,882, 6,946,296, 6,961,664, 6,995,017, 7,024,312, 7,058,515, 7,105,297, 7,148,054, 7,220,566, 7,288,375, 7,384,387, 7,421,347, 7,430,477, 7,462,469, 7,534,564, 7,620,500, 7,620,502, 7,629,170, 7,702,464, 7,747,391, 7,747,393, 7,751,986, 7,776,598, 7,783,428, 7,795,030, 7,853,410, 7,868,138, 7,783,428, 7,873,477, 7,873,499, 7,904,249, 7,957,912, 7,981,614, 8,014,961, 8,029,988, 8,048,674, 8,058,001, 8,076,138, 8,108,150, 8,170,806, 8,224,580, 8,377,681, 8,383,346, 8,457,903, 8,504,498, 8,589,085, 8,762,066, 8,768,871, 9,593,326, and all related PCT and non-US counterparts; Ling et al., Anal. Biochem., 254(2):157-78 [1997]; Dale et al., Meth. Mol. Biol., 57:369-74 [1996]; Smith, Ann. Rev. Genet., 19:423-462 [1985]; Botstein et al., Science, 229:1193-1201 [1985]; Carter, Biochem. J., 237: 1-7 [1986]; Kramer et al., Cell, 38:879-887 [1984]; Wells et al., Gene, 34:315-323 [1985]; Minshull et al., Curr. Op. Chem. Biol., 3:284-290 [1999]; Christians et al., Nat. Biotechnol., 17:259-264 [1999]; Crameri et al., Nature, 391: 288-291 [1998]; Crameri, et al., Nat. Biotechnol., 15:436-438 [1997]; Zhang et al., Proc. Nat. Acad. Sci. U.S.A., 94:4504-4509 [1997]; Crameri et al., Nat. Biotechnol., 14:315-319 [1996]; Stemmer, Nature, 370:389-391 [1994]; Stemmer, Proc. Nat. Acad. Sci. USA, 91:10747-10751 [1994]; WO 95/22625; WO 97/0078; WO 97/35966; WO 98/27230; WO 00/42651; WO 01/75767; and WO 2009/152336, all of which are incorporated herein by reference).

In some embodiments, the enzyme clones obtained following mutagenesis treatment are screened by subjecting the enzyme preparations to a defined temperature (or other assay conditions) and measuring the amount of enzyme activity remaining after heat treatments or other suitable assay conditions. Clones containing a polynucleotide encoding a ligase polypeptide are then isolated from the gene, sequenced to identify the nucleotide sequence changes (if any), and used to express the enzyme in a host cell. Measuring enzyme activity from the expression libraries can be performed using any suitable method known in the art (e.g., standard biochemistry techniques, such as HPLC analysis).

For engineered polypeptides of known sequence, the polynucleotides encoding the enzyme can be prepared by standard solid-phase methods, according to known synthetic methods. In some embodiments, fragments of up to about 100 bases can be individually synthesized, then joined (e.g., by enzymatic or chemical ligation methods, or polymerase mediated methods) to form any desired continuous sequence. For example, polynucleotides and oligonucleotides disclosed herein can be prepared by chemical synthesis using the classical phosphoramidite method (See e.g., Beaucage et al., Tet. Lett., 22:1859-69 [1981]; and Matthes et al., EMBO J., 3:801-05 [1984]), as it is typically practiced in automated synthetic methods. According to the phosphoramidite method, oligonucleotides are synthesized (e.g., in an automatic DNA synthesizer, purified, annealed, ligated and cloned in appropriate vectors).

Accordingly, in some embodiments, a method for preparing the engineered ligase polypeptide can comprise: (a) synthesizing a polynucleotide encoding a polypeptide comprising an amino acid sequence selected from the amino acid sequence of any variant as described herein, and (b) expressing the ligase polypeptide encoded by the polynucleotide. In some embodiments of the method, the amino acid sequence encoded by the polynucleotide can optionally have one or several (e.g., up to 3, 4, 5, or up to 10) amino acid residue deletions, insertions and/or substitutions. In some embodiments, the amino acid sequence has optionally 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, or 1-50 amino acid residue deletions, insertions and/or substitutions. In some embodiments, the amino acid sequence has optionally 1, 2, 3, 4, 5, 6, 7, 8, 9, 10, 11, 12, 13, 14, 15, 16, 17, 18, 19, 20, 21, 22, 23, 24, 25, 30, 30, 35, 40, 45, or 50 amino acid residue deletions, insertions and/or substitutions. In some embodiments, the amino acid sequence has optionally 1, 2, 3, 4, 5, 6, 7, 8, 9, 10, 11, 12, 13, 14, 15, 16, 18, 20, 21, 22, 23, 24, or 25 amino acid residue deletions, insertions and/or substitutions. In some embodiments, the substitutions are conservative or non-conservative substitutions.

The expressed engineered ligase polypeptide can be evaluated for any desired improved property or combination of properties (e.g., activity, selectivity, stability, acid tolerance, protease sensitivity, etc.) using any suitable assay known in the art, including but not limited to the assays and conditions described herein.

In some embodiments, any of the engineered ligase polypeptides expressed in a host cell are recovered from the cells and/or the culture medium using any one or more of the well-known techniques for protein purification, including, among others, lysozyme treatment, sonication, filtration, salting-out, ultra-centrifugation, and chromatography.

Chromatographic techniques for isolation of the ligase polypeptides include, among others, reverse phase chromatography, high-performance liquid chromatography, ion-exchange chromatography, hydrophobic-interaction chromatography, size-exclusion chromatography, gel electrophoresis, and affinity chromatography. Conditions for purifying a particular enzyme depends, in part, on factors such as net charge, hydrophobicity, hydrophilicity, molecular weight, molecular shape, etc., and will be apparent to those having skill in the art. In some embodiments, affinity techniques may be used to isolate the improved ligase enzymes. For affinity chromatography purification, any antibody that specifically binds a ligase polypeptide of interest may find use. For the production of antibodies, various host animals, including but not limited to rabbits, mice, rats, etc., are immunized by injection with a ligase polypeptide, or a fragment thereof. In some embodiments, the ligase polypeptide or fragment is attached to a suitable carrier, such as BSA, by means of a side chain functional group or linkers attached to a side chain functional group.

In some embodiments, the engineered ligase polypeptide is produced in a host cell by a method comprising culturing a host cell (e.g., an *E. coli* strain) comprising a polynucleotide sequence encoding an engineered ligase polypeptide as described herein under conditions conducive to the production of the engineered ligase polypeptide and recovering the engineered ligase polypeptide from the cells and/or culture medium. In some embodiments, the host cell produces more than one engineered ligase polypeptide.

In some embodiments, the present invention provides a method of producing an engineered ligase polypeptide comprising culturing a recombinant bacterial cell comprising a polynucleotide sequence encoding an engineered ligase polypeptide having at least 85%, 90%, 95%, 96%, 97%, 98%, or 99% sequence identity to reference sequences SEQ ID NO: 2, 6, 32, 34, and/lor 38, and one or more amino acid residue differences, under suitable culture conditions to allow the production of the engineered ligase polypeptide and optionally recovering the engineered ligase polypeptide from the culture and/or cultured bacterial cells. In some embodiments, the host cell produces more than one engineered ligase polypeptide.

In some embodiments, once the engineered ligase polypeptides are recovered from the recombinant host cells and/or culture medium, they are further purified by any suitable method(s) known in the art. In some additional embodiments, the purified engineered ligase polypeptides are combined with other ingredients and compounds to provide compositions and formulations comprising the engineered ligase polypeptide as appropriate for different applications and uses (e.g., diagnostic methods and compositions).

EXPERIMENTAL

The following Examples, including experiments and results achieved, are provided for illustrative purposes only and are not to be construed as limiting the present invention.

In the experimental disclosure below, the following abbreviations apply: ppm (parts per million); M (molar); mM (millimolar), uM and µM (micromolar); nM (nanomolar); mol (moles); gm and g (gram); mg (milligrams); ug and µg (micrograms); L and l (liter); ml and mL (milliliter); cm (centimeters); mm (millimeters); um and µm (micrometers); sec. (seconds); min(s) (minute(s)); h(s) and hr(s) (hour(s)); U (units); MW (molecular weight); rpm (rotations per minute); rcf (relative centrifugal force); psi and PSI (pounds per square inch); ° C. (degrees Centigrade); RT and rt (room temperature); NGS (next-generation sequencing); ds (double stranded); ss (single stranded); CDS (coding sequence); DNA (deoxyribonucleic acid); RNA (ribonucleic acid); E. coli W3110 (commonly used laboratory E. coli strain, available from the Coli Genetic Stock Center [CGSC], New Haven, CT); HTP (high throughput); HPLC (high pressure liquid chromatography); CFSE (carboxyfluorescein succinimidyl ester); IPTG (isopropyl β-D-1-thiogalactopyranoside); PES (polyethersulfone); FIOPC (fold improvements over positive control); EB buffer (10 mM Tris); LB (Luria-Bertani); SPRI (solid phase reversible immobilization); Sigma-Aldrich (Sigma-Aldrich, St. Louis, MO); Promega (Promega, Inc., Madison, WI); EMD Millipore (EMD Millipore or Millipore Sigma, part of Merck KGaA, Darmstad, Germany); Perkin Elmer (Perkin Elmer, Inc, Waltham, MA); Millipore (Millipore, Corp., Billerica MA); MagBio Genomics (MagBio Genomics, Gaithersburg, MD); BioChain (BioChain Institute, Inc., Newark, CA); Difco (Difco Laboratories, BD Diagnostic Systems, Detroit, MI); Molecular Devices (Molecular Devices, LLC, Sunnyvale, CA); Kuhner (Adolf Kuhner, AG, Basel, Switzerland); Microfluidics (Microfluidics, Corp., Westwood, MA); NEB (New England Biolabs, Inc., Ipswich, MA); Applied Biosystems (Applied Biosystems, part of Life Technologies, Corp., Grand Island, NY); Zymo (Zymo Research, Irvine, CA); Agilent (Agilent Technologies, Inc., Santa Clara, CA); Integrated DNA Technologies (Integrated DNA Technologies, Inc., Coralville, IA); Illumina (Illumina, Inc., San Diego, CA); Thermo Scientific (part of Thermo Fisher Scientific, Waltham, MA); GE Healthcare (GE Healthcare Bio-Sciences, Piscataway, NJ); Enzymatics (Enzymatics, Inc., Beverly, MA); and Bio-Rad (Bio-Rad Laboratories, Hercules, CA).

The following polynucleotide and polypeptide sequences find use in the present invention. In some cases (as shown below), the polynucleotide sequence is followed by the encoded polypeptide. SEQ ID NOS:1 and 2 correspond to the wild-type phage T4 DNA ligase (untagged). SEQ ID NOS:3 and 4 correspond to the wild-type phage T4 DNA ligase that has been histidine-tagged. SEQ ID NOS:5 and 6 correspond to an optimized synthetic T4 DNA ligase (untagged).

```
                                                                                  (SEQ ID NO: 1)
ATGATTCTTA AAATTCTGAA CGAAATAGCA TCTATTGGTT CAACTAAACA GAAGCAAGCA ATTCTTGAAA AGAATAAAGA TAATGAATTG

CTTAAACGAG TATATCGTCT GACTTATTCT CGTGGGTTAC AGTATTATAT CAAGAAATGG CCTAAACCTG GTATTGCTAC CCAGAGTTTT

GGAATGTTGA CTCTTACCGA TATGCTTGAC TTCATTGAAT TCACATTAGC TACTCGGAAA TTGACTGGAA ATGCAGCAAT TGAGGAATTA

ACTGGATATA TCACCGATGG TAAAAAGAT GATGTTGAAG TTTTGCGTCG AGTGATGATG CGAGACCTTG AATGTGGTGC TTCAGTATCT

ATTGCAAACA AAGTTTGGCC AGGTTTAATT CCTGAACAAC CTCAAATGCT CGCAAGTTCT TATGATGAAA AAGGCATTAA TAAGAATATC

AAATTTCCAG CCTTTGCTCA GTTAAAAGCT GATGGAGCTC GGTGTTTTGC TGAAGTTAGA GGTGATGAAT TAGATGATGT TCGTCTTTTA

TCACGAGCTG GTAATGAATA TCTAGGATTA GATCTTCTTA AGGAAGAGTT AATTAAAATG ACCGCTGAAG CCCGCCAGAT TCATCCAGAA

GGTGTGTTGA TTGATGGCGA ATTGGTATAC CATGAGCAAG TTAAAAAGGA GCCAGAAGGC CTAGATTTTC TTTTTGATGC TTATCCTGAA

AACAGTAAAG CTAAAGAATT CGCCGAAGTA GCTGAATCAC GTACTGCTTC TAATGGAATC GCCAATAAAT CTTTAAAGGG AACCATTTCT

GAAAAAGAAG CACAATGCAT GAAGTTTCAG GTCTGGGATT ATGTCCCGTT GGTAGAAATA TACAGTCTTC CTGCATTTCG TTTGAAATAT

GATGTACGTT TTTCTAAACT AGAACAAATG ACATCTGGAT ATGATAAAGT AATTTTAATT GAAAACCAGG TAGTAAATAA CCTAGATGAA

GCTAAGGTAA TTTATAAAAA GTATATTGAC CAAGGTCTTG AAGGTATTAT TCTCAAAAAT ATCGATGGAT TATGGGAAAA TGCTCGTTCA

AAAAATCTTT ATAAATTTAA AGAAGTAATT GATGTTGATT TAAAAATTGT AGGAATTTAT CCTCACCGTA AAGACCCTAC TAAAGCGGGT

GGATTTATTC TTGAGTCAGA GTGTGGAAAA ATTAAGGTAA ATGCTGGTTC AGGCTTAAAA GATAAGCCG GTGTAAAATC GCATGAACTT
```

-continued

```
GACCGTACTC GCATTATGGA AAACCAAAAT TATTATATTG GAAAAATTCT AGAGTGCGAA TGCAACGGTT GGTTAAAATC TGATGGCCGC
ACTGATTACG TTAAATTATT CTTCCGATT GCGATTCGTT TACGTGAAGA TAAAACTAAA GCTAATACAT TCGAAGATGT ATTTGGTGAT
TTTCATGAGG TAACTGGTCT ATAA
```

(SEQ ID NO: 2)

Met Ile Leu Lys Ile Leu Asn Glu Ile Ala Ser Ile Gly Ser Thr Lys Gln Lys Gln Ala Ile Leu Glu Lys
Asn Lys Asp Asn Glu Leu Leu Lys Arg Val Tyr Arg Leu Thr Tyr Ser Arg Gly Leu Gln Tyr Tyr Ile Lys
Lys Trp Pro Lys Pro Gly Ile Ala Thr Gln Ser Phe Gly Met Leu Thr Leu Thr Asp Met Leu Asp Phe Ile
Glu Phe Thr Leu Ala Thr Arg Lys Leu Thr Gly Asn Ala Ala Ile Glu Glu Leu Thr Gly Tyr Ile Thr Asp
Gly Lys Lys Asp Asp Val Glu Val Leu Arg Arg Val Met Met Arg Asp Leu Glu Cys Gly Ala Ser Val Ser
Ile Ala Asn Lys Val Trp Pro Gly Leu Ile Pro Glu Gln Pro Gln Met Leu Ala Ser Ser Tyr Asp Glu Lys
Gly Ile Asn Lys Asn Ile Lys Phe Pro Ala Phe Ala Gln Leu Lys Ala Asp Gly Ala Arg Cys Phe Ala Glu
Val Arg Gly Asp Glu Leu Asp Asp Val Arg Leu Leu Ser Arg Ala Gly Asn Glu Tyr Leu Gly Leu Asp Leu
Leu Lys Glu Glu Leu Ile Lys Met Thr Ala Glu Ala Arg Gln Ile His Pro Glu Gly Val Leu Ile Asp Gly
Glu Leu Val Tyr His Glu Gln Val Lys Lys Glu Pro Glu Gly Leu Asp Phe Leu Phe Asp Ala Tyr Pro Glu
Asn Ser Lys Ala Lys Glu Phe Ala Glu Val Ala Glu Ser Arg Thr Ala Ser Asn Gly Ile Ala Asn Lys Ser
Leu Lys Gly Thr Ile Ser Glu Lys Glu Ala Gln Cys Met Lys Phe Gln Val Trp Asp Tyr Val Pro Leu Val
Glu Ile Tyr Ser Leu Pro Ala Phe Arg Leu Lys Tyr Asp Val Arg Phe Ser Lys Leu Glu Gln Met Thr Ser
Gly Tyr Asp Lys Val Ile Leu Ile Glu Asn Gln Val Val Asn Asn Leu Asp Glu Ala Lys Val Ile Tyr Lys
Lys Tyr Ile Asp Gln Gly Leu Glu Gly Ile Ile Leu Lys Asn Ile Asp Gly Leu Trp Glu Asn Ala Arg Ser
Lys Asn Leu Tyr Lys Phe Lys Glu Val Ile Asp Val Asp Leu Lys Ile Val Gly Ile Tyr Pro His Arg Lys
Asp Pro Thr Lys Ala Gly Gly Phe Ile Leu Glu Ser Glu Cys Gly Lys Ile Lys Val Asn Ala Gly Ser Gly
Leu Lys Asp Lys Ala Gly Val Lys Ser His Glu Leu Asp Arg Thr Arg Ile Met Glu Asn Gln Asn Tyr Tyr
Ile Gly Lys Ile Leu Glu Cys Glu Cys Asn Gly Trp Leu Lys Ser Asp Gly Arg Thr Asp Tyr Val Lys Leu
Phe Leu Pro Ile Ala Ile Arg Leu Arg Glu Asp Lys Thr Lys Ala Asn Thr Phe Glu Asp Val Phe Gly Asp
Phe His Glu Val Thr Gly Leu (SEQ ID NO: 3)

```
ATGCATCACC ATCACCATCA CGGTGGCAGC GGTATGATTC TTAAAATTCT GAACGAAATA GCATCTATTG GTTCAACTAA ACAGAAGCAA
GCAATTCTTG AAAAGAATAA AGATAATGAA TTGCTTAAAC GAGTATATCG TCTGACTTAT TCTCGTGGGT TACAGTATTA TATCAAGAAA
TGGCCTAAAC CTGGTATTGC TACCCAGAGT TTTGGAATGT TGACTCTTAC CGATATGCTT GACTTCATTG AATTCACATT AGCTACTCGG
AAATTGACTG GAAATGCAGC AATTGAGGAA TTAACTGGAT ATATCACCGA TGGTAAAAAA GATGATGTTG AAGTTTTGCG TCGAGTGATG
ATGCGAGACC TTGAATGTGG TGCTTCAGTA TCTATTGCAA ACAAGTTTG GCCAGGTTTA ATTCCTGAAC AACCTCAAAT GCTCGCAAGT
TCTTATGATG AAAAAGGCAT TAATAAGAAT ATCAAATTTC CAGCCTTTGC TCAGTTAAAA GCTGATGGAG CTCGGTGTTT TGCTGAAGTT
AGAGGTGATG AATTAGATGA TGTTCGTCTT TTATCACGAG CTGGTAATGA ATATCTAGGA TTAGATCTTC TTAAGGAAGA GTTAATTAAA
ATGACCGCTG AAGCCCGCCA GATTCATCCA GAAGGTGTGT TGATTGATGG CGAATTGGTA TACCATGAGC AAGTTAAAAA GGAGCCAGAA
GGCCTAGATT TCTTTTTTGA TGCTTATCCT GAAAACAGTA AAGCTAAAGA ATTCGCCGAA GTAGCTGAAT CACGTACTGC TTCTAATGGA
ATCGCCAATA AATCTTTAAA GGGAACCATT TCTGAAAAAG AAGCACAATG CATGAAGTTT CAGGTCTGGG ATTATGTCCC GTTGGTAGAA
ATATACAGTC TTCCTGCATT TCGTTTGAAA TATGATGTAC GTTTTTCTAA ACTAGAACAA ATGACATCTG GATATGATAA AGTAATTTTA
ATTGAAAACC AGGTAGTAAA TAACCTAGAT GAAGCTAAGG TAATTTATAA AAAGTATATT GACCAAGGTC TTGAAGGTAT TATTCTCAAA
AATATCGATG GATTATGGGA AAATGCTCGT TCAAAAAATC TTTATAAATT TAAAGAAGTA ATTGATGTTG ATTTAAAAAT TGTAGGAATT
TATCCTCACC GTAAAGACCC TACTAAAGCG GGTGGATTTA TTCTTGAGTC AGAGTGTGGA AAAATTAAGG TAAATGCTGG TTCAGGCTTA
AAAGATAAAG CCGGTGTAAA ATCGCATGAA CTTGACCGTA CTCGCATTAT GGAAAACCAA AATTATTATA TTGGAAAAAT TCTAGAGTGC
GAATGCAACG GTTGGTTAAA ATCTGATGGC CGCACTGATT ACGTTAAATT ATTTCTTCCG ATTGCGATTC GTTTACGTGA AGATAAAACT
```

-continued

AAAGCTAATA CATTCGAAGA TGTATTTGGT GATTTTCATG AGGTAACTGG TCTATAA (SEQ ID NO: 4)

Met His His His His His His Gly Gly Ser Gly Met Ile Leu Lys Ile Leu Asn Glu Ile Ala Ser Ile Gly

Ser Thr Lys Gln Lys Gln Ala Ile Leu Glu Lys Asn Lys Asp Asn Glu Leu Leu Lys Arg Val Tyr Arg Leu

Thr Tyr Ser Arg Gly Leu Gln Tyr Tyr Ile Lys Lys Trp Pro Lys Pro Gly Ile Ala Thr Gln Ser Phe Gly

Met Leu Thr Leu Thr Asp Met Leu Asp Phe Ile Glu Phe Thr Leu Ala Thr Arg Lys Leu Thr Gly Asn Ala

Ala Ile Glu Glu Leu Thr Gly Tyr Ile Thr Asp Gly Lys Lys Asp Asp Val Glu Val Leu Arg Arg Val Met

Met Arg Asp Leu Glu Cys Gly Ala Ser Val Ser Ile Ala Asn Lys Val Trp Pro Gly Leu Ile Pro Glu Gln

Pro Gln Met Leu Ala Ser Ser Tyr Asp Glu Lys Gly Ile Asn Lys Asn Ile Lys Phe Pro Ala Phe Ala Gln

Leu Lys Ala Asp Gly Ala Arg Cys Phe Ala Glu Val Arg Gly Asp Glu Leu Asp Asp Val Arg Leu Leu Ser

Arg Ala Gly Asn Glu Tyr Leu Gly Leu Asp Leu Leu Lys Glu Glu Leu Ile Lys Met Thr Ala Glu Ala Arg

Gln Ile His Pro Glu Gly Val Leu Ile Asp Gly Glu Leu Val Tyr His Glu Gln Val Lys Lys Glu Pro Glu

Gly Leu Asp Phe Leu Phe Asp Ala Tyr Pro Glu Asn Ser Lys Ala Lys Glu Phe Ala Glu Val Ala Glu Ser

Arg Thr Ala Ser Asn Gly Ile Ala Asn Lys Ser Leu Lys Gly Thr Ile Ser Glu Lys Glu Ala Gln Cys Met

Lys Phe Gln Val Trp Asp Tyr Val Pro Leu Val Glu Ile Tyr Ser Leu Pro Ala Phe Arg Leu Lys Tyr Asp

Val Arg Phe Ser Lys Leu Glu Gln Met Thr Ser Gly Tyr Asp Lys Val Ile Leu Ile Glu Asn Gln Val Val

Asn Asn Leu Asp Glu Ala Lys Val Ile Tyr Lys Lys Tyr Ile Asp Gln Gly Leu Glu Gly Ile Ile Leu Lys

Asn Ile Asp Gly Leu Trp Glu Asn Ala Arg Ser Lys Asn Leu Tyr Lys Phe Lys Glu Val Ile Asp Val Asp

Leu Lys Ile Val Gly Ile Tyr Pro His Arg Lys Asp Pro Thr Lys Ala Gly Gly Phe Ile Leu Glu Ser Glu

Cys Gly Lys Ile Lys Val Asn Ala Gly Ser Gly Leu Lys Asp Lys Ala Gly Val Lys Ser His Glu Leu Asp

Arg Thr Arg Ile Met Glu Asn Gln Asn Tyr Tyr Ile Gly Lys Ile Leu Glu Cys Glu Cys Asn Gly Trp Leu

Lys Ser Asp Gly Arg Thr Asp Tyr Val Lys Leu Phe Leu Pro Ile Ala Ile Arg Leu Arg Glu Asp Lys Thr

Lys Ala Asn Thr Phe Glu Asp Val Phe Gly Asp Phe His Glu Val Thr Gly Leu (SEQ ID NO: 5)

ATGATTCTTA AAATTCTGAA CGAAATTGCA AGCATTGGTT CCACTAAACA AAAACAAGCC ATTCTGGAAA AAAATAAAGA CAATGAACTG

TTAAAGCGCG TGTATCGCCT GACCTATTCG CGTGGCCTGC AATACTATAT TAAAAAATGG CCCAAACCGG GCATTGCGAC GCAGAGCTTC

GGCATGCTGA CCCTGACCGA TATGCTGGAT TTTATCGAGT TTACTCTTGC GACGCGCAAA CTTACCGGCA ACGCTGCTAT TGAAGAATTG

ACGGGCTATA TTACCGATGG CAAAAAGAT GATGTTGAGG TGCTGCGTCG CGTCATGATG CGTGATCTGG AGTGCGGTGC GTCAGTGAGC

ATCGCTAACA AGTGTGGCC GGGTTTGATC CCGGAACAGC CACAGATGCT TGCAAGCAGC TACGATGAAA AGGGCATTAA CAAAAATATC

AAATTTCCGG CTTTCGCCCA GCTGAAAGCG GATGGCGCGC GCTGCTTCGC CGAGGTACGC GGTGACGAAC TGGACGACGT TCGTCTGCTG

TCTCGCGCTG GCAATGAATA TCTGGGTCTG GATCTGCTGA AGAAGAACT GATTAAGATG ACCGCCGAGG CGCGCCAAAT CCACCCCGAA

GGGGTGCTGA TTGATGGCGA ACTGGTGTAT CACGAACAGG TTAAAAAGGA GCCGGAGGGG TTGGATTTCC TGTTTGATGC CTACCCGGAG

AATAGCAAAG CGAAAGAATT TGCGGAAGTG GCGGAATCCC GCACCGCAAG CAATGGTATC GCAAATAAAT CGCTGAAGGG CACCATTTCT

GAGAAAGAAG CACAGTGTAT GAAGTTCCAG GTGTGGGACT ACGTGCCACT GGTTGAGATC TACTCCCTGC CAGCGTTTCG CCTGAAATAC

GATGTGCGTT TTTCAAAACT GGAACAGATG ACGAGCGGAT ATGATAAAGT AATTTTAATC GAGAACCAGG TCGTGAACAA CCTGGATGAA

GCAAAGTTA TCTATAAAAA ATATATTGAT CAGGGCTTAG AAGGCATTAT CCTGAAGAAC ATTGATGGCC TTTGGGAAAA TGCACGCAGC

AAAAACCTGT ATAAATTTAA AGAAGTGATT GATGTAGATC TGAAGATTGT TGGTATTTAC CCGCATCGCA AGACCCGAC CAAAGCAGGT

GGTTTCATCC TGGAATCTGA ATGCGGTAAA ATTAAAGTGA ACGCAGGCAG TGGTTTGAAA GATAAAGCTG GTGTTAAAAG TCACGAACTG

GATCGCACGC GCATCATGGA AAACCAGAAC TATTATATCG GCAAAATTCT GGAATGCGAG TGCAACGGGT GGCTTAAGAG CGACGGGCGC

ACGGACTATG TTAAATTGTT CCTGCCGATT GCGATTCGCC TTCGCGAAGA CAAAACTAAG GCGAATACTT TCGAAGATGT GTTCGGTGAT

TTTCATGAAG TCACGGGTCT GTAA

-continued (SEQ ID NO: 6)

Met Ile Leu Lys Ile Leu Asn Glu Ile Ala Ser Ile Gly Ser Thr Lys Gln Lys Gln Ala Ile Leu Glu Lys
Asn Lys Asp Asn Glu Leu Leu Lys Arg Val Tyr Arg Leu Thr Tyr Ser Arg Gly Leu Gln Tyr Tyr Ile Lys
Lys Trp Pro Lys Pro Gly Ile Ala Thr Gln Ser Phe Gly Met Leu Thr Leu Thr Asp Met Leu Asp Phe Ile
Glu Phe Thr Leu Ala Thr Arg Lys Leu Thr Gly Asn Ala Ala Ile Glu Glu Leu Thr Gly Tyr Ile Thr Asp
Gly Lys Lys Asp Asp Val Glu Val Leu Arg Arg Val Met Met Arg Asp Leu Glu Cys Gly Ala Ser Val Ser
Ile Ala Asn Lys Val Trp Pro Gly Leu Ile Pro Glu Gln Pro Gln Met Leu Ala Ser Ser Tyr Asp Glu Lys
Gly Ile Asn Lys Asn Ile Lys Phe Pro Ala Phe Ala Gln Leu Lys Ala Asp Gly Ala Arg Cys Phe Ala Glu
Val Arg Gly Asp Glu Leu Asp Asp Val Arg Leu Leu Ser Arg Ala Gly Asn Glu Tyr Leu Gly Leu Asp Leu
Leu Lys Glu Glu Leu Ile Lys Met Thr Ala Glu Ala Arg Gln Ile His Pro Glu Gly Val Leu Ile Asp Gly
Glu Leu Val Tyr His Glu Gln Val Lys Lys Glu Pro Glu Gly Leu Asp Phe Leu Phe Asp Ala Tyr Pro Glu
Asn Ser Lys Ala Lys Glu Phe Ala Glu Val Ala Glu Ser Arg Thr Ala Ser Asn Gly Ile Ala Asn Lys Ser
Leu Lys Gly Thr Ile Ser Glu Lys Glu Ala Gln Cys Met Lys Phe Gln Val Trp Asp Tyr Val Pro Leu Val
Glu Ile Tyr Ser Leu Pro Ala Phe Arg Leu Lys Tyr Asp Val Arg Phe Ser Lys Leu Glu Gln Met Thr Ser
Gly Tyr Asp Lys Val Ile Leu Ile Glu Asn Gln Val Val Asn Asn Leu Asp Glu Ala Lys Val Ile Tyr Lys
Lys Tyr Ile Asp Gln Gly Leu Glu Gly Ile Ile Leu Lys Asn Ile Asp Gly Leu Trp Glu Asn Ala Arg Ser
Lys Asn Leu Tyr Lys Phe Lys Glu Val Ile Asp Val Asp Leu Lys Ile Val Gly Ile Tyr Pro His Arg Lys
Asp Pro Thr Lys Ala Gly Gly Phe Ile Leu Glu Ser Glu Cys Gly Lys Ile Lys Val Asn Ala Gly Ser Gly
Leu Lys Asp Lys Ala Gly Val Lys Ser His Glu Leu Asp Arg Thr Arg Ile Met Glu Asn Gln Asn Tyr Tyr
Ile Gly Lys Ile Leu Glu Cys Glu Cys Asn Gly Trp Leu Lys Ser Asp Gly Arg Thr Asp Tyr Val Lys Leu
Phe Leu Pro Ile Ala Ile Arg Leu Arg Glu Asp Lys Thr Lys Ala Asn Thr Phe Glu Asp Val Phe Gly Asp
Phe His Glu Val Thr Gly Leu

The following sequences are nucleic acid sequences of the oligonucleotides used in the following Examples.

(SEQ ID NO: 7)
/5Phos/TGCTACTCATCCTAGTCCTGTTGCT/iCy3/GCCAAGCTATTT
AATATCATGCACA (SEQ ID NO: 8)
/5Phos/GTGCATGATATTAAATAGCTTGGCAGCAACAGGACTAGGATGA
GTAGCAA (SEQ ID NO: 9)
ACACGACGCTCTTCCGATC*T (SEQ ID NO: 10)
/5Phos/GATCGGAAGAGCGTCGTGT/3BioTEG/

(SEQ ID NO: 11)
/5Phos/TGCTACTCATCCTAGTCCTGTTGCTGCCAAGCTATTTAATATC
ATGCACA (SEQ ID NO: 12)
/5Phos/GTGCATGATATTAAATAGCTTGGCAGCAACAGGACTAGGATGA
GTAGCAA (SEQ ID NO: 13)
ACACGACGCTCTTCCGATC*T (SEQ ID NO: 14)
/5Phos/GATCGGAAGAGCGTCGTGT (SEQ ID NO: 15)
/5Phos/GATCGGAAGAGCACACGTCTGAACTCCAGTC/ideoxyU/ACA
CTCTTTCCCTACACGACGCTCTTCCGATC*T (SEQ ID NO: 16)
/5Phos/GATCGGAAGAGCGTCGTGT/3AmMO/

(SEQ ID NO: 17)
AATGATACGGCGACCACCGAGATCTACACTCTTTCCCTACACGACGCTCT
TCCGATC*T (SEQ ID NO: 18)
/5Phos/GATCGGAAGAGCACACGTCTGAACTCCAGTCAC<u>ATCACG</u>ATCT
CGTATGCCGTCTTCTGCTTG (SEQ ID NO: 19)
AAGCCGGTGTAAAATCGCATGA (SEQ ID NO: 20)
AGTAAACGAATCGCAATCGGAAGA (SEQ ID NO: 21)
CAGCCGGTGTAAAATCGCATGA (SEQ ID NO: 22)
CGTAAACGAATCGCAATCGGAAGA (SEQ ID NO: 23)
GAGCCGGTGTAAAATCGCATGA (SEQ ID NO: 24)
GGTAAACGAATCGCAATCGGAAGA

```
                                                       (SEQ ID NO: 25)
TAGCCGGTGTAAAATCGCATGA (SEQ ID NO: 26)
TGTAAACGAATCGCAATCGGAAGA (SEQ ID NO: 27)
AAGCCGGTGTAAAATCGCATGAACTTGACCGTACTCGCATTATGGAAAAC

CAAAATTATTATATTGGAAAAATTCTAGAGTGCGAATGCAACGGTTGGTT

AAAATCTGATGGCCGCACTGATTACGTTAAATTATTTCTTCCGATTGCGA

TTCGTTTACA (SEQ ID NO: 28)
CAGCCGGTGTAAAATCGCATGAACTTGACCGTACTCGCATTATGGAAAAC

CAAAATTATTATATTGGAAAAATTCTAGAGTGCGAATGCAACGGTTGGTT

AAAATCTGATGGCCGCACTGATTACGTTAAATTATTTCTTCCGATTGCGA

TTCGTTTACC (SEQ ID NO: 29)
GAGCCGGTGTAAAATCGCATGAACTTGACCGTACTCGCATTATGGAAAAC

CAAAATTATTATATTGGAAAAATTCTAGAGTGCGAATGCAACGGTTGGTT

AAAATCTGATGGCCGCACTGATTACGTTAAATTATTTCTTCCGATTGCGA

TTCGTTTACG (SEQ ID NO: 30)
TAGCCGGTGTAAAATCGCATGAACTTGACCGTACTCGCATTATGGAAAAC

CAAAATTATTATATTGGAAAAATTCTAGAGTGCGAATGCAACGGTTGGTT

AAAATCTGATGGCCGCACTGATTACGTTAAATTATTTCTTCCGATTGCGA

TTCGTTTACT
```

The following sequences correspond to engineered ligase variants provided by the present invention.

```
                                                       (SEQ ID NO: 31)
ATGATTCTTA AAATTCTGAA CGAAATTGCA AGCATTGGTT CCACTAAACA AAAACAAGCC ATTCTGGAAA AAAATAAAGA CAATGAACTG

TTAAAGCGCG TGTATCGCCT GACCTATTCG CGTGGCCTGC AATACTATAT TAAAAAATGG CCCAAACCGG GCATTGCGAC GCAGAGCTTC

GGCATGCTGA CCCTGACCGA TATGCTGGAT TTTATCGAGT TTACTCTTGC GACGCGCAAA CTTACCGGCA ACGCTGCTAT TAGAGAATTG

ACGGGCTATA TTACCGATGG CAAAAAGAT GATGTTGAGG TGCTGCGTCG CGTCATGATG CGTGATCTGG AGTGCGGTGC GTCAGTGAGC

ATCGCTAACA AAGTGTGGCC GGGTTTGATC CCGGAACAGC CACAGATGCT TGCAAGCAGC TACGATGAAA AGGGCATTAA CAAAAATATC

AAATTTCCGG CTTTCGCCCA GCTGAAAGCG GATGGCGCGC GCTGCTTCGC CGAGGTACGC GGTGACGAAC TGGACGACGT TCGTCTGCTG

TCTCGCGCTG GCAATGAATA TCTGGGTCTG GATCTGCTGA AGAAGAACT GATTAAGATG ACCGCCGAGG CGCGCCAAAT CCACCCCGAA

GGGGTGCTGA TTGATGGCGA ACTGGTGTAT CACGAACAGG TTGCAAAAGA GCCGGAGGGG TTGGATTTCC TGTTTGATGC CTACCCGGAG

AATAGCAAAG CGAAAGAATT TGCGGAAGTG GCGGAATCCC GCACCGCAAG CAATGGTATC GCAAATAAAT CGCTGAAGGG CACCATTTCT

GAGAAAGAAG CACAGTGTAT GAAGTTCCAG GTGTGGGACT ACGTGCCACT GGTTGAGATC TACTCCCTGC AGCGTTTCG CCTGAAATAC

GATGTGCGTT TTTCAAAACT GGAACAGATG ACGAGCGGAT ATGATAAAGT AATTTTAATC GAGAACCAGG TCGTGAACAA CCTGGATGAA

GCAAAAGTTA TCTATAAAAA ATATATTGAT CAGGGCTTAG AAGGCATTAT CCTGAAGAAC ATTGATGGCC TTTGGGAAAA TGCACGCAGC

AAAAACCTGT ATAAATTTAA AGAAGTGATT GATGTAGATC TGAAGATTGT TGGTATTTAC CCGCATCGCA AAGACCCGAC CAAAGCAGGT

GGTTTCATCC TGGAATCTGA ATGCGGTAAA ATTAAAGTGA ACGCAGGCAG TGGTTTGAAA GATAAAGCTG GTGTTAAAAG TCACGAACTG

GATCGCACGC GCATCATGGA AAACCAGAAC TATTATATCG GCAAAATTCT GGAATGCAAA TGCAACGGGT GGCTTAAGAG CGATGGGCGC

AAAGACTATG TTAAATTGTT CCTGCCGATT GCGATTCGCC TTCGCGAAGA CAAAACTAAG GCGAATACTT TCGAAGATGT GTTCGGTGAT

TTTCATGAAG TCACGGGTCT GTAA
```

```
                                                       (SEQ ID NO: 32)
Met Ile Leu Lys Ile Leu Asn Glu Ile Ala Ser Ile Gly Ser Thr Lys Gln Lys Gln Ala Ile Leu Glu Lys

Asn Lys Asp Asn Glu Leu Leu Lys Arg Val Tyr Arg Leu Thr Tyr Ser Arg Gly Leu Gln Tyr Tyr Ile Lys

Lys Trp Pro Lys Pro Gly Ile Ala Thr Gln Ser Phe Gly Met Leu Thr Leu Thr Asp Met Leu Asp Phe Ile

Glu Phe Thr Leu Ala Thr Arg Lys Leu Thr Gly Asn Ala Ala Ile Arg Glu Leu Thr Gly Tyr Ile Thr Asp

Gly Lys Lys Asp Asp Val Glu Val Leu Arg Arg Val Met Met Arg Asp Leu Glu Cys Gly Ala Ser Val Ser

Ile Ala Asn Lys Val Trp Pro Gly Leu Ile Pro Glu Gln Pro Gln Met Leu Ala Ser Ser Tyr Asp Glu Lys

Gly Ile Asn Lys Asn Ile Lys Phe Pro Ala Phe Ala Gln Leu Lys Ala Asp Gly Ala Arg Cys Phe Ala Glu

Val Arg Gly Asp Glu Leu Asp Asp Val Arg Leu Leu Ser Arg Ala Gly Asn Glu Tyr Leu Gly Leu Asp Leu

Leu Lys Glu Glu Leu Ile Lys Met Thr Ala Glu Ala Arg Gln Ile His Pro Glu Gly Val Leu Ile Asp Gly

Glu Leu Val Tyr His Glu Gln Val Ala Lys Glu Pro Glu Gly Leu Asp Phe Leu Phe Asp Ala Tyr Pro Glu
```

```
Asn Ser Lys Ala Lys Glu Phe Ala Glu Val Ala Glu Ser Arg Thr Ala Ser Asn Gly Ile Ala Asn Lys Ser

Leu Lys Gly Thr Ile Ser Glu Lys Glu Ala Gln Cys Met Lys Phe Gln Val Trp Asp Tyr Val Pro Leu Val

Glu Ile Tyr Ser Leu Pro Ala Phe Arg Leu Lys Tyr Asp Val Arg Phe Ser Lys Leu Glu Gln Met Thr Ser

Gly Tyr Asp Lys Val Ile Leu Ile Glu Asn Gln Val Val Asn Asn Leu Asp Glu Ala Lys Val Ile Tyr Lys

Lys Tyr Ile Asp Gln Gly Leu Glu Gly Ile Ile Leu Lys Asn Ile Asp Gly Leu Trp Glu Asn Ala Arg Ser

Lys Asn Leu Tyr Lys Phe Lys Glu Val Ile Asp Val Asp Leu Lys Ile Val Gly Ile Tyr Pro His Arg Lys

Asp Pro Thr Lys Ala Gly Gly Phe Ile Leu Glu Ser Glu Cys Gly Lys Ile Lys Val Asn Ala Gly Ser Gly

Leu Lys Asp Lys Ala Gly Val Lys Ser His Glu Leu Asp Arg Thr Arg Ile Met Glu Asn Gln Asn Tyr Tyr

Ile Gly Lys Ile Leu Glu Cys Lys Cys Asn Gly Trp Leu Lys Ser Asp Gly Arg Lys Asp Tyr Val Lys Leu

Phe Leu Pro Ile Ala Ile Arg Leu Arg Glu Asp Lys Thr Lys Ala Asn Thr Phe Glu Asp Val Phe Gly Asp

Phe His Glu Val Thr Gly Leu
```

(SEQ ID NO: 33)
```
ATGATTCTTA AAATTCTGAA CGAAATTGCA AGCATTGGTT CCACTAAACA AAACAAGCC ATTCTGGAAA AAATAAAGA CAATGAACTG

TTAAAGCGCG TGTATCGCCT GACCTATTCG CGTGGCCTGC AATACTATAT TAAAAAATGG CCCAAACCGG GCATTGCGAC GCAGAGCTTC

GGCATGCTGA CCCTGACCGA TATGCTGGAT TTTATCGAGT TTACTCTTGC GACGCGCAAA CTTACCGGCA ACGCTGCTAT TAGAGAATTG

ACGGGCTATA TTACCGATGG CAAAAAAGAT GATGTTGAGG TGCTGCGTCG CGTCATGATG CGTGATCTGG AGTGCGGTGC GTCAGTGAGC

ATCGCTAACA AGTGTGGAA GGGTTTGATC CCGGAACAGC CACAGATGCT TGCAAGCAGC TACGATGAAA AGGGCATTAA CAAAAATATC

AAATTTCCGG CTTTCGCCCA GCTGAAAGCG GATGGCGCGC GCTGCTTCGC CGAGGTACGC GGTGACGAAC TGGACGACGT TCGTCTGCTG

TCTCGCGCTG GCAATGAATA TCTGGGTCTG GATCTGCTGA AGAAGAACT GATTAAGATG ACCGCCGAGG CGCGCCAAAT CCACCCCGAA

GGGGTGCTGA TTGATGGCGA ACTGGTGTAT CACGAACAGG TTGCAAAAGA GCCGGAGGGG TTGGATTTCC TGTTTGATGC CTACCCGGAG

AATAGCAAAG CGAAAGAATT TGCGGAAGTG GCGGAATCCC GCACCGCAAG CAATGGTATC GCAAATAAAT CGCTGAAGGG CACCATTTCT

GAGAAAGAAG CACAGTGTAT GAAGTTCCAG GTGTGGGACT ACGTGCCACT GGTTGAGATC TACTCCCTGC CAGCGTTTCG CCTGAAATAC

GATGTGCGTT TTTCAAAACT GGAACAGATG ACGAGCGGAT ATGATAAAGT AATTTTAATC GAGAACCAGG TCGTGAACAA CCTGGATGAA

GCAAAGTTA TCTATAAAAA ATATATTGAT CAGGGCTTAG AAGGCATTAT CCTGAAGAAC ATTGATGGCC TTTGGGAAAA TGCACGCAGC

AAAAACCTGT ATAAATTTAA AGAAGTGATT GATGTAGATC TGAAGATTGT TGGTATTTAC CCGCATCGCA AAGACCCGAC CAAAGCAGGT

GGTTTCATCC TGGAATCTGA ATGCGGTAAA ATTAAAGTGA ACGCAGGCAG TGGTTTGAAA GATAAAGCTG GTGTTAAAAG TCACGAACTG

GATCGCACGC GCATCATGGA AAACCAGAAC TATTATATCG GCAAAATTCT GGAATGCAAA TGCAACGGGT GGCTTAAGAG CGATGGGCGC

AAAGACTATG TTAAATTGTT CCTGCCGATT GCGATTCGCC TTCGCGAAGA CAAAACTAAG GCGAATACTT TCGAAGATGT GTTCGGTGAT

TTTCATGAAG TCACGGGTCT GTAA
```

(SEQ ID NO: 34)
```
Met Ile Leu Lys Ile Leu Asn Glu Ile Ala Ser Ile Gly Ser Thr Lys Gln Lys Gln Ala Ile Leu Glu Lys

Asn Lys Asp Asn Glu Leu Leu Lys Arg Val Tyr Arg Leu Thr Tyr Ser Arg Gly Leu Gln Tyr Tyr Ile Lys

Lys Trp Pro Lys Pro Gly Ile Ala Thr Gln Ser Phe Gly Met Leu Thr Leu Thr Asp Met Leu Asp Phe Ile

Glu Phe Thr Leu Ala Thr Arg Lys Leu Thr Gly Asn Ala Ala Ile Arg Glu Leu Thr Gly Tyr Ile Thr Asp

Gly Lys Lys Asp Asp Val Glu Val Leu Arg Arg Val Met Met Arg Asp Leu Glu Cys Gly Ala Ser Val Ser

Ile Ala Asn Lys Val Trp Lys Gly Leu Ile Pro Glu Gln Pro Gln Met Leu Ala Ser Ser Tyr Asp Glu Lys

Gly Ile Asn Lys Asn Ile Lys Phe Pro Ala Phe Ala Gln Leu Lys Ala Asp Gly Ala Arg Cys Phe Ala Glu

Val Arg Gly Asp Glu Leu Asp Asp Val Arg Leu Leu Ser Arg Ala Gly Asn Glu Tyr Leu Gly Leu Asp Leu

Leu Lys Glu Glu Leu Ile Lys Met Thr Ala Glu Ala Arg Gln Ile His Pro Glu Gly Val Leu Ile Asp Gly

Glu Leu Val Tyr His Glu Gln Val Ala Lys Glu Pro Glu Gly Leu Asp Phe Leu Phe Asp Ala Tyr Pro Glu

Asn Ser Lys Ala Lys Glu Phe Ala Glu Val Ala Glu Ser Arg Thr Ala Ser Asn Gly Ile Ala Asn Lys Ser
```

-continued

Leu Lys Gly Thr Ile Ser Glu Lys Glu Ala Gln Cys Met Lys Phe Gln Val Trp Asp Tyr Val Pro Leu Val

Glu Ile Tyr Ser Leu Pro Ala Phe Arg Leu Lys Tyr Asp Val Arg Phe Ser Lys Leu Glu Gln Met Thr Ser

Gly Tyr Asp Lys Val Ile Leu Ile Glu Asn Gln Val Val Asn Asn Leu Asp Glu Ala Lys Val Ile Tyr Lys

Lys Tyr Ile Asp Gln Gly Leu Glu Gly Ile Ile Leu Lys Asn Ile Asp Gly Leu Trp Glu Asn Ala Arg Ser

Lys Asn Leu Tyr Lys Phe Lys Glu Val Ile Asp Val Asp Leu Lys Ile Val Gly Ile Tyr Pro His Arg Lys

Asp Pro Thr Lys Ala Gly Gly Phe Ile Leu Glu Ser Glu Cys Gly Lys Ile Lys Val Asn Ala Gly Ser Gly

Leu Lys Asp Lys Ala Gly Val Lys Ser His Glu Leu Asp Arg Thr Arg Ile Met Glu Asn Gln Asn Tyr Tyr

Ile Gly Lys Ile Leu Glu Cys Lys Cys Asn Gly Trp Leu Lys Ser Asp Gly Arg Lys Asp Tyr Val Lys Leu

Phe Leu Pro Ile Ala Ile Arg Leu Arg Glu Asp Lys Thr Lys Ala Asn Thr Phe Glu Asp Val Phe Gly Asp

Phe His Glu Val Thr Gly Leu (SEQ ID NO: 35)
ATGATTCTTA AAATTCTGAA CGAAATTGCA AGCATTGGTT CCACTAAACA AAACAAGCC ATTCTGGAAA AAATAAAGA CAATGAACTG
TTAAAGCGCG TGTATCGCCT GACCTATTCG CGTGGCCTGC AATACTATAT TAAAAAATGG CCCAAACCGG GCATTGCGAC GCAGAGCTTC
GGCATGACTA CCCTGACCGA TATGCTGGAT TTTATCGAGT TTACTCTTGC GACGCGCAAA CTTACCGGCA ACGCTGCTAT TAGAGAATTG
ACGGGCTATA TTACCGATGG CAAAAAAGAT GATGTTGAGG TGCTGCGTCG CGTCATGATG CGTGATCTGG AGTGCGGTGC GTCAGTGAGC
ATCGCTAACA AAGTGTGGAA GGGTTTGATC CCGGAACAGC CACAGATGCT TGCAAGCAGC TACGATGAAA AGGGCATTAA CAAAAGAATC
AAATTTCCGG CTTTCGCCCA GCTGAAAGCG GATGGCGCGC GCTGCTTCGC CGAGGTACGC GGTGACGAAC TGGACGACGT TCGTCTGCTG
TCTCGCGCTG GCAATGAATA TCTGGGTCTG GATCTGCTGA AGAAGAACT GATTAAGATG ACCGCCGAGG CGCGCCAAAT CCACCCCGAA
GGGGTGCTGA TTGATGGCGA ACTGGTGTAT CACGAACAGG TTGCAAAAGA GCCGGAGGGG TTGGATTTCC TGTTTGATGC TTACCCGCCT
AATAGCAAAG CGAAAGAATT TGCGGAAGTG GCGGAATCCC GCACCGCAAG CAATGGTATC GCAAATAAAT CGCTGAAGGG CACCATTTCT
GAGAAAGAAG CACAGTGTAT GAAGTTCCAG GTGTGGGACT ACGTGCCACT GGTTGAGATC TACTCCCTGC CAGCGTTTCG CCTGAAATAC
GATGTGCGTT TTTCAAAACT GGAACAGATG ACGAGCGGAT ATGATAAAGT AATTTTAATC GAGAACCAGG TCGTGAACAA CCTGGATGAA
GCAAAGTTA TCTATAAAAA ATATATTGAT CAGGGCTTAG AAGGCATTAT CCTGAAGAAC ATTGATGGCC TTTGGGAAAA TGCACGCAGC
AAAAACCTGT ATAAATTTAA AGAAGTGATT TGGGTAGATC TGAAGATTGT TGGTATTTAC CCGCATCGCA AGACCCGAC CAAAGCAGGT
GGTTTCATCC TGGAATCTGA ATGCGGTAAA ATTAAAGTGA ACGCAGGCAG TGGTTTGAAA GATAAAGCTG GTGTTAAAAG TCACGAACTG
GATCGCACGC GCATCATGGA AAACCAGAAC TATTATATCG GCAAAATTCT GGAATGCAAA TGCAACGGGT GGCTTAAGAG CGATGGGCGC
AAACCCTATG TGAAATTGTT CCTGCCGATT GCGATTCGCC TTCGCGAAGA CAAAACTAAG GCGAATACTT TCGAAGATGT GTTCGGTGAT
TTTCATGAAG TCACTGGTCT GTAATAA (SEQ ID NO: 36)
Met Ile Leu Lys Ile Leu Asn Glu Ile Ala Ser Ile Gly Ser Thr Lys Gln Lys Gln Ala Ile Leu Glu Lys

Asn Lys Asp Asn Glu Leu Leu Lys Arg Val Tyr Arg Leu Thr Tyr Ser Arg Gly Leu Gln Tyr Tyr Ile Lys

Lys Trp Pro Lys Pro Gly Ile Ala Thr Gln Ser Phe Gly Met Thr Thr Leu Thr Asp Met Leu Asp Phe Ile

Glu Phe Thr Leu Ala Thr Arg Lys Leu Thr Gly Asn Ala Ala Ile Arg Glu Leu Thr Gly Tyr Ile Thr Asp

Gly Lys Lys Asp Asp Val Glu Val Leu Arg Arg Val Met Met Arg Asp Leu Glu Cys Gly Ala Ser Val Ser

Ile Ala Asn Lys Val Trp Lys Gly Leu Ile Pro Glu Gln Pro Gln Met Leu Ala Ser Ser Tyr Asp Glu Lys

Gly Ile Asn Lys Arg Ile Lys Phe Pro Ala Phe Ala Gln Leu Lys Ala Asp Gly Ala Arg Cys Phe Ala Glu

Val Arg Gly Asp Glu Leu Asp Asp Val Arg Leu Leu Ser Arg Ala Gly Asn Glu Tyr Leu Gly Leu Asp Leu

Leu Lys Glu Glu Leu Ile Lys Met Thr Ala Glu Ala Arg Gln Ile His Pro Glu Gly Val Leu Ile Asp Gly

Glu Leu Val Tyr His Glu Gln Val Ala Lys Glu Pro Glu Gly Leu Asp Phe Leu Phe Asp Ala Tyr Pro Pro

Asn Ser Lys Ala Lys Glu Phe Ala Glu Val Ala Glu Ser Arg Thr Ala Ser Asn Gly Ile Ala Asn Lys Ser

Leu Lys Gly Thr Ile Ser Glu Lys Glu Ala Gln Cys Met Lys Phe Gln Val Trp Asp Tyr Val Pro Leu Val

Glu Ile Tyr Ser Leu Pro Ala Phe Arg Leu Lys Tyr Asp Val Arg Phe Ser Lys Leu Glu Gln Met Thr Ser

Gly Tyr Asp Lys Val Ile Leu Ile Glu Asn Gln Val Val Asn Asn Leu Asp Glu Ala Lys Val Ile Tyr Lys
Lys Tyr Ile Asp Gln Gly Leu Glu Gly Ile Ile Leu Lys Asn Ile Asp Gly Leu Trp Glu Asn Ala Arg Ser
Lys Asn Leu Tyr Lys Phe Lys Glu Val Ile Trp Val Asp Leu Lys Ile Val Gly Ile Tyr Pro His Arg Lys
Asp Pro Thr Lys Ala Gly Gly Phe Ile Leu Glu Ser Glu Cys Gly Lys Ile Lys Val Asn Ala Gly Ser Gly
Leu Lys Asp Lys Ala Gly Val Lys Ser His Glu Leu Asp Arg Thr Arg Ile Met Glu Asn Gln Asn Tyr Tyr
Ile Gly Lys Ile Leu Glu Cys Lys Cys Asn Gly Trp Leu Lys Ser Asp Gly Arg Lys Pro Tyr Val Lys Leu
Phe Leu Pro Ile Ala Ile Arg Leu Arg Glu Asp Lys Thr Lys Ala Asn Thr Phe Glu Asp Val Phe Gly Asp
Phe His Glu Val Thr Gly Leu (SEQ ID NO: 37)

ATGATTCTTA AAATTCTGAA CGAAATTGCA AGCATTGGTT CCACTAAACA AAAAAAGCC ATTCTGGAAA AAATAAAGA CAATGAACTG
TTAAAGCGCG TGTATCGCCT GACCTATTCG CGTGGCCTGC AATACTATAT TAAAAAATGG CCCAAACCGG GCATTGCGAC GCAGAGCTTC
GGCATGACTA CCCTGACCGA TATGCTGGAT TTTATCGAGT TTACTCTTGC GACGCGCAAA CTTACCGGCA ACGCTGCTAT TAGAGAATTG
ACGGGCTATA TTACCGATGG CAAAAAGAT GATGTTGAGG TGCTGCGTCG CGTCATGATG CGTGATCTGG AGTGCGGTGC GTCAGTGAGC
ATCGCTAACA AGTGTGGAA GGGTTTGATC CCGGAACAGC CACAGATGCT TGCAAGCAGC TACGATGAAA AGGGCATTAA CAAAAATATC
AAATTTCCGG CTTTCGCCCA GCTGAAAGCG GATGGCGCGC GCTGCTTCGC CGAGGTACGC GGTGACGAAC TGGACGACGT TCGTCTGCTG
TCTCGCGCTG GCAATGAATA TCTGGGTCTG GATCTGCTGA AGAAGAACT GATTAAGATG ACCGCCGAGG CGCGCCAAAT CCACCCCGAA
GGGGTGCTGA TTGATGGCGA ACTGGTGTAT CACGAACAGG TTGCAAAAGA GCCGGAGGGG TTGGATGCTC TGTTTGATCG ATACCCGGAA
AATAGCAAAG CGAAAGAATT TGCGGAAGTG GCGGAATCCC GCACCGCAAG CAATGGTATC GCAAATAAAT CGCTGAAGGG CACCATTTCT
GAGAAAGAAG CACAGTGTAT GAAGTTCCAG GTGTGGGACT ACGTGCCACT GGTTGAGATC TACTCCCTGC CAGCGTTTCG CCTGAAATAC
GATGTGCGTT TTTCAAAACT GGAACAGATG ACGAGCGGAT ATGATAAAGT AATTTTAATC GAGAACCAGG TCGTGAACAA CCTGGATGAA
GCAAAGTTA TCTATAAAAA ATATATTGAT CAGGGCTTAG AAGGCATTAT CCTGAAGAAC ATTGATGGCC TTTGGGAAAA TGCACGCAGC
AAAAACCTGT ATAAATTTAA AGAAGTGATT TGGGTAGATC TGAAGATTGT TGGTATTTAC CCGCATCGCA AGACCCGAC CAAAGCAGGT
GGTTTCATCC TGGAATCTGA ATGCGGTAAA ATTAAAGTGA ACGCAGGCAG TGGTTTGAAA GATAAAGCTG GTGTTAAAAG TCACGAACTG
GATCGCACGC GCATCATGGA AAACCAGAAC TATTATATCG GCAAAATTCT GGAATGCAAA TGCAACGGGT GGCTTAAGAG CGATGGGCGC
AAACCCTATG TGAAATTGTT CCTGCCGATT GCGATTCGCC TTCGCGAAGA CAAAACTAAG GCGAATACTT TCGAAGATGT GTTCGGTGAT
TTTCATGAAG TCACGGGTCT GTAA (SEQ ID NO: 38)

Met Ile Leu Lys Ile Leu Asn Glu Ile Ala Ser Ile Gly Ser Thr Lys Gln Lys Lys Ala Ile Leu Glu Lys
Asn Lys Asp Asn Glu Leu Leu Lys Arg Val Tyr Arg Leu Thr Tyr Ser Arg Gly Leu Gln Tyr Tyr Ile Lys
Lys Trp Pro Lys Pro Gly Ile Ala Thr Gln Ser Phe Gly Met Thr Thr Leu Thr Asp Met Leu Asp Phe Ile
Glu Phe Thr Leu Ala Thr Arg Lys Leu Thr Gly Asn Ala Ala Ile Arg Glu Leu Thr Gly Tyr Ile Thr Asp
Gly Lys Lys Asp Asp Val Glu Val Leu Arg Arg Val Met Met Arg Asp Leu Glu Cys Gly Ala Ser Val Ser
Ile Ala Asn Lys Val Trp Lys Gly Leu Ile Pro Glu Gln Pro Gln Met Leu Ala Ser Ser Tyr Asp Glu Lys
Gly Ile Asn Lys Asn Ile Lys Phe Pro Ala Phe Ala Gln Leu Lys Ala Asp Gly Ala Arg Cys Phe Ala Glu
Val Arg Gly Asp Glu Leu Asp Asp Val Arg Leu Leu Ser Arg Ala Gly Asn Glu Tyr Leu Gly Leu Asp Leu
Leu Lys Glu Glu Leu Ile Lys Met Thr Ala Glu Ala Arg Gln Ile His Pro Glu Gly Val Leu Ile Asp Gly
Glu Leu Val Tyr His Glu Gln Val Ala Lys Glu Pro Glu Gly Leu Asp Ala Leu Phe Asp Arg Tyr Pro Glu
Asn Ser Lys Ala Lys Glu Phe Ala Glu Val Ala Glu Ser Arg Thr Ala Ser Asn Gly Ile Ala Asn Lys Ser
Leu Lys Gly Thr Ile Ser Glu Lys Glu Ala Gln Cys Met Lys Phe Gln Val Trp Asp Tyr Val Pro Leu Val
Glu Ile Tyr Ser Leu Pro Ala Phe Arg Leu Lys Tyr Asp Val Arg Phe Ser Lys Leu Glu Gln Met Thr Ser
Gly Tyr Asp Lys Val Ile Leu Ile Glu Asn Gln Val Val Asn Asn Leu Asp Glu Ala Lys Val Ile Tyr Lys

-continued

Lys Tyr Ile Asp Gln Gly Leu Glu Gly Ile Ile Leu Lys Asn Ile Asp Gly Leu Trp Glu Asn Ala Arg Ser

Lys Asn Leu Tyr Lys Phe Lys Glu Val Ile Trp Val Asp Leu Lys Ile Val Gly Ile Tyr Pro His Arg Lys

Asp Pro Thr Lys Ala Gly Gly Phe Ile Leu Glu Ser Glu Cys Gly Lys Ile Lys Val Asn Ala Gly Ser Gly

Leu Lys Asp Lys Ala Gly Val Lys Ser His Glu Leu Asp Arg Thr Arg Ile Met Glu Asn Gln Asn Tyr Tyr

Ile Gly Lys Ile Leu Glu Cys Lys Cys Asn Gly Trp Leu Lys Ser Asp Gly Arg Lys Pro Tyr Val Lys Leu

Phe Leu Pro Ile Ala Ile Arg Leu Arg Glu Asp Lys Thr Lys Ala Asn Thr Phe Glu Asp Val Phe Gly Asp

Phe His Glu Val Thr Gly Leu (SEQ ID NO: 39)
ATGATTCTTA AAATTCTGAA CGAAATTGCA AGCATTGGTT CCACTAAACA AAACAAGCC ATTCTGGAAA AAATAAAGA CAATGAACTG

TTAAAGCGCG TGTATCGCCT GACCTATTCG CGTGGCCTGC AATACTATAT TAAAAAATGG CCCAAACCGG GCATTGCGAC GCAGAGCTTC

GGCATGCTTA CCCTGACCGA TATGCTGGAT TTTATCGAGT TTACTCTTGC GACGCGCAAA CTTACCGGCA ACGCTGCTAT TAGAAAATTG

ACGGGCTATA TTACCGATGG CAAAAAGAT GATGTTGAGG TGCTGCGTCG CGTCATGATG CGTGATCTGG AGTGCGGTGC GTCAGTGAGC

ATCGCTAACA AAGTGTGGAA GGGTTTGATC CCGGAACAGC CACAGATGCT TGCAAGCAGC TACGATGAAA AGGGCATTAA CAAAAATATC

AAATTTCCGG CTTTCGCCCA GCTGAAAGCG GATGGCGCGC GCTGCTTCGC CGAGGTACGC GGTGACGAAC TGGACGACGT TCGTCTGCTG

TCTCGCGCTG GCAATGAATA TCTGGGTCTG GATCTGCTGA AGAAGAACT GATTAAGATG ACCGCCGAGG CGCGCCAAAT CCACCCCGAA

GGGGTGCTGA TTGATGGCGA ACTGGTGTAT CACGAACAGG TTGCAAAAGA GCCGGAGGGG TTGGATGCTC TGTTTGATCG ATACCCGCCT

AATAGCAAAG CGAAAGAATT TGCGGAAGTG GCGGAATCCC GCACCGCAAG CAATGGTATC GCAAATAAAT CGCTGAAGGG CACCATTTCT

GAGAAAGAAG CACAGTGTAT GAAGTTCCAG GTGTGGGACT ACGTGCCACT GGTTGAGATC TACTCCCTGC CAGCGTTTCG CCTGAAATAC

GATGTGCGTT TTTCAAAACT GGAACAGATG ACGAGCGGAT ATGATAAAGT AATTTTAATC GAGAACCAGG TCGTGAACAA CCTGGATGAA

GCAAAAGTTA TCTATAAAAA ATATATTGAT CAGGGCTTAG AAGGCATTAT CCTGAAGAAC ATTGATGGCC TTTGGGAAAA TGCACGCAGC

AAAAACCTGT ATAAATTTAA AGAAGTGATT GATGTAGATC TGAAGATTGT TGGTATTTAC CCGCATCGCA AAGACCCGAC CAAAGCAGGT

GGTTTCATCC TGGAATCTGA ATGCGGTAAA ATTAAAGTGA ACGCAGGCAG TGGTTTGAAA GATAAAGCTG GTGTTAAAAG TCACGAACTG

GATCGCACGC GCATCATGGA AAACCAGAAC TATTATATCG GCAAAATTCT GGAGTGCAAA TGCAACGGGT GGCTTAAGAG CGCTGGGCGC

AAAGACGGTC TGAAATTGTT CCTGCCGATT GCGATTCGCC TTCGCGAAGA CAAAACTAAG GCGAATACTT TCGAAGATGT GTTCGGTGAT

TTTCATGAAG TCACGGGTCT GTAA (SEQ ID NO: 40)
Met Ile Leu Lys Ile Leu Asn Glu Ile Ala Ser Ile Gly Ser Thr Lys Gln Lys Gln Ala Ile Leu Glu Lys

Asn Lys Asp Asn Glu Leu Leu Lys Arg Val Tyr Arg Leu Thr Tyr Ser Arg Gly Leu Gln Tyr Tyr Ile Lys

Lys Trp Pro Lys Pro Gly Ile Ala Thr Gln Ser Phe Gly Met Leu Thr Leu Thr Asp Met Leu Asp Phe Ile

Glu Phe Thr Leu Ala Thr Arg Lys Leu Thr Gly Asn Ala Ala Ile Arg Lys Leu Thr Gly Tyr Ile Thr Asp

Gly Lys Lys Asp Asp Val Glu Val Leu Arg Arg Val Met Met Arg Asp Leu Glu Cys Gly Ala Ser Val Ser

Ile Ala Asn Lys Val Trp Lys Gly Leu Ile Pro Glu Gln Pro Gln Met Leu Ala Ser Ser Tyr Asp Glu Lys

Gly Ile Asn Lys Asn Ile Lys Phe Pro Ala Phe Ala Gln Leu Lys Ala Asp Gly Ala Arg Cys Phe Ala Glu

Val Arg Gly Asp Glu Leu Asp Asp Val Arg Leu Leu Ser Arg Ala Gly Asn Glu Tyr Leu Gly Leu Asp Leu

Leu Lys Glu Glu Leu Ile Lys Met Thr Ala Glu Ala Arg Gln Ile His Pro Glu Gly Val Leu Ile Asp Gly

Glu Leu Val Tyr His Glu Gln Val Ala Lys Glu Pro Glu Gly Leu Asp Ala Leu Phe Asp Arg Tyr Pro Pro

Asn Ser Lys Ala Lys Glu Phe Ala Glu Val Ala Glu Ser Arg Thr Ala Ser Asn Gly Ile Ala Asn Lys Ser

Leu Lys Gly Thr Ile Ser Glu Lys Glu Ala Gln Cys Met Lys Phe Gln Val Trp Asp Tyr Val Pro Leu Val

Glu Ile Tyr Ser Leu Pro Ala Phe Arg Leu Lys Tyr Asp Val Arg Phe Ser Lys Leu Glu Gln Met Thr Ser

Gly Tyr Asp Lys Val Ile Leu Ile Glu Asn Gln Val Val Asn Asn Leu Asp Glu Ala Lys Val Ile Tyr Lys

Lys Tyr Ile Asp Gln Gly Leu Glu Gly Ile Ile Leu Lys Asn Ile Asp Gly Leu Trp Glu Asn Ala Arg Ser

Lys Asn Leu Tyr Lys Phe Lys Glu Val Ile Asp Val Asp Leu Lys Ile Val Gly Ile Tyr Pro His Arg Lys

Asp Pro Thr Lys Ala Gly Gly Phe Ile Leu Glu Ser Glu Cys Gly Lys Ile Lys Val Asn Ala Gly Ser Gly

Leu Lys Asp Lys Ala Gly Val Lys Ser His Glu Leu Asp Arg Thr Arg Ile Met Glu Asn Gln Asn Tyr Tyr

Ile Gly Lys Ile Leu Glu Cys Lys Cys Asn Gly Trp Leu Lys Ser Ala Gly Arg Lys Asp Gly Leu Lys Leu

Phe Leu Pro Ile Ala Ile Arg Leu Arg Glu Asp Lys Thr Lys Ala Asn Thr Phe Glu Asp Val Phe Gly Asp

Phe His Glu Val Thr Gly Leu (SEQ ID NO: 41)
```
ATGATTCTTA AAATTCTGAA CGAAATTGCA AGCATTGGTT CCACTAAACA AAACAAGCC ATTCTGGAAA AAATAAAGA CAATGAACTG
TTAAAGCGCG TGTATCGCCT GACCTATTCG CGTGGCCTGC AATACTATAT TAAAAAATGG CCCAAACCGG GCATTGCGAC GCAGAGCTTC
GGCATGCTTA CCCTGACCGA TATGCTGGAT TTTATCGAGT TTACTCTTGC GACGCGCAAA CTTACCGGCA ACGCTGCTAT TAGAGAATTG
ACGGGCTATA TTACCGATGG CAAAAAGAT GATGTTGAGG TGCTGCGTCG CGTCATGATG CGTGATCTGG AGTGCGGTGC GTCAGTGAGC
ATCGCTAACA AAGTGTGGAA GGGTTTGATC CCGGAACAGC CACAGATGCT TGCAAGCAGC TACGATGAAA AGGGCATTAA CAAAAGAATC
AAATTTCCGG CTTTCGCCCA GCTGAAAGCG GATGGCGCGC GCTGCTTCGC CGAGGTACGC GGTGACGAAC TGGACGACGT TCGTCTGCTG
TCTCGCGCTG GCAATGAATA TCTGGGTCTG GATCTGCTGA AGAAGAACT GATTAAGATG ACCGCCGAGG CGCGCCAAAT CCACCCCGAA
GGGGTGCTGA TTGATGGCGA ACTGGTGTAT CACGAACAGG TTGCAAAAGA GCCGGAGGGG TTGGATGCTC TGTTTGATAA TTACCCGGAA
AATAGCAAAG CGAAAGAATT TGCGGAAGTG GCGGAATCCC GCACCGCAAG CAATGGTATC GCAAATAAAT CGCTGAAGGG CACCATTTCT
GAGAAAGAAG CACAGTGTAT GAAGTTCCAG GTGTGGACT ACGTGCCACT GGTTGAGATC TACTCCCTGC CAGCGTTTCG CCTGAAATAC
GATGTGCGTT TTTCAAAACT GGAACAGATG ACGAGCGGAT ATGATAAAGT AATTTTAATC GAGAACCAGG TCGTGAACAA CCTGGATGAA
GCAAAGTTA TCTATAAAAA ATATATTGAT CAGGGCTTAG AAGGCATTAT CCTGAAGAAC ATTGATGGCC TTTGGGAAAA TGCACGCAGC
AAAAACCTGT ATAAATTTAA AGAAGTGATT GATGTAGATC TGAAGATTGT TGGTATTTAC CCGCATCGCA AAGACCCGAC CAAAGCAGGT
GGTTTCATCC TGGAATCTGA ATGCGGTAAA ATTAAGTGA ACGCAGGCAG TGGTTTGAAA GATAAAGCTG GTGTTAAAAG TCACGAACTG
GATCGCACGC GCATCATGGA AAACCAGAAC TATTATATCG GCAAAATTCT GGAGTGCAAA TGCAACGGGT GGCTTAAGAG CGATGGGCGC
AAAGACTATC TGAAATTGTT CCTGCCGATT GCGATTCGCC TTCGCGAAGA CAAAACTAAG GCGAATACTT TCGAAGATGT GTTCGGTGAT
TTTCATGAAG TCACGGGTCT GTAA
```

(SEQ ID NO: 42)
Met Ile Leu Lys Ile Leu Asn Glu Ile Ala Ser Ile Gly Ser Thr Lys Gln Lys Gln Ala Ile Leu Glu Lys

Asn Lys Asp Asn Glu Leu Leu Lys Arg Val Tyr Arg Leu Thr Tyr Ser Arg Gly Leu Gln Tyr Tyr Ile Lys

Lys Trp Pro Lys Pro Gly Ile Ala Thr Gln Ser Phe Gly Met Leu Thr Leu Thr Asp Met Leu Asp Phe Ile

Glu Phe Thr Leu Ala Thr Arg Lys Leu Thr Gly Asn Ala Ala Ile Arg Glu Leu Thr Gly Tyr Ile Thr Asp

Gly Lys Lys Asp Asp Val Glu Val Leu Arg Arg Val Met Met Arg Asp Leu Glu Cys Gly Ala Ser Val Ser

Ile Ala Asn Lys Val Trp Lys Gly Leu Ile Pro Glu Gln Pro Gln Met Leu Ala Ser Ser Tyr Asp Glu Lys

Gly Ile Asn Lys Arg Ile Lys Phe Pro Ala Phe Ala Gln Leu Lys Ala Asp Gly Ala Arg Cys Phe Ala Glu

Val Arg Gly Asp Glu Leu Asp Asp Val Arg Leu Leu Ser Arg Ala Gly Asn Glu Tyr Leu Gly Leu Asp Leu

Leu Lys Glu Glu Leu Ile Lys Met Thr Ala Glu Ala Arg Gln Ile His Pro Glu Gly Val Leu Ile Asp Gly

Glu Leu Val Tyr His Glu Gln Val Ala Lys Glu Pro Glu Gly Leu Asp Ala Leu Phe Asp Asn Tyr Pro Glu

Asn Ser Lys Ala Lys Glu Phe Ala Glu Val Ala Glu Ser Arg Thr Ala Ser Asn Gly Ile Ala Asn Lys Ser

Leu Lys Gly Thr Ile Ser Glu Lys Glu Ala Gln Cys Met Lys Phe Gln Val Trp Asp Tyr Val Pro Leu Val

Glu Ile Tyr Ser Leu Pro Ala Phe Arg Leu Lys Tyr Asp Val Arg Phe Ser Lys Leu Glu Gln Met Thr Ser

Gly Tyr Asp Lys Val Ile Leu Ile Glu Asn Gln Val Val Asn Asn Leu Asp Glu Ala Lys Val Ile Tyr Lys

Lys Tyr Ile Asp Gln Gly Leu Glu Gly Ile Ile Leu Lys Asn Ile Asp Gly Leu Trp Glu Asn Ala Arg Ser

Lys Asn Leu Tyr Lys Phe Lys Glu Val Ile Asp Val Asp Leu Lys Ile Val Gly Ile Tyr Pro His Arg Lys

Asp Pro Thr Lys Ala Gly Gly Phe Ile Leu Glu Ser Glu Cys Gly Lys Ile Lys Val Asn Ala Gly Ser Gly

-continued

Leu Lys Asp Lys Ala Gly Val Lys Ser His Glu Leu Asp Arg Thr Arg Ile Met Glu Asn Gln Asn Tyr Tyr
Ile Gly Lys Ile Leu Glu Cys Lys Cys Asn Gly Trp Leu Lys Ser Asp Gly Arg Lys Asp Tyr Leu Lys Leu
Phe Leu Pro Ile Ala Ile Arg Leu Arg Glu Asp Lys Thr Lys Ala Asn Thr Phe Glu Asp Val Phe Gly Asp
Phe His Glu Val Thr Gly Leu (SEQ ID NO: 43)
ATGATTCTTA AAATTCTGAA CGAAATTGCA AGCATTGGTT CCACTAAACA AAACAAGCC ATTCTGGAAA AAAATAAAGA CAATGAACTG
TTAAAGCGCG TGTATCGCCT GACCTATTCG CGTGGCCTGC AATACTATAT TAAAAAATGG CCCAAACCGG GCATTGCGAC GCAGAGCTTC
GGCATGCTGA CCCTGACCGA TATGCTGGAT TTTATCGAGT TTACTCTTGC GACGCGCAAA CTTACCGGCA ACGCTCGGAT TAGAAAATTG
ACGGGCTATA TTACCGATGG CAAAAAAGAT GATGTTGAGG TGCTGCGTCG CGTCATGATG CGTGATCTGG AGTGCGGTGC GTCAGTGAGC
ATCGCTAACA AAGTGTGGAA GGGTTTGATC CCGGAACAGC CACAGATGCT TGCAAGCAGC TACGATGAAA AGGGCATTAA CAAAAGAATC
AAATTTCCGG CTTTCGCCCA GCTGAAAGCG GATGGCGCGC GCTGCTTCGC CGAGGTACGC GGTGACGAAC TGGACGACGT TCGTCTGCTG
TCTCGCGCTG GCAATGAATA TCTGGGTCTG GATCTGCTGA AGAAGAACT GATTAAGATG ACCGCCGAGG CGCGCCAAAT CCACCCCGAA
GGGGTGCTGA TTGATGGCGA ACTGGTGTAT CACGAACAGG TTGCAAAAGA GCCGGAGGGG TTGGATGCTC TGTTTGATAA TTACCCGCCT
AATAGCAAAG CGAAAGAATT TGCGGAAGTG GCGGAATCCC GCACCGCAAG CAATGGTATC GCAAATAAAT CGCTGAAGGG CACCATTTCT
GAGAAAGAAG CACAGTGTAT GAAGTTCCAG GTGTGGGACT ACGTGCCACT GGTTGAGATC TACTCCCTGC CAGCGTTTCG CCTGAAATAC
GATGTGCGTT TTTCAAAACT GGAACAGATG ACGAGCGGAT ATGATAAAGT AATTTTAATC GAGAACCAGG TCGTGAACAA CCTGGATGAA
GCAAAGTTA TCTATAAAAA ATATATTGAT CAGGGCTTAG AAGGCATTAT CCTGAAGAAC ATTGATGGCC TTTGGGAAAA TGCACGCAGC
AAAAACCTGT ATAAATTTAA AGAAGTGATT GATGTAGATC TGAAGATTGT TGGTATTTAC CCGCATCGCA AAGACCCGAC CAAAGCAGGT
GGTTTCATCC TGGAATCTGA ATGCGGTAAA ATTAAAGTGA ACGCAGGCAG TGGTTTGAAA GATAAAGCTG GTGTTAAAAG TCACGAACTG
GATCGCACGC GCATCATGGA AAACCAGAAC TATTATATCG GCAAAATTCT GGAGTGCAAA TGCAACGGGT GGCTTAAGAG CGATGGGCGC
AAAGACTATG TTAAATTGTT CCTGCCGATT GCGATTCGCC TTCGCGAAGA CAAAACTAAG GCGAATACTT TCGAAGATGT GTTCGGTGAT
TTTCATGAAG TCACGGGTCT GTAA (SEQ ID NO: 44)
Met Ile Leu Lys Ile Leu Asn Glu Ile Ala Ser Ile Gly Ser Thr Lys Gln Lys Gln Ala Ile Leu Glu Lys
Asn Lys Asp Asn Glu Leu Leu Lys Arg Val Tyr Arg Leu Thr Tyr Ser Arg Gly Leu Gln Tyr Tyr Ile Lys
Lys Trp Pro Lys Pro Gly Ile Ala Thr Gln Ser Phe Gly Met Leu Thr Leu Thr Asp Met Leu Asp Phe Ile
Glu Phe Thr Leu Ala Thr Arg Lys Leu Thr Gly Asn Ala Arg Ile Arg Lys Leu Thr Gly Tyr Ile Thr Asp
Gly Lys Lys Asp Asp Val Glu Val Leu Arg Arg Val Met Met Arg Asp Leu Glu Cys Gly Ala Ser Val Ser
Ile Ala Asn Lys Val Trp Lys Gly Leu Ile Pro Glu Gln Pro Gln Met Leu Ala Ser Ser Tyr Asp Glu Lys
Gly Ile Asn Lys Arg Ile Lys Phe Pro Ala Phe Ala Gln Leu Lys Ala Asp Gly Ala Arg Cys Phe Ala Glu
Val Arg Gly Asp Glu Leu Asp Asp Val Arg Leu Leu Ser Arg Ala Gly Asn Glu Tyr Leu Gly Leu Asp Leu
Leu Lys Glu Glu Leu Ile Lys Met Thr Ala Glu Ala Arg Gln Ile His Pro Glu Gly Val Leu Ile Asp Gly
Glu Leu Val Tyr His Glu Gln Val Ala Lys Glu Pro Glu Gly Leu Asp Ala Leu Phe Asp Asn Tyr Pro Pro
Asn Ser Lys Ala Lys Glu Phe Ala Glu Val Ala Glu Ser Arg Thr Ala Ser Asn Gly Ile Ala Asn Lys Ser
Leu Lys Gly Thr Ile Ser Glu Lys Glu Ala Gln Cys Met Lys Phe Gln Val Trp Asp Tyr Val Pro Leu Val
Glu Ile Tyr Ser Leu Pro Ala Phe Arg Leu Lys Tyr Asp Val Arg Phe Ser Lys Leu Glu Gln Met Thr Ser
Gly Tyr Asp Lys Val Ile Leu Ile Glu Asn Gln Val Val Asn Asn Leu Asp Glu Ala Lys Val Ile Tyr Lys
Lys Tyr Ile Asp Gln Gly Leu Glu Gly Ile Ile Leu Lys Asn Ile Asp Gly Leu Trp Glu Asn Ala Arg Ser
Lys Asn Leu Tyr Lys Phe Lys Glu Val Ile Asp Val Asp Leu Lys Ile Val Gly Ile Tyr Pro His Arg Lys
Asp Pro Thr Lys Ala Gly Gly Phe Ile Leu Glu Ser Glu Cys Gly Lys Ile Lys Val Asn Ala Gly Ser Gly
Leu Lys Asp Lys Ala Gly Val Lys Ser His Glu Leu Asp Arg Thr Arg Ile Met Glu Asn Gln Asn Tyr Tyr
Ile Gly Lys Ile Leu Glu Cys Lys Cys Asn Gly Trp Leu Lys Ser Asp Gly Arg Lys Asp Tyr Val Lys Leu

-continued

Phe Leu Pro Ile Ala Ile Arg Leu Arg Glu Asp Lys Thr Lys Ala Asn Thr Phe Glu Asp Val Phe Gly Asp

Phe His Glu Val Thr Gly Leu (SEQ ID NO: 45)

ATGATTCTTA AAATTCTGAA CGAAATTGCA AGCATTGGTT CCACTAAACA AAAAAAGCC ATTCTGGAAA AAATAAAGA CAATGAACTG

TTAAAGCGCG TGTATCGCCT GACCTATTCG CGTGGCCTGC AATACTATAT TAAAAAATGG CCCAAACCGG GCATTGCGAC GCAGAGCTTC

GGCATGACTA CCCTGACCGA TATGCTGGAT TTTATCGAGT TTACTCTTGC GACGCGCAAA CTTACCGGCA ACGCTGCTAT TAGAGAATTG

ACGGGCTATA TTACCGATGG CAAAAAGAT GATGTTGAGG TGCTGCGTCG CGTCATGATG CGTGATCTGG AGTGCGGTGC GTCAGTGAGC

ATCGCTAACA AGTGTGGAA GGGTTTGATC CCGGAACAGC CACAGATGCT TGCAAGCAGC TACGATGAAA AGGGCATTAA CAAAAACATC

AAATTTCCGG CTTTCGCCCA GCTGAAAGCG GATGGCGCGC GCTGCTTCGC CGAGGTACGC GGTGACGAAC TGGACGACGT TCGTCTGCTG

TCTCGCAAAG GTAATGAATA TCTGGGTCTG GATCTGCTGA AGAAGAACT GATTAAGATG ACCGCCGAGG CGCGCCAAAT CCACCCCGAA

GGGGTGCTGA TTGATGGCGA ACTGGTGTAT CACGAACAGG TTGCAAAAGA GCCGGAGGGG AAAGACGCTC TGTTTGATCG ATACCCGGAA

AATAGCAAAG CGAAAGAATT TGCGGAAGTG GCGGAATCCC GCACCGCAAG CAATGGTATC GCAAATAAAT CGCTGAAGGG CACCATTTCT

GAGAAAGAAG CACAGTGTAT GAAGTTCCAG GTGTGGGACT ACGTGCCACT GGTTGAGATC TACTCCCTGC CAGCGTTTCG CCTGAAATAC

GATGTGCGTT TTTCAAAACT GGAACAGATG ACGAGCGGAT ATGATAAAGT AATTTTAATC GAGAACCAGG TCGTGAACAA CCTGGATGAA

GCAAAGTTA TCTATAAAAA ATATATTGAT CAGGGCTTAG AAGGCATTAT CCTGAAGAAC ATTGATGGCC TTTGGGAAAA TGCACGCAGC

AAAAACCTGT ATAAATTTAA AGAAGTGATT TGGGTAGATC TGAAGATTGT TGGTATTTAC CCGCATCGCA AGACCCTAC CAAAGCAGGT

GGTTTCATCC TGGAATCTGA ATGCGGTAAA ATTAAAGTGA ACGCAGGCAG TGGTTTGAAA GATAAAGCTG GTGTTAAAAG TCACGAACTG

GATCGCACGC GCATCATGCG GAACCAGAAC TATTATATCG GCAAAATTCT GGAATGCAAA TGCAACGGGT GGCTTAAGAG CGATGGGCGC

AAGCCCTATG TGAAATTGTT CCTGCCGATT GCGATTCGCC TTCGCGGAGA CAAAACTAAG GCGAATACTT TCGAAGATGT GTTCGGTGAT

TTTCATGAAG TCACGGGTCT GTAA (SEQ ID NO: 46)

Met Ile Leu Lys Ile Leu Asn Glu Ile Ala Ser Ile Gly Ser Thr Lys Gln Lys Lys Ala Ile Leu Glu Lys

Asn Lys Asp Asn Glu Leu Leu Lys Arg Val Tyr Arg Leu Thr Tyr Ser Arg Gly Leu Gln Tyr Tyr Ile Lys

Lys Trp Pro Lys Pro Gly Ile Ala Thr Gln Ser Phe Gly Met Thr Thr Leu Thr Asp Met Leu Asp Phe Ile

Glu Phe Thr Leu Ala Thr Arg Lys Leu Thr Gly Asn Ala Ala Ile Arg Glu Leu Thr Gly Tyr Ile Thr Asp

Gly Lys Lys Asp Asp Val Glu Val Leu Arg Arg Val Met Met Arg Asp Leu Glu Cys Gly Ala Ser Val Ser

Ile Ala Asn Lys Val Trp Lys Gly Leu Ile Pro Glu Gln Pro Gln Met Leu Ala Ser Ser Tyr Asp Glu Lys

Gly Ile Asn Lys Asn Ile Lys Phe Pro Ala Phe Ala Gln Leu Lys Ala Asp Gly Ala Arg Cys Phe Ala Glu

Val Arg Gly Asp Glu Leu Asp Asp Val Arg Leu Leu Ser Arg Lys Gly Asn Glu Tyr Leu Gly Leu Asp Leu

Leu Lys Glu Glu Leu Ile Lys Met Thr Ala Glu Ala Arg Gln Ile His Pro Glu Gly Val Leu Ile Asp Gly

Glu Leu Val Tyr His Glu Gln Val Ala Lys Glu Pro Glu Gly Lys Asp Ala Leu Phe Asp Arg Tyr Pro Glu

Asn Ser Lys Ala Lys Glu Phe Ala Glu Val Ala Glu Ser Arg Thr Ala Ser Asn Gly Ile Ala Asn Lys Ser

Leu Lys Gly Thr Ile Ser Glu Lys Glu Ala Gln Cys Met Lys Phe Gln Val Trp Asp Tyr Val Pro Leu Val

Glu Ile Tyr Ser Leu Pro Ala Phe Arg Leu Lys Tyr Asp Val Arg Phe Ser Lys Leu Glu Gln Met Thr Ser

Gly Tyr Asp Lys Val Ile Leu Ile Glu Asn Gln Val Val Asn Asn Leu Asp Glu Ala Lys Val Ile Tyr Lys

Lys Tyr Ile Asp Gln Gly Leu Glu Gly Ile Ile Leu Lys Asn Ile Asp Gly Leu Trp Glu Asn Ala Arg Ser

Lys Asn Leu Tyr Lys Phe Lys Glu Val Ile Trp Val Asp Leu Lys Ile Val Gly Ile Tyr Pro His Arg Lys

Asp Pro Thr Lys Ala Gly Gly Phe Ile Leu Glu Ser Glu Cys Gly Lys Ile Lys Val Asn Ala Gly Ser Gly

Leu Lys Asp Lys Ala Gly Val Lys Ser His Glu Leu Asp Arg Thr Arg Ile Met Arg Asn Gln Asn Tyr Tyr

Ile Gly Lys Ile Leu Glu Cys Lys Cys Asn Gly Trp Leu Lys Ser Asp Gly Arg Lys Pro Tyr Val Lys Leu

-continued

Phe Leu Pro Ile Ala Ile Arg Leu Arg Gly Asp Lys Thr Lys Ala Asn Thr Phe Glu Asp Val Phe Gly Asp

Phe His Glu Val Thr Gly Leu (SEQ ID NO: 47)

ATGATTCTTA AAATTCTGAA CGAAATTGCA AGCATTGGTT CCACTAAACA AAAAAAGCC ATTCTGGAAA AAAATAAAGA CAATGAACTG

TTAAAGCGCG TGTATCGCCT GACCTATTCG CGTGGCCTGC AATACTATAT TAAAAAATGG CCCAAACCGG GCATTGCGAC GCAGAGCTTC

GGCATGACTA CCCTGACCGA TATGCTGGAT TTTATCGAGT TTACTCTTGC GACGCGCAAA CTTACCGGCA ACGCTGCTAT TAGAGAATTG

ACGGGCTATA TTACCGATGG CAAAAAGAT GATGTTGAGG TGCTGCGTCG CGTCATGATG CGTGATCTGG AGTGCGGTGC GTCAGTGAGC

ATCGCTAACA AGTGTGGAA GGGTTTGATC CCGGAACAGC CACAGATGCT TGCAAGCAGC TACGATGAAA AGGGCATTAA CAAAAATATC

AAATTTCCGG CTTTCGCCCA GCTGAAAGCG GATGGCGCGC GCTGCTTCGC CGAGGTACGC GGTGACGAAC TGGACGACGT TCGTCTGCTG

TCTCGCGCTG GCAATGAATA TCTGGGTCTG GATCTGCTGA AGAAGAACT GATTAAGATG ACCGCCGAGG CGCGCCAAAT CCACCCCGAA

GGGGTGCTGA TTGATGGCGA ACTGGTGTAT CACGAACAGG TTGCAAAAGA GCCGGAGGGG TTGGATGCTC TGTTTGATCG ATACCCGGAA

AATAGCAAAG CGAAAGAATT TGCGGAAGTG GCGGAATCCC GCACCGCAAG CAATGGTATC GCAAATAAAT CGCTGAAGGG CACCATTTCT

GAGAAAGAAG CACAGTGTAT GAAGTTCCAG GTGTGGACT ACGTGCCACT GGTTGAGATC TACTCCCTGC CAGCGTTTCG CCTGAAATAC

GATGTGCGTT TTTCAAAACT GGAACAGATG ACGAGCGGAT ATGATAAAGT AATTTTAATC GAGAACCAGG TCGTGAACAA CCTGGATGAA

GCAAAAGTTA TCTATAAAAA ATATATTGAT CAGGGCTTAG AAGGCATTAT CCTGAAGAAC ATTGATGGCC TTTGGGAAAA TGCACGCAGC

AAAAACCTGT ATAAATTTAA AGAAGTGATT TGGGTAGATC TGAAGATTGT TGGTATTTAC CCGCATCGCA AAAAACCTAC CAAAGCAGGT

GGTTTCATCC TGGAATCTGA ATGCGGTAAA ATTAAAGTGA ACGCAGGCAG TGGTTTGAAA GATAAAGCAG GTGTTAAAAG TCACGAACTG

GATCGCACGC GCATCATGGA GAACCAGAAC TATTATATCG GCAAAATTCT GGAATGCAAA TGCAACGGGT GGCTTAAGAG CGATGGGCGC

AAGCCCCGTG TGAAATTGTT CCTGCCGATT GCGATTCGCC TTCGCGGAGA CAAAACTAAG GCGAATACTT TCGAAGATGT GTTCGGTGAT

TTTCATGAAG TCACGGGTCT GTAA (SEQ ID NO: 48)

Met Ile Leu Lys Ile Leu Asn Glu Ile Ala Ser Ile Gly Ser Thr Lys Gln Lys Lys Ala Ile Leu Glu Lys

Asn Lys Asp Asn Glu Leu Leu Lys Arg Val Tyr Arg Leu Thr Tyr Ser Arg Gly Leu Gln Tyr Tyr Ile Lys

Lys Trp Pro Lys Pro Gly Ile Ala Thr Gln Ser Phe Gly Met Thr Leu Thr Asp Met Leu Asp Phe Ile Glu

Phe Thr Leu Ala Thr Arg Lys Leu Thr Gly Asn Ala Ala Ile Arg Glu Leu Thr Gly Tyr Ile Thr Asp Gly

Lys Lys Asp Asp Val Glu Val Leu Arg Arg Val Met Met Arg Asp Leu Glu Cys Gly Ala Ser Val Ser Ile

Ala Asn Lys Val Trp Lys Gly Leu Ile Pro Glu Gln Pro Gln Met Leu Ala Ser Ser Tyr Asp Glu Lys Gly

Ile Asn Lys Asn Ile Lys Phe Pro Ala Phe Ala Gln Leu Lys Ala Asp Gly Ala Arg Cys Phe Ala Glu Val

Arg Gly Asp Glu Leu Asp Asp Val Arg Leu Leu Ser Arg Ala Gly Asn Glu Tyr Leu Gly Leu Asp Leu Leu

Lys Glu Glu Leu Ile Lys Met Thr Ala Glu Ala Arg Gln Ile His Pro Glu Gly Val Leu Ile Asp Gly Glu

Leu Val Tyr His Glu Gln Val Ala Lys Glu Pro Glu Gly Leu Asp Ala Leu Phe Asp Arg Tyr Pro Glu Asn

Ser Lys Ala Lys Glu Phe Ala Glu Val Ala Glu Ser Arg Thr Ala Ser Asn Gly Ile Ala Asn Lys Ser Leu

Lys Gly Thr Ile Ser Glu Lys Glu Ala Gln Cys Met Lys Phe Gln Val Trp Asp Tyr Val Pro Leu Val Glu

Ile Tyr Ser Leu Pro Ala Phe Arg Leu Lys Tyr Asp Val Arg Phe Ser Lys Leu Glu Gln Met Thr Ser Gly

Tyr Asp Lys Val Ile Leu Ile Glu Asn Gln Val Val Asn Asn Leu Asp Glu Ala Lys Val Ile Tyr Lys Lys

Tyr Ile Asp Gln Gly Leu Glu Gly Ile Ile Leu Lys Asn Ile Asp Gly Leu Trp Glu Asn Ala Arg Ser Lys

Asn Leu Tyr Lys Phe Lys Glu Val Ile Trp Val Asp Leu Lys Ile Val Gly Ile Tyr Pro His Arg Lys Lys

Pro Thr Lys Ala Gly Gly Phe Ile Leu Glu Ser Glu Cys Gly Lys Ile Lys Val Asn Ala Gly Ser Gly Leu

Lys Asp Lys Ala Gly Val Lys Ser His Glu Leu Asp Arg Thr Arg Ile Met Glu Asn Gln Asn Tyr Tyr Ile

-continued

Gly Lys Ile Leu Glu Cys Lys Cys Asn Gly Trp Leu Lys Ser Asp Gly Arg Lys Pro Arg Val Lys Leu Phe

Leu Pro Ile Ala Ile Arg Leu Arg Gly Asp Lys Thr Lys Ala Asn Thr Phe Glu Asp Val Phe Gly Asp Phe

His Glu Val Thr Gly Leu (SEQ ID NO: 49)

ATGATTCTTA AAATTCTGAA CGAAATTGCA AGCATTAAGT CCACTAAACA AAAAAAGCC ATTCTGGAAA AAATAAAGA CAATGAACTG

TTAAAGCGCG TGTATCGCCT GACCTATTCG CGTGGCCTGC AATACTATAT TAAAAAATGG CCCAAACCGG GCATTGCGAC GCAGAGCTTC

GGCATGACTA CCCTGACCGA TATGCTGGAT TTTATCGAGT TTACTCTTGC GACGCGCAAA CTTACCGGCA ACGCTGCTAT TAGAGAATTG

ACGGGCTATA TTACCGATGG CAAAAAAGAT GATGTTGAGG TGCTGCGTCG CGTCATGATG CGTGATCTGG AGTGCGGTGC GTCAGTGAGC

ATCGCTAACA AAGTGTGGAA GGGTTTGATC CCGGAACAGC CACAGATGCT TGCAAGCAGC TACGATGAAA AGGGCATTAA CAAAAACATC

AAATTTCCGG CTTTCGCCCA GCTGAAAGCG GATGGCGCGC GCTGCTTCGC CGAGGTACGC GGTGACGAAC TGGACGACGT TCGTCTGCTG

TCTCGCAAAG GTAATGAATA TCTGGGTCTG GATCTGCTGA AGAAGAACT GATTAAGATG ACCGCCGAGG CGCGCCAAAT CCACCCCGAA

GGGGTGCTGA TTGATGGCGA ACTGGTGTAT CACGAACAGG TTGCAAAAGA GCCGGAGGGG TTAAAAGCTC TGTTTGATCG ATACCCGGAA

AATAGCAAAG CGAAAGAATT TGCGGAAGTG GCGGAATCCC GCACCGCAAG CAATGGTATC GCAAATAAAT CGCTGAAGGG CACCATTTCT

GAGAAAGAAG CACAGTGTAT GAAGTTCCAG GTGTGGGACT ACGTGCCACT GGTTGAGATC TACTCCCTGC CAGCGTTTCG CCTGAAATAC

GATGTGCGTT TTTCAAAACT GGAACAGATG ACGAGCGGAT ATGATAAAGT AATTTTAATC GAGAACCAGG TCGTGAACAA CCTGGATGAA

GCAAAGTTA TCTATAAAAA ATATATTGAT CAGGGCTTAG AAGGCATTAT CCTGAAGAAC ATTGATGGCC TTTGGGAAAA TGCACGCAGC

AAAAACCTGT ATAAATTTAA AGAAGTGATT TGGGTAGATC TGAAGATTGT TGGTATTTAC CCGCATCGCA AAGACAAAAC CAAAGCAGGT

GGTTTCATCC TGGAATCTGA ATGCGGTAAA ATTAAAGTGA ACGCAGGCAG TGGTTTGAAA GATAAAGCTG GTGTTAAAAG TCACGAACTG

GATCGCACGC GCATCATGGA GAACCAGAAC TATTATATCG GCAAAATTCT GGAATGCAAA TGCAACGGGT GGCTTAAGAG CGATGGGCGC

GGTCCCTATG TGAAATTGTT CCTGCCGATT GCGATTCGCC TTCGCGAAGA CAAAACTAAG GCGAATACTT TCGAAGATGT GTTCGGTGAT

TTTCATGAAG TCACGGGTCT GTAA (SEQ ID NO: 50)

Met Ile Leu Lys Ile Leu Asn Glu Ile Ala Ser Ile Lys Ser Thr Lys Gln Lys Lys Ala Ile Leu Glu Lys

Asn Lys Asp Asn Glu Leu Leu Lys Arg Val Tyr Arg Leu Thr Tyr Ser Arg Gly Leu Gln Tyr Tyr Ile Lys

Lys Trp Pro Lys Pro Gly Ile Ala Thr Gln Ser Phe Gly Met Thr Thr Leu Thr Asp Met Leu Asp Phe Ile

Glu Phe Thr Leu Ala Thr Arg Lys Leu Thr Gly Asn Ala Ala Ile Arg Glu Leu Thr Gly Tyr Ile Thr Asp

Gly Lys Lys Asp Asp Val Glu Val Leu Arg Arg Val Met Met Arg Asp Leu Glu Cys Gly Ala Ser Val Ser

Ile Ala Asn Lys Val Trp Lys Gly Leu Ile Pro Glu Gln Pro Gln Met Leu Ala Ser Ser Tyr Asp Glu Lys

Gly Ile Asn Lys Asn Ile Lys Phe Pro Ala Phe Ala Gln Leu Lys Ala Asp Gly Ala Arg Cys Phe Ala Glu

Val Arg Gly Asp Glu Leu Asp Asp Val Arg Leu Leu Ser Arg Lys Gly Asn Glu Tyr Leu Gly Leu Asp Leu

Leu Lys Glu Glu Leu Ile Lys Met Thr Ala Glu Ala Arg Gln Ile His Pro Glu Gly Val Leu Ile Asp Gly

Glu Leu Val Tyr His Glu Gln Val Ala Lys Glu Pro Glu Gly Leu Lys Ala Leu Phe Asp Arg Tyr Pro Glu

Asn Ser Lys Ala Lys Glu Phe Ala Glu Val Ala Glu Ser Arg Thr Ala Ser Asn Gly Ile Ala Asn Lys Ser

Leu Lys Gly Thr Ile Ser Glu Lys Glu Ala Gln Cys Met Lys Phe Gln Val Trp Asp Tyr Val Pro Leu Val

Glu Ile Tyr Ser Leu Pro Ala Phe Arg Leu Lys Tyr Asp Val Arg Phe Ser Lys Leu Glu Gln Met Thr Ser

Gly Tyr Asp Lys Val Ile Leu Ile Glu Asn Gln Val Val Asn Asn Leu Asp Glu Ala Lys Val Ile Tyr Lys

Lys Tyr Ile Asp Gln Gly Leu Glu Gly Ile Ile Leu Lys Asn Ile Asp Gly Leu Trp Glu Asn Ala Arg Ser

Lys Asn Leu Tyr Lys Phe Lys Glu Val Ile Trp Val Asp Leu Lys Ile Val Gly Ile Tyr Pro His Arg Lys

-continued

Asp Lys Thr Lys Ala Gly Gly Phe Ile Leu Glu Ser Glu Cys Gly Lys Ile Lys Val Asn Ala Gly Ser Gly

Leu Lys Asp Lys Ala Gly Val Lys Ser His Glu Leu Asp Arg Thr Arg Ile Met Glu Asn Gln Asn Tyr Tyr

Ile Gly Lys Ile Leu Glu Cys Lys Cys Asn Gly Trp Leu Lys Ser Asp Gly Arg Gly Pro Tyr Val Lys Leu

Phe Leu Pro Ile Ala Ile Arg Leu Arg Glu Asp Lys Thr Lys Ala Asn Thr Phe Glu Asp Val Phe Gly Asp

Phe His Glu Val Thr Gly Leu (SEQ ID NO: 51)

```
ATGATTCTTA AAATTCTGAA CGAAATTGCA AGCATTGGTT CCACTAAACA AAAAAAGCC ATTCTGGAAA AAATAAAGA CAATGAACTG
TTAAAGCGCG TGTATCGCCT GACCTATTCG CGTGGCCTGC AATACTATAT TAAAAAATGG CCCAAACCGG GCATTGCGAC GCAGAGCTTC
GGCATGACTA CCCTGACCGA TATGCTGGAT TTTATCGAGT TTACTCTTGC GACGCGCAAA CTTACCGGCA ACGCTGCTAT TAGAGAATTG
ACGGGCTATA TTACCGATGG CAAAAAGAT GATGTTGAGG TGCTGCGTCG CGTCATGATG CGTGATCTGG AGTGCGGTGC GTCAGTGAGC
ATCGCTAACA AAGTGTGGAA GGGTTTGATC CCGGAACAGC CACAGATGCT TGCAAGCAGC TACGATGAAA AGGGCATTAA CAAAAATATC
AAATTTCCGG CTTTCGCCCA GCTGAAAGCG GATGGCGCGC GCTGCTTCGC CGAGGTACGC GGTGACGAAC TGGACGACGT TCGTCTGCTG
TCTCGCAAAG GTAATGAATA TCTGGGTCTG GATCTGCTGA AGAAGAACT GATTAAGATG ACCGCCGAGG CGCGCCAAAT CCACCCCGAA
GGGGTGCTGA TTGATGGCGA ACTGGTGTAT CACGAACAGG TTGCAAAAGA GCCGGAGGGG TTGGATGCTC TGTTTGATCG ATACCCGGAA
AATAGCAAAG CGAAAGAATT TGCGGAAGTG GCGGAATCCC GCACCGCAAG CAATGGTATC GCAAATAAAT CGCTGAAGGG CACCATTTCT
GAGAAAGAAG CACAGTGTAT GAAGTTCCAG GTGTGGGACT ACGTGCCACT GGTTGAGATC TACTCCCTGC CAGCGTTTCG CCTGAAATAC
GATGTGCGTT TTTCAAAACT GGAACAGATG ACGAGCGGAT ATGATAAAGT AATTTTAATC GAGAACCAGG TCGTGAACAA CCTGGATGAA
GCAAAAGTTA TCTATAAAAA ATATATTGAT CAGGGCTTAG AAGGCATTAT CCTGAAGAAC ATTGATGGCC TTTGGGAAAA TGCACGCAGC
AAAAACCTGT ATAAATTTAA AGAAGTGATT TGGGTAGCTC TGAAGATTGT TGGTATTTAC CCGCATCGCA AAGACAAAAC CAAAGCAGGT
GGTTTCATCC TGGAATCTGA ATGCGGTAAA ATTAAAGTGA ACGCAGGCAG TGGTTTGAAA GATAAAGCAG GTGTTAAAAG TCACGAACTG
GATCGCACGC GCATCATGGA GAACCAGAAC TATTATATCG GCAAAATTCT GGAATGCAAA TGCAACGGGT GGCTTAAGAG CGATGGGCGC
AAACCCTATG TGAAATTGTT CCTGCCGATT GCGATTCGCC TTCGCGAAGA CAAAACTAAG GCGAATACTT TCGAAGATGT GTTCGGTGAT
TTTCATGAAG TCACGGGTCT GTAA
```

(SEQ ID NO: 52)

Met Ile Leu Lys Ile Leu Asn Glu Ile Ala Ser Ile Gly Ser Thr Lys Gln Lys Lys Ala Ile Leu Glu Lys

Asn Lys Asp Asn Glu Leu Leu Lys Arg Val Tyr Arg Leu Thr Tyr Ser Arg Gly Leu Gln Tyr Tyr Ile Lys

Lys Trp Pro Lys Pro Gly Ile Ala Thr Gln Ser Phe Gly Met Thr Thr Leu Thr Asp Met Leu Asp Phe Ile

Glu Phe Thr Leu Ala Thr Arg Lys Leu Thr Gly Asn Ala Ala Ile Arg Glu Leu Thr Gly Tyr Ile Thr Asp

Gly Lys Lys Asp Asp Val Glu Val Leu Arg Arg Val Met Met Arg Asp Leu Glu Cys Gly Ala Ser Val Ser

Ile Ala Asn Lys Val Trp Lys Gly Leu Ile Pro Glu Gln Pro Gln Met Leu Ala Ser Ser Tyr Asp Glu Lys

Gly Ile Asn Lys Asn Ile Lys Phe Pro Ala Phe Ala Gln Leu Lys Ala Asp Gly Ala Arg Cys Phe Ala Glu

Val Arg Gly Asp Glu Leu Asp Asp Val Arg Leu Leu Ser Arg Lys Gly Asn Glu Tyr Leu Gly Leu Asp Leu

Leu Lys Glu Glu Leu Ile Lys Met Thr Ala Glu Ala Arg Gln Ile His Pro Glu Gly Val Leu Ile Asp Gly

Glu Leu Val Tyr His Glu Gln Val Ala Lys Glu Pro Glu Gly Leu Asp Ala Leu Phe Asp Arg Tyr Pro Glu

Asn Ser Lys Ala Lys Glu Phe Ala Glu Val Ala Glu Ser Arg Thr Ala Ser Asn Gly Ile Ala Asn Lys Ser

Leu Lys Gly Thr Ile Ser Glu Lys Glu Ala Gln Cys Met Lys Phe Gln Val Trp Asp Tyr Val Pro Leu Val

Glu Ile Tyr Ser Leu Pro Ala Phe Arg Leu Lys Tyr Asp Val Arg Phe Ser Lys Leu Glu Gln Met Thr Ser

Gly Tyr Asp Lys Val Ile Leu Ile Glu Asn Gln Val Val Asn Asn Leu Asp Glu Ala Lys Val Ile Tyr Lys

Lys Tyr Ile Asp Gln Gly Leu Glu Gly Ile Ile Leu Lys Asn Ile Asp Gly Leu Trp Glu Asn Ala Arg Ser

Lys Asn Leu Tyr Lys Phe Lys Glu Val Ile Trp Val Ala Leu Lys Ile Val Gly Ile Tyr Pro His Arg Lys

Asp Lys Thr Lys Ala Gly Gly Phe Ile Leu Glu Ser Glu Cys Gly Lys Ile Lys Val Asn Ala Gly Ser Gly

Leu Lys Asp Lys Ala Gly Val Lys Ser His Glu Leu Asp Arg Thr Arg Ile Met Glu Asn Gln Asn Tyr Tyr

Ile Gly Lys Ile Leu Glu Cys Lys Cys Asn Gly Trp Leu Lys Ser Asp Gly Arg Lys Pro Tyr Val Lys Leu

Phe Leu Pro Ile Ala Ile Arg Leu Arg Glu Asp Lys Thr Lys Ala Asn Thr Phe Glu Asp Val Phe Gly Asp

Phe His Glu Val Thr Gly Leu (SEQ ID NO: 53)
```
ATGATTCTTA AAATTCTGAA CGAAATTGCA AGCATTAAGT CCACTAAACA AAAAAAGCC ATTCTGGAAA AAATAAAGA CAATGAACTG
TTAAAGCGCG TGTATCGCCT GACCTATTCG CGTGGCCTGC AATACTATAT TAAAAATGG CCCAAACCGG GCATTGCGAC GCAGAGCTTC
GGCATGACTA CCCTGACCGA TATGCTGGAT TTTATCGAGT TTACTCTTGC GACGCGCAAA CTTACCGGCA ACGCTGCTAT TAGAGAATTG
ACGGGCTATA TTACCGATGG CAAAAAGAT GATGTTGAGG TGCTGCGTCG CGTCATGATG CGTGATCTGG AGTGCGGTGC GTCAGTGAGC
ATCGCTAACA AAGTGTGGAA GGGTTTGATC CCGGAACAGC CACAGATGCT TGCAAGCAGC TACGATGAAA AGGGCATTAA CAAAAACATC
AAATTTCCGG CTTTCGCCCA GCTGAAAGCG GATGGCGCGC GCTGCTTCGC CGAGGTACGC GGTGACGAAC TGGACGACGT TCGTCTGCTG
TCTCGCAAAG GTAATGAATA TCTGGGTCTG GATCTGCTGA AGAAGAACT GATTAAGATG ACCGCCGAGG CGCGCCAAAT CCACCCCGAA
GGGGTGCTGA TTGATGGCGA ACTGGTGTAT CACGAACAGG TTGCAAAAGA GCCGGAGGGG TTAAAAGCTC TGTTTGATCG ATACCCGGAA
AATAGCAAAG CGAAAGAATT TGCGGAAGTG GCGGAATCCC GCACCGCAAG CAATGGTATC GCAAATAAAT CGCTGAAGGG CACCATTTCT
GAGAAAGAAG CACAGTGTAT GAAGTTCCAG GTGTGGGACT ACGTGCCACT GGTTGAGATC TACTCCCTGC CAGCGTTTCG CCTGAAATAC
GATGTGCGTT TTTCAAAACT GGAACAGATG ACGAGCGGAT ATGATAAAGT AATTTTAATC GAGAACCAGG TCGTGAACAA CCTGCTGGAA
GCAAAAGTTA TCTATAAAAA ATATATTGAT CAGGGCTTAG AAGGCATTAT CCTGAAGAAC ATTGATGGCC TTTGGGAAAA TGCACGCAGC
AAAAACCTGT ATAATTTAA AGAAGTGATT TGGGTAGATC TGAAGATTGT TGGTATTTAC CCGCATCGCA AAGACCCTAC CAAAGCAGGT
GGTTTCATCC TGGAATCTGA ATGCGGTAAA ATTAAAGTGA ACGCAGGCAG TGGTTTGAAA GATAAAGCAG GTGTTAAAAG TCACGAACTG
GATCGCACGC GCATCATGGA GAACCAGAAC TATTATATCG GCAAAATTCT GGAATGCAAA TGCAACGGGT GGCTTAAGAG CGATGGGCGC
AAGCCCGGTG TGAAATTGTT CCTGCCGATT GCGATTCGCC TTCGCGGAGA CAAAACTAAG GCGAATACTT TCGAAGATGT GTTCGGTGAT
TTTCATGAAG TCACGGGTCT GTAA
```

(SEQ ID NO: 54)
Met Ile Leu Lys Ile Leu Asn Glu Ile Ala Ser Ile Lys Ser Thr Lys Gln Lys Lys Ala Ile Leu Glu Lys

Asn Lys Asp Asn Glu Leu Leu Lys Arg Val Tyr Arg Leu Thr Tyr Ser Arg Gly Leu Gln Tyr Tyr Ile Lys

Lys Trp Pro Lys Pro Gly Ile Ala Thr Gln Ser Phe Gly Met Thr Thr Leu Thr Asp Met Leu Asp Phe Ile

Glu Phe Thr Leu Ala Thr Arg Lys Leu Thr Gly Asn Ala Ala Ile Arg Glu Leu Thr Gly Tyr Ile Thr Asp

Gly Lys Lys Asp Asp Val Glu Val Leu Arg Arg Val Met Met Arg Asp Leu Glu Cys Gly Ala Ser Val Ser

Ile Ala Asn Lys Val Trp Lys Gly Leu Ile Pro Glu Gln Pro Gln Met Leu Ala Ser Ser Tyr Asp Glu Lys

Gly Ile Asn Lys Asn Ile Lys Phe Pro Ala Phe Ala Gln Leu Lys Ala Asp Gly Ala Arg Cys Phe Ala Glu

Val Arg Gly Asp Glu Leu Asp Asp Val Arg Leu Leu Ser Arg Lys Gly Asn Glu Tyr Leu Gly Leu Asp Leu

Leu Lys Glu Glu Leu Ile Lys Met Thr Ala Glu Ala Arg Gln Ile His Pro Glu Gly Val Leu Ile Asp Gly

Glu Leu Val Tyr His Glu Gln Val Ala Lys Glu Pro Glu Gly Leu Lys Ala Leu Phe Asp Arg Tyr Pro Glu

Asn Ser Lys Ala Lys Glu Phe Ala Glu Val Ala Glu Ser Arg Thr Ala Ser Asn Gly Ile Ala Asn Lys Ser

Leu Lys Gly Thr Ile Ser Glu Lys Glu Ala Gln Cys Met Lys Phe Gln Val Trp Asp Tyr Val Pro Leu Val

Glu Ile Tyr Ser Leu Pro Ala Phe Arg Leu Lys Tyr Asp Val Arg Phe Ser Lys Leu Glu Gln Met Thr Ser

Gly Tyr Asp Lys Val Ile Leu Ile Glu Asn Gln Val Val Asn Asn Leu Leu Glu Ala Lys Val Ile Tyr Lys

Lys Tyr Ile Asp Gln Gly Leu Glu Gly Ile Ile Leu Lys Asn Ile Asp Gly Leu Trp Glu Asn Ala Arg Ser

Lys Asn Leu Tyr Lys Phe Lys Glu Val Ile Trp Val Asp Leu Lys Ile Val Gly Ile Tyr Pro His Arg Lys

Asp Pro Thr Lys Ala Gly Gly Phe Ile Leu Glu Ser Glu Cys Gly Lys Ile Lys Val Asn Ala Gly Ser Gly

Leu Lys Asp Lys Ala Gly Val Lys Ser His Glu Leu Asp Arg Thr Arg Ile Met Glu Asn Gln Asn Tyr Tyr

Ile Gly Lys Ile Leu Glu Cys Lys Cys Asn Gly Trp Leu Lys Ser Asp Gly Arg Lys Pro Gly Val Lys Leu

-continued

Phe Leu Pro Ile Ala Ile Arg Leu Arg Gly Asp Lys Thr Lys Ala Asn Thr Phe Glu Asp Val Phe Gly Asp

Phe His Glu Val Thr Gly Leu

Example 1

Ligase Gene Acquisition and Construction of Expression Vectors

The wild-type (WT) T4 DNA ligase enzyme (SEQ ID NO: 2) is encoded by the genome of the bacteriophage T4. A synthetic gene (SEQ ID NO: 3) encoding a 6-histidine tagged version of the WT T4 DNA ligase (SEQ ID NO: 4) was constructed and subcloned into the *Escherichia coli* expression vector pCK100900i (See e.g., U.S. Pat. No. 7,629,157 and US Pat. Appln. Publn. 2016/0244787, both of which are hereby incorporated by reference). A second synthetic gene (SEQ ID NO: 5) coding for a 6-histidine tagged T4 DNA ligase (SEQ ID NO: 6) was designed with codon optimization for *E. coli* expression, synthesized, and cloned into pCK100900i. These plasmid constructs were transformed into an *E. coli* strain derived from W3110. Directed evolution techniques generally known by those skilled in the art were used to generate libraries of gene variants from these plasmids (See e.g., U.S. Pat. No. 8,383,346 and WO 2010/144103, both of which are hereby incorporated by reference). The substitutions in the enzyme variants described herein are indicated with reference to the untagged WT T4 DNA ligase enzyme (i.e., SEQ ID NO: 2) or variants thereof, as indicated.

Example 2

T4 DNA Ligase Expression and Purification in High-Throughput (HTP)

High-Throughput (HTP) Growth of T4 DNA Ligase and Variants

Transformed *E. coli* cells were selected by plating onto LB agar plates containing 1% glucose and 30 µg/ml chloramphenicol. After overnight incubation at 37° C., colonies were placed into the wells of 96-well shallow flat bottom NUNC™ (Thermo-Scientific) plates filled with 180 µl/well LB medium supplemented with 1% glucose and 30 µg/ml chloramphenicol. The cultures were allowed to grow overnight for 18-20 hours in a shaker (200 rpm, 30° C., and 85% relative humidity; Kuhner). Overnight growth samples (20 µL) were transferred into Costar 96-well deep plates filled with 3804 of Terrific Broth supplemented with 30 µg/ml chloramphenicol. The plates were incubated for 120 minutes in a shaker (250 rpm, 30° C., and 85% relative humidity; Kuhner) until the $OD_{600}$ reached between 0.4-0.8. The cells were then induced with 40 µL of 10 mM IPTG in sterile water and incubated overnight for 18-20 hours in a shaker (250 rpm, 30° C., and 85% relative humidity; Kuhner). The cells were pelleted (4000 rpm×20 min), the supernatants were discarded, and the cells were frozen at −80° C. prior to analysis.

Lysis of HTP Pellets

Cell pellets were resuspended in 150 µl/well of 25 mM Tris-HCl, pH 7.5, and 300 µl of lysis buffer (B-Per reagent (Thermo Fisher) supplemented with 1 mg/ml lysozyme, and 0.1 mM magnesium sulfate) was added to the cell suspensions. The mixture was agitated for 1.25 hours at room temperature, pelleted (4000 rpm×20 min), and supernatants were reserved for purification.

HTP Purification of T4 Ligase from Crude Lysates

T4 DNA ligase was purified from crude *E. coli* extracts by metal-affinity chromatography using HIS-Select® High Capacity (HC) Nickel Coated Plates (Sigma) according to the manufacturer's instructions. HIS-Select plates were equilibrated with a total of 800 µl of wash buffer (50 mM sodium phosphate pH 7.5, 300 mM NaCl, 25 mM imidazole, 0.1% v/v TWEEN-20® reagent (Sigma)) per well. Then, 200 µl of HTP lysate containing T4 ligase and 200 µl of wash buffer were mixed, loaded onto the plate, and centrifuged for 1 min at 2000 relative centrifugal force (rcf) and 4° C. The plate was washed twice with 600 µl of wash buffer/well, with 3 min centrifugations at 3000 rcf and 4° C. for each wash. Ligase samples were eluted with the addition of 200 µl elution buffer (50 mM sodium phosphate pH 7.5, 300 mM NaCl, 250 mM imidazole, 0.1% v/v TWEEN®-20 reagent) by centrifugation for 1 min @ 3000 rcf at 4° C.

Eluates were buffer-exchanged using Zeba™ Spin desalting plates (Thermo Fisher). Briefly, plates were equilibrated twice with 375 µl of 2× T4 DNA ligase storage buffer (100 mM Tris.HCl pH 7.5, 200 mM NaCl, 2 mM DTT, 2 mM EDTA, 0.2% w/v Triton X-100) per well and centrifuged for 2 min @ 1100 xg at 4° C. Desalting plates were loaded with 1000 µl of the HIS-Select sample eluate and centrifuged for 2 min @ 1100×g at 4° C. The eluate from the desalting plate was retained and mixed with an equal volume of glycerol for a final storage buffer concentration of 50 mM Tris.HCl pH 7.5, 100 mM NaCl, 1 mM DTT, 1 mM EDTA, 0.1% w/v Triton X-100.

Example 3

Shake Flask Expression and Purification of T4 DNA Ligase

Shake Flask Expression

Selected HTP cultures grown as described above were plated onto LB agar plates with 1% glucose and 30 µg/ml chloramphenicol and grown overnight at 37° C. A single colony from each culture was transferred to 6 ml of LB broth with 1% glucose and 30 µg/ml chloramphenicol. The cultures were grown for 18 h at 30° C., 250 rpm, and subcultured at a dilution of approximately 1:10 into 250 ml of Terrific Broth with 30 µg/ml of chloramphenicol, to a final $OD_{600}$ of 0.2. The cultures were incubated for approximately 3 hours at 30° C., 250 rpm, to an $OD_{600}$ of 0.6-0.8, and then induced with the addition of IPTG at a final concentration of 1 mM. The induced cultures were incubated for 20 h at 30° C., 250 rpm. Following this incubation period, the cultures were centrifuged at 4000 rpm×10 min. The culture supernatant was discarded, and the pellets were resuspended in 35 ml of 25 mM triethanolamine, pH 7.5. This cell suspension was chilled in an ice bath and lysed using a Microfluidizer cell disruptor (Microfluidics M-110L). The crude lysate was pelleted by centrifugation (16,000 rpm for 60 min at 4° C.), and the supernatant was then filtered through a 0.2 µm PES membrane to further clarify the lysate.

Purification of T4 DNA Ligase from Shake Flask Lysates

T4 ligase lysates were supplemented with $\frac{1}{10}^{th}$ volume of SF elution buffer (50 mM sodium phosphate pH 7.5, 500 mM NaCl, 300 mM imidazole, 0.1% v/v Tween-20®) per well. Lysates were then purified using an AKTA Start purification system and a 5 ml HisTrap FF column (GE Healthcare) using the AC Step HiF setting (the run parameters are provided below). The SF wash buffer comprised 50 mM sodium phosphate pH 7.5, 500 mM NaCl, 25 mM imidazole, and 0.1% v/v TWEEN-20® (Sigma).

TABLE 3.1

Purification Parameters

| Parameter | Volume |
|---|---|
| Column volume | 5 ml |
| Flow rate | 5 ml/min |
| Pressure limit | 0.3 MPa |
| Sample volume | 35 mls |
| Equilibration volume | 5 column volumes (CV) = 25 mls |
| Wash Unbound volume | 15 CV = 75 mls |
| Elution | Isocratic (step) |
| Elution volume | 5 CV = 25 mls |
| Fraction volume | 3 mls |
| RE-equilibration volume | 5 CV = 25 mls |

The single most concentrated 3 ml fraction was identified by UV absorption (A280), and dialyzed overnight in 2× ligase storage buffer (20 mM Tris-HCl pH 7.5, 100 mM KCl, 2 mM DTT, 0.2 mM EDTA) overnight in a 10K Slide-A-Lyzer™ dialysis cassette (Thermo Fisher) for buffer exchange, and an equal volume of glycerol was added to the dialyzed material. Ligase concentrations in the preparations were measured by Bradford assay and absorption at 280 nm.

Example 4

Plate-Capture Ligation Assay

A high-throughput well-plate ligation assay was developed for use in screening libraries of T4 DNA ligase variants under low-concentration DNA inputs. The assay detects ligation of two labeled double-stranded DNA substrates. A Cy®3-labeled double-stranded 50 mer DNA fragment "50-mer Cy®3 insert" was comprised of two single-strand HPLC-purified synthetic oligonucleotides (Integrated DNA Technologies) (SEQ ID NO: 7, SEQ ID NO: 8), and was prepared by annealing these two oligonucleotides in 1× annealing buffer (10 mM Tris pH 7.5, 50 mM NaCl, 1 mM eEDTA). The resulting double-stranded "50-mer Cy®3 Insert" has single-base deoxyadenine 3' overhangs and 5' monophosphate ends on both ends of the molecule, and is internally labeled with Cy®3 dye attached to the phosphate backbone. A double-stranded "20-mer biotin adapter" molecule comprising two single-stranded HPLC-purified oligonucleotides (Integrated DNA Technologies) (SEQ ID NO: 9 and SEQ ID NO: 10) was also prepared by annealing in 1× annealing buffer. The resulting 20-mer biotin adapter duplex has a phosphorothioate-protected 5' deoxythymidine overhang and 5' phosphate at the ligation-compatible end, and was biotinylated at the opposite end. The ligation-compatible ends of these short model insert and adapter substrates were identical to the compatible T-A cohesive ends generated in NGS sample preparation workflows for the Illumina® TruSeq workflow. Ligation of these two substrates generated covalently linked ds DNA molecules labeled with both biotin and Cy®3 dye. Single- or double-ligated products may form upon ligation of the 20-mer biotin adapter to one or both ends of the 50-mer Cy®3 insert.

Ligation reactions were performed in an 80 ul volume in 1× ligation buffer (66 mM Tris, pH 7.5, 10 mM MgCl2, 1 mM DTT) and low concentrations of ligation substrate (1 nM 50-mer Cy®3 insert, and 5 nM or 10 nM 20-mer biotin adapter). HTP-purified ligase (5 µl) was added to the reactions, and reactions were incubated for 4 hours at 20° C. followed by 16 hours at 4° C. Reactions were quenched with the addition of 40 µl 3× quench solution (45 mM EDTA and 0.15% TWEEN®-20 reagent).

Streptavidin high-capacity binding plates (Pierce) were pre-washed 3 times with 200 µl of TBSTE buffer (25 mM Tris pH 7.5, 150 mM NaCl, 0.05% TWEEN-20 reagent, 1 mM EDTA). Then, 100 µl of the quenched ligation reactions were added to the pre-washed streptavidin plates, plates were shaken for 1 hr at room temperature to allow for binding, and unbound supernatants were discarded. Streptavidin plates were then washed 3 times with 200 ul TBSTE buffer, once with TBS buffer (25 mM Tris, 150 mM NaCl), and filled with 200 ul of TBS buffer. Washing efficiently removed the unligated 50-mer Cy®3 adapter, and retained the fluorescently labeled single- and double-ligation products on the streptavidin-coated well surface. Fluorescence intensities were measured using a Paradigm® multimode platereader (Beckman Coulter) using 535/35 nm excitation and 595/35 nm emission filters. Table 4.1 provides the activity improvement data for various ligase variants, relative to SEQ ID NO: 2., while Table 4.2 provides the activity for various ligase variants relative to SEQ ID NO: 6, and Table 4.3 provides the activity for various ligase variants relative to SEQ ID NO: 32.

TABLE 4.1

Activity Improvement of Ligase Variants Relative to SEQ ID NO: 2 (with 1 nM Insert and 10 nM Adapter)

| Variant # | Activity Improvement | Amino Acid Changes Relative to SEQ ID NO: 2 |
|---|---|---|
| 1 | ++ | C165A/S181T/K299P |
| 2 | ++ | C165A/S181T/V281A/K299A |
| 3 | ++ | S140A/S181T/L234M |
| 4 | ++ | P127K/I207R |
| 5 | + | P127K/L213M/C276G/I339V |
| 6 | + | P127K/L213M |
| 7 | ++ | K52E/A56R/N404K |
| 8 | ++ | Y238L/N241L/N404K/K412T/I462K |
| 9 | ++ | K52E/A56V/N404K/K412T |
| 10 | + | K52E/A56R/N404K |
| 11 | + | I462K |

Activity levels were determined relative to the reference polypeptide of SEQ ID NO: 2
Activity improvements are defined as follows:
++ = 1.3 to 1.6
+ = 1.2 to 1.3

TABLE 4.2

Ligase Variant Activity Improvements Relative to SEQ ID NO: 6

| Variant # | Activity Improvement | Amino Acid Changes Relative to SEQ ID NO: 6 |
|---|---|---|
| 12 | +++ | E88R/K225A/E440K/T451K |
| 13 | +++ | E88R/K306A/E440K/T451K |
| 14 | ++ | Q58K/E88R/K226E/K306A |
| 15 | ++ | L63R/E89K/T451K |
| 16 | ++ | T451K |
| 17 | ++ | Q58K/T451K |
| 18 | ++ | L63R/E89K/K226E/E440K/T451K |
| 19 | ++ | E89K |
| 20 | ++ | L63R/E88R/E89K |
| 21 | ++ | L63R/E88R/T451K |
| 22 | ++ | E88R/K470E |
| 23 | + | Q58K/E88R/E89K/K226E/E440K |
| 24 | + | Q58K/E88R/K199E/K225A/K226E |
| 25 | + | Q58K/E88R/K306A/K470E |

TABLE 4.2-continued

Ligase Variant Activity Improvements Relative to SEQ ID NO: 6

| Variant # | Activity Improvement | Amino Acid Changes Relative to SEQ ID NO: 6 |
|---|---|---|
| 26 | + | Q58K/E440K/K470E |
| 27 | + | Q58K/L63R/E89K |
| 28 | + | L63R/K199E/R297G/K375E |
| 29 | +++ | K52E/P127K/S181T/I462K |
| 30 | +++ | K52E/P127K/S140A/S181T/Y238L |
| 31 | +++ | P127K/S181T/Y238L/V372I |
| 32 | +++ | Y238L/N404K/I462K |
| 33 | +++ | K52E/P127K/S140A/S181T/I462K |
| 34 | +++ | P127K/S181T/I207R |
| 35 | +++ | P127K/Y238L/V372I/I462K |
| 36 | +++ | K52E/Y238L/N404K/I462K |
| 37 | +++ | P127K/L293E/N404K/I462K |
| 38 | +++ | S140A/Y238L/V372I/I462K |
| 39 | +++ | N404K |
| 40 | +++ | P127K/Y238L/L293E/I462K |
| 41 | +++ | S181T/Y238L/K299P/N404K |
| 42 | +++ | Y238L/K299P/N404K |
| 43 | +++ | K52E/S140A/S181T/Y238L/C276G/L293E/N404K |
| 44 | +++ | P127K/Y238L/L293E/K299P/N404K |
| 45 | +++ | P127K |
| 46 | +++ | V372I/I462K |
| 47 | +++ | K52E/P127K/N404K |
| 48 | +++ | K52E/N404K/I462K |
| 49 | +++ | I462K |
| 50 | +++ | S181T/Y238L/I462K |
| 51 | +++ | S181T/I462K |
| 52 | ++ | P127K/S181T/C276G |
| 53 | ++ | S181T/I207R/Y238L |
| 54 | ++ | S140A/C276G/L293E/N404K |
| 55 | ++ | V372I |
| 56 | ++ | P127K/Y238L/L293E/K299P/V372I/N404K |
| 57 | ++ | P127K/I462K |
| 58 | ++ | P127K/S140A/K299P/V372I/I462K |
| 59 | ++ | P127K/S140A/C276G |
| 60 | ++ | K52E/P127K/C276G/V372I/I462K |
| 61 | ++ | Y238L/L293E/V372I |
| 62 | ++ | C276G/L293E/I462K |
| 63 | ++ | S181T/I207R/Y238L/V372I |
| 64 | ++ | K52E/S181T |
| 65 | ++ | S140A/V285A/L293E/N404K |
| 66 | ++ | K52E/S140A/I207R/K299P/V372I/N404K/I462K |
| 67 | ++ | S140T |
| 68 | ++ | K52E/S140A/S181T/C276G/K299P/N404K/I462K |
| 69 | ++ | P127K/L293E |
| 70 | ++ | P127K/S140A/Y238L |
| 71 | ++ | K52E/S181T/Y238L/K299P/N404K |
| 72 | ++ | S181T/Y238L/C276G |
| 73 | ++ | K52E/L293E/K299P/N404K/I462K |
| 74 | ++ | L293E/V372I |
| 75 | + | S140A/K299P/V372I/N404K/I462K |
| 76 | + | P127K/L293E/V372I/I462K |
| 77 | + | P127K/S181T/N404K |
| 78 | + | S181T/C276G |
| 79 | + | K52E/S181T/Y238L/C276G |
| 80 | + | K52E/S181T/L293E |
| 81 | + | C276G/N404K |
| 82 | + | K52E/I207R/Y238L/L293E/K299P/N404K/I462K |
| 83 | + | Y238L/L293E/K299P/V372I/I462K |
| 84 | + | K299P/V372I/I462K |
| 85 | + | P127K/I207R/Y238L/V372I |
| 86 | + | K52E/C276G/K299P/N404K |
| 87 | + | S181T/I207R/Y238L/C276G/L293E/V372I/N404K |
| 88 | + | K299P/N404K/I462K |
| 89 | + | S181T/L293E |
| 90 | + | S140A/V372I |
| 91 | + | K52E/S140A/Y238L/C276G/K299P/V372I/N404K |

Activity levels were determined relative to the reference polypeptide of SEQ ID NO: 6
Activity improvements are defined as follows:
+++ = >2
++ = 1.5 to 2
+ = 1.25 to 1.5

TABLE 4.3

Ligase Variant Activity Improvements Relative to SEQ ID NO: 32

| Variant # | Activity Improvement | Amino Acid Changes Relative to SEQ ID NO: 32 |
|---|---|---|
| 92 | +++ | P127K/Y238L |
| 93 | +++ | P127K |
| 94 | +++ | P127K/D385E |
| 95 | +++ | E89K/P127K |
| 96 | +++ | Y238L/K306A/V372I |
| 97 | +++ | E89K/P127K/Y238L/K306A |
| 98 | +++ | N404K |
| 99 | ++ | V372I |
| 100 | ++ | P127K/K306A |
| 101 | ++ | P127K/V177A/Y238L/L293P/K306A |
| 102 | ++ | K306A |
| 103 | + | E89K |
| 104 | +++ | Q19K |
| 105 | ++ | Y238L |
| 106 | ++ | P127K/Q133H/Y238L/K375R |
| 107 | ++ | Q19K/Y238L |
| 108 | + | R297S |
| 109 | + | Q19K/P127K/K306A |
| 110 | + | Q19K/P127K/K199S |
| 111 | +++ | F247K/D373A/E427K/E438D |
| 112 | +++ | D176G/V250S/D373A/E438D/D480S |
| 113 | +++ | A244S/F247K |
| 114 | ++ | A244S/V250S/E438D |
| 115 | ++ | D176G/A244S/F247K/D373A/E438D |
| 116 | ++ | A244S/E438D |
| 117 | ++ | A244S/F247K/V250S |
| 118 | ++ | A244S |
| 119 | + | E438D |

Activity levels were determined relative to the reference polypeptide of SEQ ID NO: 32
Activity improvements are defined as follows:
+++ = >2
++ = 1.5 to 2
+ = 1.25 to 1.5

Example 5

Capillary Electrophoresis Ligation Assay

A capillary electrophoresis ligation assay was developed to allow for direct measurement of single and double-ligation products. This assay did not require fluorescently labeled substrates and provided flexibility for using commonly used adapters and relevant insert lengths.

Short, unlabeled adapter and insert fragments identical in sequence to those used in the plate capture assay were designed and synthesized. A Cy® 3-labeled double-stranded 50mer DNA fragment "50-mer insert" comprising two single-strand HPLC-purified synthetic oligonucleotides (Integrated DNA Technologies) (SEQ ID NO: 11 and SEQ ID NO: 12), and was prepared by annealing these two oligonucleotides in 1× annealing buffer (10 mM Tris pH 7.5, 50 mM NaCl, 1 mM EDTA). The resulting double-stranded 50-mer insert has single-base deoxyadenine 3' overhangs and 5' monophosphate ends on both ends of the molecule, and is internally labeled Cy®3 attached to the phosphate backbone. A double-stranded "20-mer adapter" molecule comprising two single-stranded HPLC-purified oligonucleotides (Integrated DNA technologies) (SEQ ID NO: 13 and SEQ ID NO: 14) was also prepared by annealing in 1× annealing buffer (10 mM Tris pH 7.5, 50 mM NaCl, 1 mM EDTA). The resulting 20-mer adapter duplex had a phosphorothioate-protected 5' deoxythymidine overhang and 5' phosphate at the ligation-compatible end.

A set of longer, defined 160-bp inserts were constructed by PCR amplification. Four sets of forward/reverse PCR primer pairs terminating with 5' adenosine (primers SEQ ID NO: 15 and SEQ ID NO: 16; product SEQ ID NO: 17), 5' cytosine (SEQ ID NO: 18 and SEQ ID NO: 19; product SEQ ID NO: 20), 5' guanosine (SEQ ID NO: 21 and SEQ ID NO: 22; product SEQ ID NO: 23), and 5' thymidine (SEQ ID NO: 24 and SEQ ID NO: 25; product SEQ ID NO: 26) nucleotides were used in separate reactions to amplify 160-bp fragments using the T4 DNA ligase phage-coding sequence (SEQ ID NO: 1) as template. These products have identical internal DNA sequences except for the bases at the 5' ends donated by the primer. Equimolar amounts of these inserts were then pooled and treated with the NEB Next Ultra™ II end-repair/dA-tailing module using the manufacturer's instructions to add 5' phosphates and 3' deoxyadenosine overhangs to prepare them for ligation.

Products were cleaned using the Wizard® SV PCR cleanup kit (Promega) and eluted in water.

Ligation reactions with the short 50/20mer substrates were performed in an 80 µl volume in 1× ligation buffer (66 mM Tris, pH 7.5, 10 mM MgCl, 1 mM DTT) and low concentrations of ligation substrate (2 nM 50-mer insert, 10 nM 20-mer adapter). For reactions with the longer 160-mer substrate set, 2 nM substrate and 20 nM of the NEB hairpin adapter (SEQ ID NO: 15) were used. HTP-purified ligase (10 ul) was added to the reaction, and reactions were incubated for 4 hours at 20° C. followed by 16 hours at 4° C.

Reactions were quenched with the addition of 40 µl 3× quench solution (45 mM EDTA, 0.6 mg/ml proteinase K). Quenched reactions were incubated at 50° C. for 1 hr to proteolyze the DNA ligase, which interferes with downstream electrophoresis by electrophoretic mobility shift. Then, 100 µl of the proteolyzed reaction was loaded onto a Montage SEQ$_{96}$ cleanup plate (EMD Millipore), and vacuum was applied to concentrate the sample. The sample was then washed with 100 µl of Low-TE buffer (2 mM Tris pH 7.5, 0.5 mM EDTA), and the filter surface was blotted. To elute the DNA substrates and ligation products, 25 µl of Low-TE buffer was added to the wells, the plate was shaken for 10 minutes at room temperature, and a Biomek NX liquid handler (Beckman Coulter) or 12-channel pipette was used to remove the eluate to a 384-well BioRad Hardshell® plate. Reaction mixtures were analyzed using a Caliper (now Perkin Elmer) Labchip GX capillary electrophoresis instrument using the DNA high sensitivity assay, according to the manufacturer's instructions.

Conversion was calculated by comparing the molar concentrations of the unligated insert, single ligated, and double-ligated products. For the short inserts, the fraction of double-ligated product was reported for the parental control and variants for use in calculating activity improvements. For the 160-mer insert set and NEB hairpin adapter, the fraction of total converted species (single and double-ligation products) was reported for use in calculating activity improvements.

TABLE 5.1

Ligase Variant Activity Improvements Relative to SEQ ID NO: 32

| Variant # | Activity Improvement | Amino Acid Changes Relative to SEQ ID NO: 32 |
|---|---|---|
| 120 | ++ | F233A |
| 121 | ++ | N149R |
| 122 | ++ | Y453R |
| 123 | ++ | D371W |
| 124 | ++ | L63T |
| 125 | ++ | Y453G |
| 126 | + | E240P |
| 127 | + | Y453G |
| 128 | + | V454L |
| 129 | + | A237N |
| 130 | + | E240P |
| 131 | + | F60G |
| 132 | + | D371W |
| 133 | + | D385A |
| 134 | + | F60V |
| 135 | + | A237R |
| 136 | + | Y238L |
| 137 | + | Y453T |
| 138 | + | G184A |
| 139 | + | A56S |
| 140 | + | A461C |
| 141 | + | P51R |
| 142 | + | D371V |
| 143 | + | Y453L |
| 144 | + | F233T |
| 145 | + | D385W |
| 146 | + | K446R |
| 147 | +++ | D452P |
| 148 | +++ | D448A |
| 149 | +++ | D448P |
| 150 | +++ | D452V |
| 151 | ++ | A86R |
| 152 | ++ | Y314V |
| 153 | ++ | K199T |
| 154 | ++ | E438F |
| 155 | ++ | D329G |
| 156 | ++ | T485G |
| 157 | ++ | D329G |
| 158 | ++ | K451G |
| 159 | ++ | D373A |
| 160 | ++ | E466G |
| 161 | ++ | E427R |
| 162 | ++ | D329L |
| 163 | ++ | I207V |
| 164 | ++ | C439S |
| 165 | ++ | D373G |
| 166 | ++ | D476A |
| 167 | ++ | E466P |
| 168 | + | E427L |
| 169 | + | E438G |
| 170 | + | L174P |
| 171 | + | I207Q |
| 172 | + | T485Y |
| 173 | + | E438D |

Activity levels were determined relative to the reference polypeptide of SEQ ID NO: 32
Activity improvements are defined as follows:
+++ = >1.5
++ = 1.3 to 1.5
+ = 1.2 to 1.3

TABLE 5.2

Ligase Variant Activity Improvements Relative to SEQ ID NO: 32

| Variant # | Activity Improvement | Amino Acid Changes Relative to SEQ ID NO: 32 |
|---|---|---|
| 175 | + | E321A |
| 176 | + | E321R |
| 177 | + | Q280L |
| 178 | +++ | N7L |
| 179 | +++ | K52G |
| 180 | +++ | N404S |
| 181 | +++ | F235R |
| 182 | +++ | A237G |
| 183 | +++ | I462Q |
| 184 | +++ | E240P |
| 185 | +++ | A405G |
| 186 | +++ | G54E |
| 187 | +++ | Y453L |
| 188 | +++ | S242H |
| 189 | +++ | D371G |
| 190 | ++ | V454A |
| 191 | ++ | S59M |
| 192 | ++ | Q17R |
| 193 | ++ | N241G |
| 194 | ++ | D371G |
| 195 | ++ | A183N |
| 196 | ++ | D452P |
| 197 | ++ | E483G |
| 198 | ++ | F74T |
| 199 | ++ | E483Q |
| 200 | ++ | K451G |
| 201 | ++ | A85T |
| 202 | + | F74G |

Activity levels were determined relative to the reference polypeptide of SEQ ID NO: 32
Activity improvements are defined as follows:
+++ = >2
++ = 1.5 to 2
+ = 1.2 to 1.5

TABLE 5.3

Ligase Variant Activity Improvements Relative to SEQ ID NO: 6

| Variant # | Activity Improvement | Amino Acid Changes Relative to SEQ ID NO: 6 |
|---|---|---|
| 204 | +++ | N149K |
| 205 | +++ | D385K |
| 206 | +++ | A413K |
| 207 | ++ | L231K |
| 208 | ++ | A183K |
| 209 | ++ | G184K |
| 210 | ++ | D232K |
| 211 | ++ | P386K |
| 212 | ++ | G13K |
| 213 | ++ | E186K |
| 214 | ++ | E240K |
| 215 | ++ | E89K |
| 216 | ++ | S11K |
| 217 | + | Y238K |
| 218 | + | F233K |
| 219 | + | S14K |
| 220 | + | Y453K |
| 221 | + | N185K |
| 222 | + | P239K |
| 223 | + | G54K |
| 224 | + | N7K |
| 225 | + | M62K |

Activity levels were determined relative to the reference polypeptide of SEQ ID NO: 6
Activity improvements are defined as follows:
+++ = >2
++ = 1.5 to 2
+ = 1.25 to 1.5

TABLE 5.4

Ligase Variant Activity Improvements Relative to SEQ ID NO: 34

| Variant # | Activity improvement | Amino Acid Changes Relative to SEQ ID NO: 34 |
|---|---|---|
| 226 | +++ | L63T/N149R/E240P/D371W/D452P |
| 227 | +++ | Q19K/L63T/F233A/A237R/D371W/D452P |
| 228 | +++ | E89K/F233A/A237R/E240P/D448A/Y453G/V454L |
| 229 | ++ | N149R/F233A/A237N/V454L |
| 230 | ++ | A86R/E89K/N149R/F233A/A237N/E240P |
| 231 | ++ | E89K/E240P/V454L |
| 232 | ++ | Q19K/A237N/Y453G |
| 233 | ++ | N149R/A237N/E240P |
| 234 | + | A86R/E89K/F233A/A237N/E240P/D448A |
| 235 | + | N149R/A237N/E240P/D329G/N404K/Y453G |
| 236 | + | F233A/A237N/D371W/N404K/D452P/V454L |
| 237 | + | F233A/A237R/N404K |
| 238 | + | L63T/E89K/D448A/D452P/Y453G |
| 239 | + | A86R/E89K/N149R/F233A/A237R/Y314V/D452P |
| 240 | + | L63T/F233A/E240P/D452P/V454L |

Activity levels were determined relative to the reference polypeptide of SEQ ID NO: 34.
Activity improvements are defined as follows:
+++ = >1.5
++ = 1.3 to 1.5
+ = 1.2 to 1.3

TABLE 5.5

Ligase Variant Activity Improvements Relative to SEQ ID NO: 38

| Variant # | Activity improvement | Amino Acid Changes Relative to SEQ ID NO: 38 |
|---|---|---|
| 241 | +++ | G13K/A183K/D232K/D329L/Y453G/E466G |
| 242 | +++ | G13K/A183K/D232K/P386K/K451G |
| 243 | +++ | G13K/E89K/A183K/D232K/P386K/K451G |
| 244 | +++ | D385K/Y453R/E466G |
| 245 | +++ | A183K/D373A/P386K |
| 246 | ++ | A183K/L231K/E427R/E466G |
| 247 | ++ | A183K/I207V/P386K/E427R/Y453G |
| 248 | ++ | G13K/E89K/A183K/L231K |
| 249 | ++ | G13K/D232K/D385K/K451G |
| 250 | ++ | N149R/A183K |
| 251 | ++ | A183K |
| 252 | ++ | A183K/A413K/E427R |
| 253 | ++ | E89K/A183K/D329G/K451G/Y453R |
| 254 | ++ | N149R/A183K |
| 255 | ++ | A183K/D385K |
| 256 | ++ | A183K/D385K/E427R |
| 257 | ++ | A183K/L231K/D385K/E427R |
| 258 | ++ | A183K/E427R/K451G |
| 259 | ++ | A183K/I207V/P386K |
| 260 | ++ | A183K/I207V/C439S |
| 261 | ++ | A183K/L231K/D373G |

Activity levels were determined relative to the reference polypeptide of SEQ ID NO: 38, and are defined as:
+++ = >1.5
++ = 1.3 to 1.5

Example 6

Capillary Electrophoresis Ligation Assay on Shake-Flask Scale Preparations

Ligase variants were expressed and purified at the shake-flask scale as described in Example 3. A capillary electrophoresis ligation assay was performed in 1× ligation buffer (66 mM Tris, pH 7.5, 10 mM MgCl2, 1 mM DTT) as described in Example 5, using 875 nM of the SF-purified DNA ligase, 1 nM of the 160-mer A-tailed insert (See, Example 5), and 200 nM of a commercially available Y adapter (Illumina). This Y adapter is comprised of two HPLC-purified oligonucleotides (SEQ ID NO: 17 and SEQ ID NO: 18), annealed as described in Example 4. Reactions were quenched with the addition of EDTA to 15 mM and proteinase K to 0.4 mg/ml (final), and incubated at 50C for 1 hour to proteolyze the DNA ligase, which interferes with downstream electrophoresis. Proteolyzed ligation reactions were then cleaned and buffer-exchanged using a 96-well Zymo DNA Clean & Concentrator kit and eluted in 25 ul of low-TE buffer (2 mM Tris, 0.5 mM EDTA). Reaction mixtures were analyzed using a Perkin Elmer Labchip GX capillary electrophoresis instrument using the DNA High Sensitivity assay (Perkin Elmer), according the manufacturer's instructions.

Conversion of insert to double-ligated products was calculated by comparing the molar concentrations of the unligated insert, single-ligated, and double-ligated products. The fraction of insert converted to double-ligated product was reported for the variants, as indicated in Table 6.1, below.

TABLE 6.1

Ligation Assay Results (Amino Acid Changes Relative to SEQ ID NO: 6)

| SEQ ID NO: | Substitutions | Double-end Ligation (% Conversion) |
|---|---|---|
| SEQ ID NO: 2 | (Wild -type) | + |
| SEQ ID NO: 32 | E88R/K225A/E440K/T451K | +++ |
| SEQ ID NO: 34 | E88R/P127K/K225A/E440K/T451K | +++ |
| SEQ ID NO: 36 | L63T/E88R/P127K/N149R/K225A/E240P/D371W/E440K/T451K/D452P | +++ |
| SEQ ID NO: 38 | Q19K/L63T/E88R/P127K/K225A/F233A/A237R/D371W/E440K/T451K/D452P | +++ |
| SEQ ID NO: 40 | E88R/E89K/P127K/K225A/F233A/A237R/E240P/E440K/D448A/T451K/Y453G/V454L | +++ |
| SEQ ID NO: 42 | E88R/P127K/N149R/K225A/F233A/A237N/E440K/T451K/V454L/ | +++ |
| SEQ ID NO: 44 | A86R/E88R/E89K/P127K/N149R/K225A/F233A/A237N/E240P/E440K/T451K | ++ |
| SEQ ID NO: 46 | Q19K/L63T/E88R/P127K/A183K/K225A/L231K/F233A/A237R/D371W/E427R/E440K/T451K/D452P/E466G | ++ |
| SEQ ID NO: 48 | Q19K/L63T/E88R/P127K/K225A/F233A/A237R/D371W/D385K/E440K/T451K/D452P/Y453R/E466G | +++ |
| SEQ ID NO: 50 | G13K/Q19K/L63T/E88R/P127K/A183K/K225A/D232K/F233A/A237R/D371W/P386K/E440K/T451G/D452P | ++ |
| SEQ ID NO: 52 | Q19K/L63T/E88R/P127K/A183K/K225A/F233A/A237R/D371W/D373A/P386K/E440K/T451K/D452P | ++ |
| SEQ ID NO: 54 | G13K/Q19K/L63T/E88R/P127K/A183K/K225A/D232K/F233A/A237R/D329L/D371W/E440K/T451K/D452P/Y453G/E466G | ++ |

The conversion values indicated above correspond to:
+++ = >80% double-ligated product
++ = >65% double-ligated product
+ = ~50% double-ligated product Example 7

Adapter Dimerization Assay on Shake-Flask Scale Preparations

NGS adapters designed for use on the Illumina® sequencing platform have deoxythymidine 3' overhangs compatible for ligation with deoxyadenosine 3' overhangs present on A-tailed insert fragments. T-tailed adapters are not efficiently ligated to one another due to the selectivity of wild-type T4 DNA ligase against non-complementary DNA ends. Adapter dimerization will occur as a result of extreme ligation conditions including long incubation periods, high adapter concentrations, or high concentrations of crowding agent. Importantly, nuclease contaminants in the ligation reaction can remove overhangs on the adaptor ends, resulting in blunt-ended substrates, which are compatible for self-ligation.

To test the selectivity of an exemplary variant T4 DNA ligase, a purification strategy was developed to reduce nuclease contamination which would confound the direct observation of any inherent adapter dimerization activity.

Gradient Purification of T4 DNA Ligase from Shake Flask Lysates

Ligases were expressed in shake flasks according to the method in Example 3, and resuspended in 50 mM Tris HCl pH 7.5 prior to lysis. This cell suspension was chilled in an ice bath and lysed using a Microfluidizer cell disruptor (Microfluidics M-110L). Crude lysates were supplemented with 500 mM NaCl and 30 mM imidazole before clarification by centrifugation (16,000 rpm for 60 min at 4° C.), and supernatants were then filtered through a 0.2 μm PES membrane to further clarify the lysates.

Lysates were purified using an AKTA Start system and a 1ml HisTrap FF column (GE Healthcare) using an nickel NTA protocol and an imidazole gradient elution (run parameters are provided in Table 7.1). The SF wash buffer was comprised of 50 mM Tris HCl pH 7.5, 500 mM NaCl, 30 mM imidazole, and 1 mM DTT. The SF elution buffer was comprised of 50 mM Tris HCl pH 7.5, 500 mM NaCl, 300 mM imidazole, and 1 mM DTT.

TABLE 7.1

Purification Parameters

| Parameter | Volume |
|---|---|
| Column volume | 1 ml |
| Flow rate | 1 ml/min |
| Pressure limit | 0.4 MPa |
| Sample volume | ~35 mls |
| Equilibration volume | 5 column volumes (CV) = 25 mls |
| Wash Unbound volume | 30 CV = 30 mls |
| Elution | Gradient 0-50% Elution buffer |
| Elution volume | 20 CV = 20 mls |
| Fraction volume | 1 mls |
| RE-equilibration volume | 5 CV = 25 mls |

The four most concentrated fractions were identified by UV absorption (A280), and dialyzed overnight in 1× ligase storage buffer (10 mM Tris HCl pH 7.5, 50 mM KCl, 1 mM DTT, 0.1 mM EDTA) overnight in a 10K Slide-A-Lyzer™ dialysis cassette (Thermo Fisher) for buffer exchange. Ligase concentrations in the preparations were measured by Bradford assay and absorption at 280 nm.

A larger-scale purification from a fermentation pellet was carried out using the same chromatography parameters for experiments in Examples 10-14. In this case, the most concentrated fractions from the Nickel sepharose eluate were pooled and passed in flow-through mode over two successive STIC-PA nano (1ml) charge membrane filters (Sartorius) to remove contaminating nucleic acids.

An adapter dimerization assay was performed in 1× ligation buffer (66 mM Tris, pH 7.5, 10 mM MgCl$_2$, 1 mM DTT) as described in Example 5, using 875 nM of the SF-purified DNA ligase, and 1000 nM of a blocked adapter comprised of two oligonucleotides (SEQ ID NO: 13 and SEQ ID NO: 16, annealed as described in Example 4). This blocked 20-mer adapter duplex has one ligation-competent end with a 3' deoxythymidine overhang and 5' phosphate and a second blunt, ligation-incompetent end with no 5' phosphate and an amino-blocked 3' end, which cannot serve as a substrate for ligation. Ligations were performed at 20° C. for 16 hours to allow for dimer formation. Reactions were quenched with the addition of EDTA to 15 mM and proteinase K to 0.2 mg/ml (final), and incubated at 50° C. for 2 hours to proteolyze the DNA ligase. Reaction mixtures were directly analyzed using a Perkin Elmer Labchip GX capillary electrophoresis instrument using the DNA 1k Assay (Perkin Elmer), according the manufacturer's instructions.

Adapter dimerization percent conversion was calculated by comparing the molar concentrations of the unligated adapter and adapter dimer products measured via capillary electrophoresis. The fraction of blocked 20mer adapter converted to double-ligated product is indicated in Table 7.2. A sample of WT T4 DNA ligase prepared according to the protocol from Example 3, and known to contain nuclease contamination was included as a positive control for adapter dimer formation, and an "Ultra-pure" commercial prep of T4 DNA ligase (Enzymatics) was used as a reference for WT ligase dimerization activity.

TABLE 7.2

Ligase Adapter Dimerization Conversion Percentages

| Ligase sample | Preparation Method | Adapter Dimerization (% Conversion) |
|---|---|---|
| WT T4 DNA ligase | Commercial "Ultra Pure" preparation | + |
| WT T4 DNA ligase | Example 3 Method | ++ |
| SEQ ID NO: 38 | Example 3 Method | +++ |
| SEQ ID NO: 38 | Example 7 Method | + |

The conversion values indicated above correspond to:
+++ = >10% conversion
++ = 2-10% conversion
+ = <2% conversion Example 8

DNA Ligation Timecourse

A ligation reaction timecourse was perfomed in 1× ligation buffer supplemented with crowding agent (66 mM Tris, pH 7.5, 10 mM MgCl$_2$, 1 mM DTT, 6% PEG$_{6000}$ (w/v)) as described in Example 5, using either 855 nM final concentration of a variant ligase (SEQ ID NO: 38) purified according to the method described in Example 7, or a commercial preparation of wild-type T4 DNA ligase ("Ultra-Pure" T4 DNA ligase (Rapid), Enzymatics). The DNA substrates included 1 nM of the A-tailed 160-mer PCR product described in Example 6 and 40 nM of an adapter comprised of two oligonucleotides (SEQ ID NO: 17 and SEQ ID NO: 18, annealed as described in Example 4). Reactions were initiated with the addition of ligase and were quenched after 2, 5, 15, and 30 minutes with the addition of EDTA to a final concentration of 15 mM. Proteinase K was added to a final concentration of 0.2 mg/ml, and samples were proteolyzed for 2 hrs at 50° C., followed by sample cleanup using the Zymo ZR-96 DNA Clean & Concentrator-5 wellplate cleanup kit (Zymo Research). Samples were eluted in 25 ul of EB buffer, and analyzed by capillary electrophoresis according to the method described in Example 6. Conversion to double-end ligated products is reported for each timepoint in Table 8.1.

TABLE 8.1

Ligation Time Course Data

| SEQ ID NO | Description | Double-end Ligation Conversion (%) | | | |
|---|---|---|---|---|---|
| | | 2 min | 5 min | 15 min | 30 min |
| SEQ ID NO: 2 | WT T4 DNA ligase commercial preparation | + | + | ++ | ++ |
| SEQ ID NO: 38 | T4 ligase variant | ++++ | +++++ | +++++ | +++++ |

+++++ 90.1-95% double-ligated product
++++ 85.1-90%
+++ 50.1-85%
++ 30.1-50%
+ 0-30%

Example 9

Temperature Activity Profile

A ligation reaction timecourse was perfomed in 1× ligation buffer (66 mM Tris, pH 7.5, 10 mM MgCl$_2$, 1 mM DTT) as described in Example 5, using either 855 nM final concentration of a variant ligase (SEQ ID NO: 38) purified according to the method described in Example 7, or a commercial preparation of wild-type T4 DNA ligase ("Ultra-Pure" T4 DNA ligase (Rapid); Enzymatics).

The DNA substrates included 1 nM of the A-tailed 160-mer PCR product described in Example 6 and 200 nM of an adapter comprised of two oligonucleotides (SEQ ID NO: 13 and SEQ ID NO: 16, annealed as described in Example 4). Reactions were initiated with the addition of ligase and incubated at 16° C., 20° C., 30° C. or 37° C. for 30 minutes, then quenched with the addition of EDTA to a final concentration of 15 mM. Proteinase K was added to a final concentration of 0.2 mg/ml, and samples were proteolyzed for 1 hour at 50° C., followed by sample cleanup using the Zymo ZR-96 DNA Clean & Concentrator-5 wellplate cleanup kit (Zymo Research). Samples were eluted in 25 ul of EB buffer and analyzed by capillary electrophoresis according to the method described in Example 6. Conversion to double-end ligated products is graphed for each temperature condition in FIG. 1.

Example 10 pH Activity Profile

Figure 2:
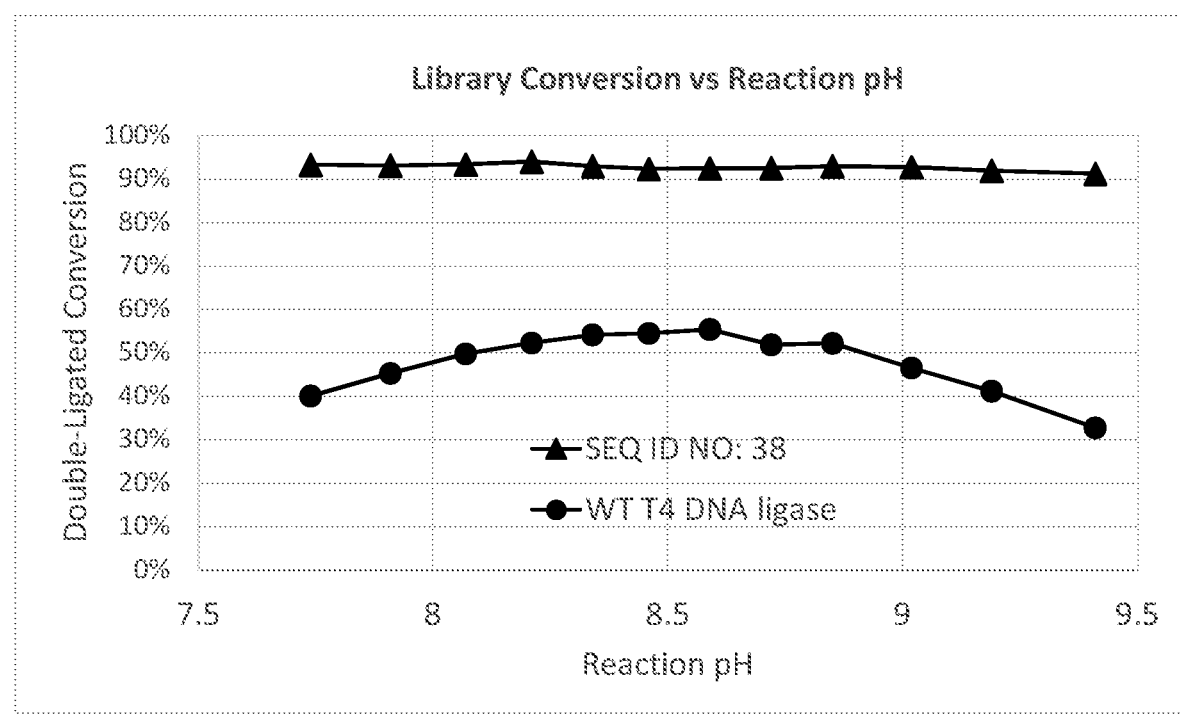
FIG. 2 provides a graph showing the conversion to double-end ligated products at various pHs by the polypeptide of SEQ ID NO: 38 and wild-type T4 DNA ligase, as described in Example 10.

Ligation reactions were perfomed in 1× ligation buffer supplemented with crowding agent (66 mM Tris, pH 7.5, 10 mM MgCl$_2$, 1 mM DTT, 6% PEG$_{6000}$ (w/v)) as described in Example 5, using either 855 nM final concentration of a variant ligase c) purified according to the method described in Example 7, or a commercial preparation of wild-type T4 DNA ligase ("Ultra-Pure" T4 DNA ligase (Rapid); Enzymatics). The DNA substrates included 1 nM of the A-tailed 160-mer PCR product described in Example 6, and 40 nM of an adapter comprised of two oligonucleotides (SEQ ID NO: 17 and SEQ ID NO: 18, annealed as described in Example 4). Reactions were initiated with the addition of ligase, and were quenched after 15 minutes by the addition of HiPrep™ PCR SPRI beads (MagBio Genomics, 80 µl into a 1000 µl reaction). Samples were eluted in 25 ul of EB buffer, and analyzed by capillary electrophoresis according to the method described in Example 6. Conversion to double-end ligated products is plotted in FIG. 2.

Example 11

Ligation Sequence Bias

A ligation reaction timecourse was perfomed in 1× ligation buffer supplemented with crowding agent (66 mM Tris, pH 7.5, 10 mM MgCl$_2$, 1 mM DTT, 6% PEG$_{6000}$ (w/v)) as described in Example 5, using either 855 nM final concentration of a variant ligase (SEQ ID NO: 38) purified according to the method described in Example 7, or a commercial preparation of wild-type T4 DNA ligase ("Ultra-Pure" T4 DNA ligase (Rapid); Enzymatics). The DNA substrates included 50 ng of the A-tailed 160-mer PCR product described in Example 6, except the individual PCR products were not pooled, but separately ligated.

Figure 3:
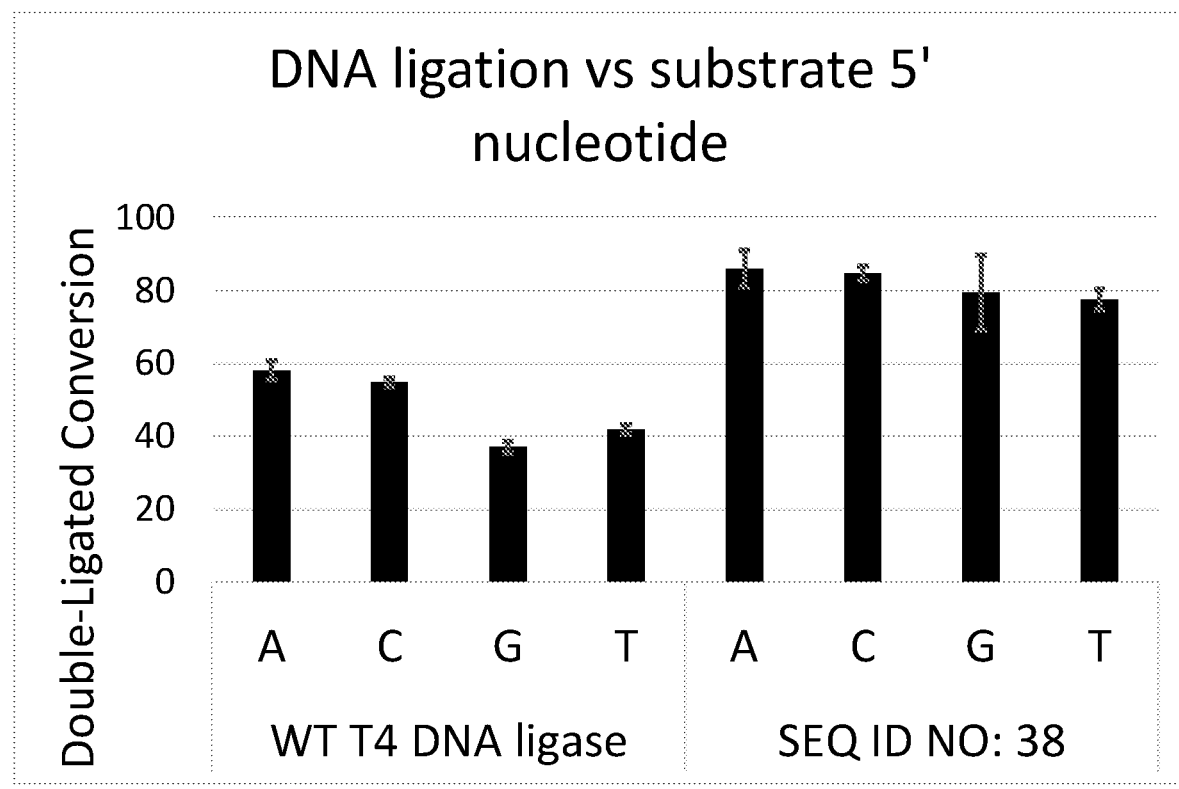
FIG. 3 provides a graph showing the conversion to double-end ligation products by the polypeptide of SEQ ID NO: 38 and wild-type T4 DNA ligase, as described in Example 11.

A set of defined 160-bp inserts varying by sequence at their 5; ends were constructed by PCR amplification. Four sets of forward/reverse PCR primer pairs terminating with 5' adenosine (primers SEQ ID NO: 15 and SEQ ID NO: 16; product SEQ ID NO: 17), 5' cytosine (SEQ ID NO: 18 and SEQ ID NO: 19; product SEQ ID NO: 20), 5' guanosine (SEQ ID NO: 21 and SEQ ID NO: 22; product SEQ ID NO: 23), and 5' thymidine (SEQ ID NO: 24 and SEQ ID NO: 25; product SEQ ID NO: 26) nucleotides were used in separate reactions to amplify 160-bp fragments using the T4 DNA ligase phage-coding sequence (SEQ ID NO: 1) as template. These products have identical internal DNA sequences except for the bases at the 5' ends that are donated by the primer. These inserts were then individually treated with the NEB Next Ultra™ II end-repair/dA-tailing module using the manufacturer's instructions to add 5' phosphates and 3' deoxyadenosine overhangs to prepare them for ligation. Prepared substrates were individually cleaned up according to the manufacturer's instructions using DNA Clean and Concentrator-5 spin columns (Zymo Research). Ligations were performed using 40 nM of an adapter comprised of two oligonucleotides (SEQ ID NO: 17 and SEQ ID NO: 18, annealed as described in Example 4). Reactions were initiated with the addition of ligase, and were quenched after 15 minutes by the addition of HiPrep™ PCR SPRI beads (MagBio Genomics; 80 µl into a 1000 1 reaction) and prepared according to the manufacturer's instructions. Samples were eluted in 25 ul of nuclease-free TE buffer (10 mM Tris, 1 mM EDTA), and analyzed by capillary electrophoresis using the method described in Example 6. Conversion to double-end ligated products is plotted in FIG. 3.

Example 12

Conversion as a Function of Ligase Concentration

Figure 4:
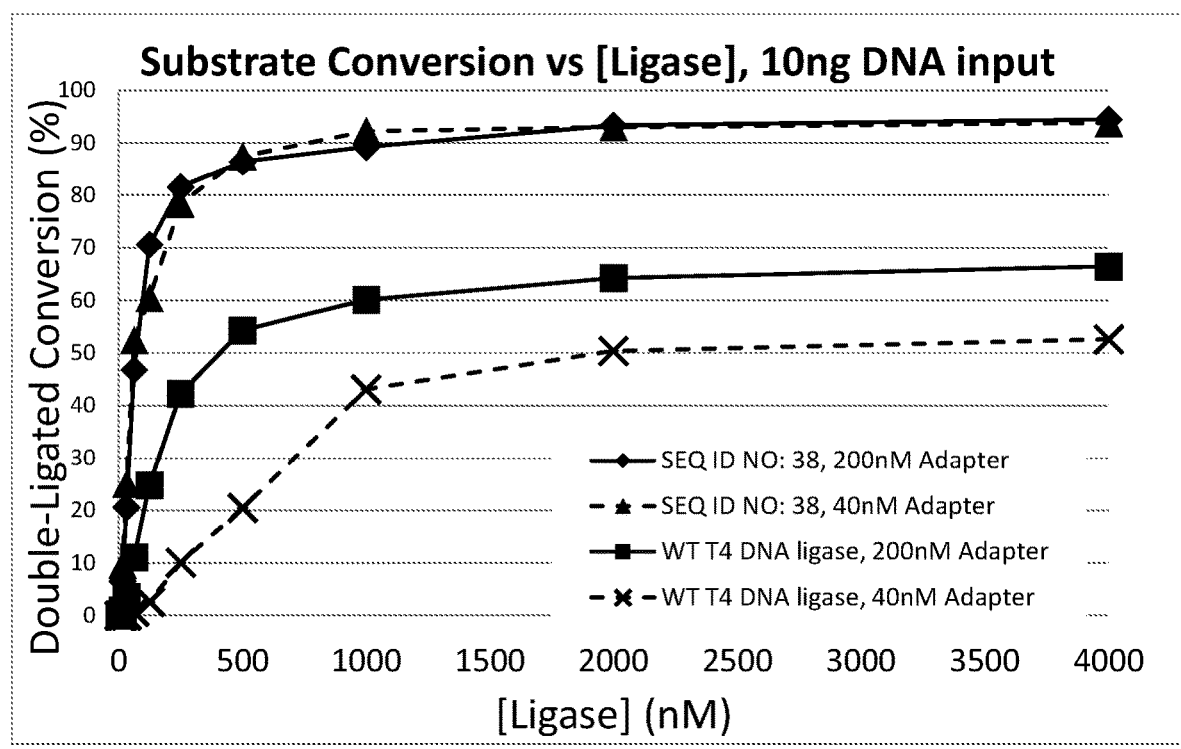
FIG. 4 provides a graph showing the substrate conversion to double-end ligation in the presence of 200 nM adapter or 40 nM adapter by the polypeptide of SEQ ID NO: 38 and wild-type T4 DNA ligase, as described in Example 12.

Ligation reactions were perfomed in 1× ligation buffer supplemented with crowding agent (66 mM Tris, pH 7.5, 10 mM MgCl$_2$, 1 mM DTT, 6% PEG$_{6000}$ (w/v)) as described in Example 5, using a range of 2 to 4000 nM final concentrations of a variant ligase (SEQ ID NO: 38) purified according to the method described in Example 7, or a commercial preparation of wild-type T4 DNA ligase ("Ultra-Pure" T4 DNA ligase (Rapid); Enzymatics). The DNA substrates included 10 ng of the A-tailed 160-mer PCR product described in Example 6 and 40 nM or 200 nM of an adapter comprised of two oligonucleotides (SEQ ID NO: 17 and SEQ ID NO: 18, annealed as described in Example 4). Reactions were initiated with the addition of ligase, and were quenched after 15 minutes by the addition of HiPrep™ PCR SPRI beads (MagBio Genomics; 80 µl into a 100 1 reaction). Samples were eluted in 25 ul of EB buffer, and analyzed by capillary electrophoresis using the method described in Example 6. Conversion to double-end ligated products is plotted in FIG. 4.

Example 13

Conversion as a Function of Adapter Concentration

Figure 5:
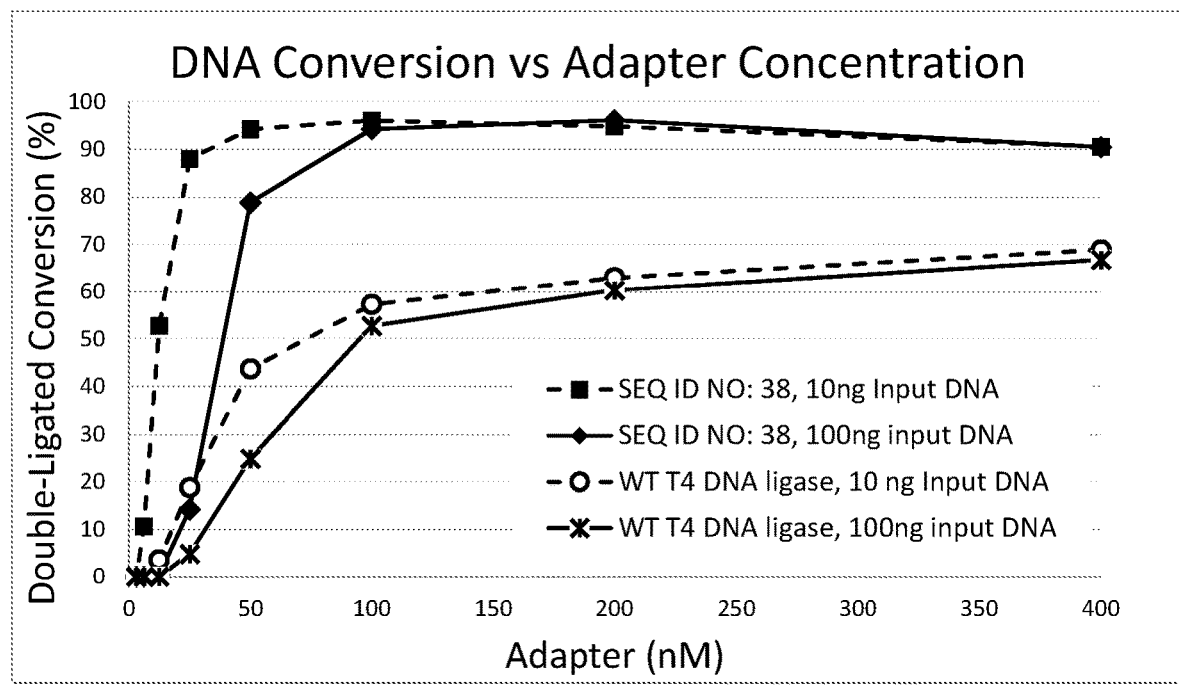
FIG. 5 provides a graph showing the percent conversion to double-end ligation products at 10 ng and 100 ng input DNA by the polypeptide of SEQ ID NO: 38 and wild-type T4 DNA ligase, as described in Example 13.

Ligation reactions were perfomed in 1× ligation buffer supplemented with crowding agent (66 mM Tris, pH 7.5, 10 mM MgCl$_2$, 1 mM DTT, 6% PEG$_{6000}$ (w/v)) as described in Example 5, using a final concentration of 855 nM of a variant ligase (SEQ ID NO: 38) purified according to the method described in Example 7, or a commercial preparation of wild-type T4 DNA ligase ("Ultra-Pure" T4 DNA ligase (Rapid); Enzymatics). The DNA substrates included 10 ng or 100 ng of the A-tailed 160-mer PCR product described in Example 6, and a 3 to 400 nM titration of of an adapter comprised of two oligonucleotides (SEQ ID NO: 17 and SEQ ID NO: 18, annealed as described in Example 4). Reactions were initiated with the addition of ligase, and were quenched after 15 minutes by the addition of HiPrep™ PCR SPRI beads (MagBio Genomics; 80 µl into a 1000 reaction), then cleaned up according to the manufacturer's protocol. Samples were eluted in 25 ul of EB buffer, and analyzed by capillary electrophoresis using the method described in Example 6. Percent conversion to double-end ligated products is plotted in FIG. 5.

Example 14

Conversion of Cell-Free DNA Substrates

Figure 6:
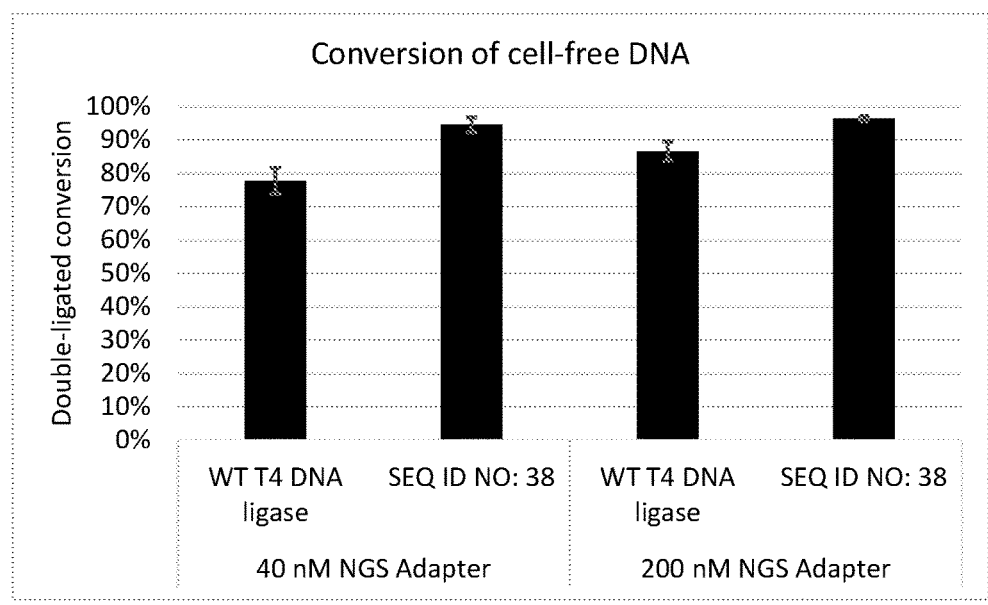
FIG. 6 provides a graph showing the conversion to double-ended ligation products in cell-free DNA by the polypeptide of SEQ ID NO: 38 and wild-type T4 DNA ligase, as described in Example 14.

Cell-free DNA samples isolated from human serum (BioChain) were prepared for ligation using the NEB Next® Ultra II™ End-Repair/A-tailing module in a 60 µl volume according to the manufacturer's instructions, using 10 ng of DNA sample per reaction. A ligation module was added directly to the product of the End-Repair/A-tailing reaction, such that the final concentrations of additional reaction components were 7 mM Tris pH 7.5, 9 mM MgCl2, 1 mM DTT, and 10% PEG 6000. An adapter comprised of two oligonucleotides (SEQ ID NO: 17 and SEQ ID NO: 18, annealed as described in Example 4) was added to final concentrations of 40 nM or 200 nM. Reactions were performed with final concentrations of 855 nM of a variant ligase (SEQ ID NO: 38) purified according to the method described in Example 7, or a commercial preparation of wild-type T4 DNA ligase ("Ultra-Pure" T4 DNA ligase (Rapid); Enzymatics), for a final total volume of 93.5 ul. Reactions were initiated with the addition of ligase, and were quenched after 15 minutes by the addition of HiPrep™ PCR SPRI beads (MagBio Genomics; 75 µl into a 93.5 µl reaction), then cleaned up according to the manufacturer's protocol. Samples were eluted in 25 ul of TE buffer (10 mM Tris, pH 7.5, 1 mM EDTA), and analyzed by capillary electrophoresis using the method described in Example 6. Percent conversion to double-end ligated products is shown in FIG. 6.

While the invention has been described with reference to the specific embodiments, various changes can be made and equivalents can be substituted to adapt to a particular situation, material, composition of matter, process, process step or steps, thereby achieving benefits of the invention without departing from the scope of what is claimed.

For all purposes in the United States of America, each and every publication and patent document cited in this disclosure is incorporated herein by reference as if each such publication or document was specifically and individually indicated to be incorporated herein by reference. Citation of publications and patent documents is not intended as an indication that any such document is pertinent prior art, nor does it constitute an admission as to its contents or date.

What is claimed is:

1. An engineered T4 DNA ligase comprising a polypeptide sequence, wherein the polypeptide sequence consists of SEQ ID NO:38.

* * * * *

SEQUENCE LISTING

```
<160> NUMBER OF SEQ ID NOS: 54

<210> SEQ ID NO 1
<211> LENGTH: 1464
<212> TYPE: DNA
<213> ORGANISM: Bacteriophage T4

<400> SEQUENCE: 1
atgattctta aaattctgaa cgaaatagca tctattggtt caactaaaca gaagcaagca      60
attcttgaaa agaataaaga taatgaattg cttaaacgag tatatcgtct gacttattct     120
cgtgggttac agtattatat caagaaatgg cctaaacctg gtattgctac ccagagtttt     180
ggaatgttga ctcttaccga tatgcttgac ttcattgaat tcacattagc tactcggaaa     240
ttgactggaa atgcagcaat tgaggaatta actggatata tcaccgatgg taaaaaagat     300
gatgttgaag ttttgcgtcg agtgatgatg cgagaccttg aatgtggtgc ttcagtatct     360
attgcaaaca aagtttggcc aggtttaatt cctgaacaac ctcaaatgct cgcaagttct     420
tatgatgaaa aaggcattaa taagaatatc aaatttccag cctttgctca gttaaaagct     480
gatggagctc ggtgttttgc tgaagttaga ggtgatgaat tagatgatgt tcgtctttta     540
tcacgagctg gtaatgaata tctaggatta gatcttctta aggaagagtt aattaaaatg     600
accgctgaag cccgccagat tcatccagaa ggtgtgttga ttgatggcga attggtatac     660
catgagcaag ttaaaaagga gccagaaggc ctagattttc tttttgatgc ttatcctgaa     720
aacagtaaag ctaaagaatt cgccgaagta gctgaatcac gtactgcttc taatggaatc     780
gccaataaat ctttaaaggg aaccatttct gaaaaagaag cacaatgcat gaagtttcag     840
gtctgggatt atgtcccgtt ggtagaaata tacagtcttc ctgcatttcg tttgaaatat     900
gatgtacgtt tttctaaact agaacaaatg acatctggat atgataaagt aattttaatt     960
gaaaaccagg tagtaaataa cctagatgaa gctaaggtaa tttataaaaa gtatattgac    1020
caaggtcttg aaggtattat tctcaaaaat atcgatggat tatgggaaaa tgctcgttca    1080
aaaaatcttt ataaatttaa agaagtaatt gatgttgatt taaaaattgt aggaatttat    1140
cctcaccgta aagaccctac taaagcgggt ggatttattc ttgagtcaga gtgtggaaaa    1200
attaaggtaa atgctggttc aggcttaaaa gataaagccg gtgtaaaatc gcatgaactt    1260
gaccgtactc gcattatgga aaaccaaaat tattatattg gaaaaattct agagtgcgaa    1320
tgcaacggtt ggttaaaatc tgatggccgc actgattacg ttaaattatt tcttccgatt    1380
gcgattcgtt tacgtgaaga taaaactaaa gctaatacat tcgaagatgt atttggtgat    1440
tttcatgagg taactggtct ataa                                           1464

<210> SEQ ID NO 2
<211> LENGTH: 487
<212> TYPE: PRT
<213> ORGANISM: Bacteriophage T4
```

```
<400> SEQUENCE: 2

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
                35                  40                  45

Lys Trp Pro Lys Pro Gly Ile Ala Thr Gln Ser Phe Gly Met Leu Thr
        50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Asp Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415
```

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 3
<211> LENGTH: 1497
<212> TYPE: DNA
<213> ORGANISM: Bacteriophage T4

<400> SEQUENCE: 3

```
atgcatcacc atcaccatca cggtggcagc ggtatgattc ttaaaattct gaacgaaata      60
gcatctattg gttcaactaa acagaagcaa gcaattcttg aaaagaataa agataatgaa     120
ttgcttaaac gagtatatcg tctgacttat tctcgtgggt tacagtatta tatcaagaaa     180
tggcctaaac ctggtattgc tacccagagt tttggaatgt tgactcttac cgatatgctt     240
gacttcattg aattcacatt agctactcgg aaattgactg aaatgcagc aattgaggaa      300
ttaactggat atatcaccga tggtaaaaaa gatgatgttg aagttttgcg tcgagtgatg     360
atgcgagacc ttgaatgtgg tgcttcagta tctattgcaa acaaagtttg gccaggttta     420
attcctgaac aacctcaaat gctcgcaagt tcttatgatg aaaaaggcat taataagaat     480
atcaaatttc cagcctttgc tcagttaaaa gctgatggga ctcggtgttt tgctgaagtt     540
agaggtgatg aattagatga tgttcgtctt ttatcacgag ctggtaatga atatctagga     600
ttagatcttc ttaaggaaga gttaattaaa atgaccgctg aagcccgcca gattcatcca     660
gaaggtgtgt tgattgatgg cgaattggta taccatgagc aagttaaaaa ggagccagaa     720
ggcctagatt ttcttttga tgcttatcct gaaaacagta agctaaaga attcgccgaa       780
gtagctgaat cacgtactgc ttctaatgga atcgccaata aatctttaaa gggaaccatt     840
tctgaaaaag aagcacaatg catgaagttt caggtctggg attatgtccc gttggtagaa     900
atatacagtc ttcctgcatt tcgtttgaaa tatgatgtac gttttctaa actagaacaa      960
atgcatctg gatatgataa agtaatttta attgaaaacc aggtagtaaa taacctagat     1020
gaagctaagg taatttataa aaagtatatt gaccaaggtc ttgaaggtat tattctcaaa    1080
aatatcgatg gattatggga aaatgctcgt tcaaaaaatc tttataaatt taagaagta    1140
attgatgttg atttaaaaat tgtaggaatt tatcctcacc gtaaagaccc tactaaagcg    1200
ggtggattta ttcttgagtc agagtgtgga aaaattaagg taaatgctgg ttcaggctta    1260
aaagataaag ccggtgtaaa atcgcatgaa cttgaccgta ctcgcattat ggaaaaccaa    1320
aattattata ttggaaaaat tctagagtgc gaatgcaacg gttggttaaa atctgatggc    1380
cgcactgatt acgttaaatt atttcttccg attgcgattc gtttacgtga agataaaact    1440
aaagctaata cattcgaaga tgtatttggt gattttcatg aggtaactgg tctataa       1497
```

<210> SEQ ID NO 4
<211> LENGTH: 498
<212> TYPE: PRT
<213> ORGANISM: Bacteriophage T4

<400> SEQUENCE: 4

```
Met His His His His His Gly Gly Ser Gly Met Ile Leu Lys Ile
1               5                   10                  15

Leu Asn Glu Ile Ala Ser Ile Gly Ser Thr Lys Gln Lys Gln Ala Ile
            20                  25                  30

Leu Glu Lys Asn Lys Asp Asn Glu Leu Leu Lys Arg Val Tyr Arg Leu
        35                  40                  45

Thr Tyr Ser Arg Gly Leu Gln Tyr Tyr Ile Lys Lys Trp Pro Lys Pro
    50                  55                  60

Gly Ile Ala Thr Gln Ser Phe Gly Met Leu Thr Leu Thr Asp Met Leu
65                  70                  75                  80

Asp Phe Ile Glu Phe Thr Leu Ala Thr Arg Lys Leu Thr Gly Asn Ala
                85                  90                  95

Ala Ile Glu Glu Leu Thr Gly Tyr Ile Thr Asp Gly Lys Lys Asp Asp
            100                 105                 110

Val Glu Val Leu Arg Arg Val Met Met Arg Asp Leu Glu Cys Gly Ala
        115                 120                 125

Ser Val Ser Ile Ala Asn Lys Val Trp Pro Gly Leu Ile Pro Glu Gln
    130                 135                 140

Pro Gln Met Leu Ala Ser Ser Tyr Asp Glu Lys Gly Ile Asn Lys Asn
145                 150                 155                 160

Ile Lys Phe Pro Ala Phe Ala Gln Leu Lys Ala Asp Gly Ala Arg Cys
                165                 170                 175

Phe Ala Glu Val Arg Gly Asp Glu Leu Asp Asp Val Arg Leu Leu Ser
            180                 185                 190

Arg Ala Gly Asn Glu Tyr Leu Gly Leu Asp Leu Leu Lys Glu Glu Leu
        195                 200                 205

Ile Lys Met Thr Ala Glu Ala Arg Gln Ile His Pro Glu Gly Val Leu
    210                 215                 220

Ile Asp Gly Glu Leu Val Tyr His Glu Gln Val Lys Lys Glu Pro Glu
225                 230                 235                 240

Gly Leu Asp Phe Leu Phe Asp Ala Tyr Pro Glu Asn Ser Lys Ala Lys
                245                 250                 255

Glu Phe Ala Glu Val Ala Glu Ser Arg Thr Ala Ser Asn Gly Ile Ala
            260                 265                 270

Asn Lys Ser Leu Lys Gly Thr Ile Ser Glu Lys Glu Ala Gln Cys Met
        275                 280                 285

Lys Phe Gln Val Trp Asp Tyr Val Pro Leu Val Glu Ile Tyr Ser Leu
    290                 295                 300

Pro Ala Phe Arg Leu Lys Tyr Asp Val Arg Phe Ser Lys Leu Glu Gln
305                 310                 315                 320

Met Thr Ser Gly Tyr Asp Lys Val Ile Leu Ile Glu Asn Gln Val Val
                325                 330                 335

Asn Asn Leu Asp Glu Ala Lys Val Ile Tyr Lys Tyr Ile Asp Gln
            340                 345                 350

Gly Leu Glu Gly Ile Ile Leu Lys Asn Ile Asp Gly Leu Trp Glu Asn
        355                 360                 365

Ala Arg Ser Lys Asn Leu Tyr Lys Phe Lys Glu Val Ile Asp Val Asp
    370                 375                 380

Leu Lys Ile Val Gly Ile Tyr Pro His Arg Lys Asp Pro Thr Lys Ala
385                 390                 395                 400

Gly Gly Phe Ile Leu Glu Ser Glu Cys Gly Lys Ile Lys Val Asn Ala
```

|  | 405 |  |  | 410 |  |  |  | 415 |  |  |  |
|---|---|---|---|---|---|---|---|---|---|---|---|

Gly Ser Gly Leu Lys Asp Lys Ala Gly Val Lys Ser His Glu Leu Asp
        420                 425                 430

Arg Thr Arg Ile Met Glu Asn Gln Asn Tyr Tyr Ile Gly Lys Ile Leu
        435                 440                 445

Glu Cys Glu Cys Asn Gly Trp Leu Lys Ser Asp Gly Arg Thr Asp Tyr
    450                 455                 460

Val Lys Leu Phe Leu Pro Ile Ala Ile Arg Leu Arg Glu Asp Lys Thr
465                 470                 475                 480

Lys Ala Asn Thr Phe Glu Asp Val Phe Gly Asp Phe His Glu Val Thr
        485                 490                 495

Gly Leu

<210> SEQ ID NO 5
<211> LENGTH: 1464
<212> TYPE: DNA
<213> ORGANISM: Artificial Sequence
<220> FEATURE:
<223> OTHER INFORMATION: Synthetic T4 DNA ligase

<400> SEQUENCE: 5

| atgattctta aaattctgaa cgaaattgca agcattggtt ccactaaaca aaaacaagcc | 60 |
|---|---|
| attctggaaa aaaataagga caatgaactg ttaaagcgcg tgtatcgcct gacctattcg | 120 |
| cgtggcctgc aatactatat taaaaaatgg cccaaaccgg gcattgcgac gcagagcttc | 180 |
| ggcatgctga ccctgaccga tatgctggat tttatcgagt ttactcttgc gacgcgcaaa | 240 |
| cttaccggca acgctgctat tgaagaattg acgggctata ttaccgatgg caaaaaagat | 300 |
| gatgttgagg tgctgcgtcg cgtcatgatg cgtgatctgg agtgcggtgc gtcagtgagc | 360 |
| atcgctaaca aagtgtggcc gggtttgatc ccggaacagc cacagatgct tgcaagcagc | 420 |
| tacgatgaaa agggcattaa caaaaatatc aaatttccgg ctttcgccca gctgaaagcg | 480 |
| gatggcgcgc gctgcttcgc cgaggtacgc ggtgacgaac tggacgacgt tcgtctgctg | 540 |
| tctcgcgctg caatgaata tctgggtctg gatctgctga agaagaact gattaagatg | 600 |
| accgccgagg cgcgccaaat ccaccccgaa ggggtgctga ttgatggcga actggtgtat | 660 |
| cacgaacagg ttaaaaagga gccggagggg ttggatttcc tgtttgatgc ctacccggag | 720 |
| aatagcaaag cgaaagaatt tgcggaagtg gcggaatccc gcaccgcaag caatggtatc | 780 |
| gcaaataaat cgctgaaggg caccattcct gagaagaag cacagtgtat gaagttccag | 840 |
| gtgtgggact acgtgccact ggttgagatc tactccctgc agcgtttcg cctgaaatac | 900 |
| gatgtgcgtt tttcaaaact ggaacagatg acgagcggat atgataaagt aattttaatc | 960 |
| gagaaccagg tcgtgaacaa cctggatgaa gcaaaagtta tctataaaaa atatattgat | 1020 |
| cagggcttag aaggcattat cctgaagaac attgatggcc tttgggaaaa tgcacgcagc | 1080 |
| aaaaaccctgt ataaatttaa agaagtgatt gatgtagatc tgaagattgt tggtatttac | 1140 |
| ccgcatcgca agacccgac caaagcaggt ggtttcatcc tggaatctga atgcggtaaa | 1200 |
| attaaagtga acgcaggcag tggtttgaaa gataaagctg gtgttaaaag tcacgaactg | 1260 |
| gatcgcacgc gcatcatgga aaaccagaac tattatatcg gcaaaattct ggaatgcgag | 1320 |
| tgcaacgggt ggcttaagag cgacgggcgc acggactatg ttaaattgtt cctgccgatt | 1380 |
| gcgattcgcc ttcgcgaaga caaaactaag gcgaatactt tcgaagatgt gttcggtgat | 1440 |
| tttcatgaag tcacgggtct gtaa | 1464 |

```
<210> SEQ ID NO 6
<211> LENGTH: 487
<212> TYPE: PRT
<213> ORGANISM: Artificial Sequence
<220> FEATURE:
<223> OTHER INFORMATION: Synthetic T4 DNA ligase

<400> SEQUENCE: 6

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365
```

```
Val Ile Asp Val Asp Leu Lys Ile Val Gly Ile Tyr Pro His Arg Lys
        370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
                420                 425                 430

Ile Gly Lys Ile Leu Glu Cys Glu Cys Asn Gly Trp Leu Lys Ser Asp
                435                 440                 445

Gly Arg Thr Asp Tyr Val Lys Leu Phe Leu Pro Ile Ala Ile Arg Leu
        450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 7
<211> LENGTH: 50
<212> TYPE: DNA
<213> ORGANISM: Artificial Sequence
<220> FEATURE:
<223> OTHER INFORMATION: Artificial Oligonucleotides

<400> SEQUENCE: 7
tgctactcat cctagtcctg ttgctgccaa gctatttaat atcatgcaca           50

<210> SEQ ID NO 8
<211> LENGTH: 49
<212> TYPE: DNA
<213> ORGANISM: Artificial Sequence
<220> FEATURE:
<223> OTHER INFORMATION: Synthetic Oligonucleotides

<400> SEQUENCE: 8
tgcatgatat aaatagctt ggcagcaaca ggactaggat gagtagcaa             49

<210> SEQ ID NO 9
<211> LENGTH: 21
<212> TYPE: DNA
<213> ORGANISM: Artificial Sequence
<220> FEATURE:
<223> OTHER INFORMATION: Synthetic Oligonucleotides
<220> FEATURE:
<221> NAME/KEY: misc_feature
<222> LOCATION: (20)..(20)
<223> OTHER INFORMATION: n is a, c, g, or t

<400> SEQUENCE: 9
acacgacgct cttccgatcn t                                          21

<210> SEQ ID NO 10
<211> LENGTH: 19
<212> TYPE: DNA
<213> ORGANISM: Artificial Sequence
<220> FEATURE:
<223> OTHER INFORMATION: Synthetic Oligonucleotides

<400> SEQUENCE: 10
gatcggaaga gcgtcgtgt                                             19

<210> SEQ ID NO 11
<211> LENGTH: 50
```

```
<212> TYPE: DNA
<213> ORGANISM: Artificial Sequence
<220> FEATURE:
<223> OTHER INFORMATION: Synthetic Oligonucleotides

<400> SEQUENCE: 11
tgctactcat cctagtcctg ttgctgccaa gctatttaat atcatgcaca         50

<210> SEQ ID NO 12
<211> LENGTH: 50
<212> TYPE: DNA
<213> ORGANISM: Artificial Sequence
<220> FEATURE:
<223> OTHER INFORMATION: Synthetic Oligonucleotides

<400> SEQUENCE: 12
gtgcatgata ttaaatagct tggcagcaac aggactagga tgagtagcaa         50

<210> SEQ ID NO 13
<211> LENGTH: 21
<212> TYPE: DNA
<213> ORGANISM: Artificial Sequence
<220> FEATURE:
<223> OTHER INFORMATION: Synthetic Oligonucleotides
<220> FEATURE:
<221> NAME/KEY: misc_feature
<222> LOCATION: (20)..(20)
<223> OTHER INFORMATION: n is a, c, g, or t

<400> SEQUENCE: 13
acacgacgct cttccgatcn t                                        21

<210> SEQ ID NO 14
<211> LENGTH: 19
<212> TYPE: DNA
<213> ORGANISM: Artificial Sequence
<220> FEATURE:
<223> OTHER INFORMATION: Synthetic Oligonucleotides

<400> SEQUENCE: 14
gatcggaaga gcgtcgtgt                                           19

<210> SEQ ID NO 15
<211> LENGTH: 65
<212> TYPE: DNA
<213> ORGANISM: Artificial Sequence
<220> FEATURE:
<223> OTHER INFORMATION: Synthetic Oligonucleotides
<220> FEATURE:
<221> NAME/KEY: misc_feature
<222> LOCATION: (64)..(64)
<223> OTHER INFORMATION: n is a, c, g, or t

<400> SEQUENCE: 15
gatcggaaga gcacacgtct gaactccagt cacactcttt ccctacacga cgctcttccg    60 atcnt                                                          65

<210> SEQ ID NO 16
<211> LENGTH: 19
<212> TYPE: DNA
<213> ORGANISM: Artificial Sequence
<220> FEATURE:
<223> OTHER INFORMATION: Synthetic Oligonucleotides

<400> SEQUENCE: 16
gatcggaaga gcgtcgtgt                                           19
```

<210> SEQ ID NO 17
<211> LENGTH: 59
<212> TYPE: DNA
<213> ORGANISM: Artificial Sequence
<220> FEATURE:
<223> OTHER INFORMATION: Synthetic Oligonucleotides
<220> FEATURE:
<221> NAME/KEY: misc_feature
<222> LOCATION: (58)..(58)
<223> OTHER INFORMATION: n is a, c, g, or t

<400> SEQUENCE: 17
aatgatacgg cgaccaccga gatctacact ctttccctac acgacgctct tccgatcnt        59

<210> SEQ ID NO 18
<211> LENGTH: 63
<212> TYPE: DNA
<213> ORGANISM: Artificial Sequence
<220> FEATURE:
<223> OTHER INFORMATION: Synthetic Oligonucleotides

<400> SEQUENCE: 18
gatcggaaga gcacacgtct gaactccagt cacatcacga tctcgtatgc cgtcttctgc        60
ttg        63

<210> SEQ ID NO 19
<211> LENGTH: 22
<212> TYPE: DNA
<213> ORGANISM: Artificial Sequence
<220> FEATURE:
<223> OTHER INFORMATION: Synthetic Oligonucleotides

<400> SEQUENCE: 19
aagccggtgt aaaatcgcat ga        22

<210> SEQ ID NO 20
<211> LENGTH: 24
<212> TYPE: DNA
<213> ORGANISM: Artificial Sequence
<220> FEATURE:
<223> OTHER INFORMATION: Synthetic Oligonucleotides

<400> SEQUENCE: 20
agtaaacgaa tcgcaatcgg aaga        24

<210> SEQ ID NO 21
<211> LENGTH: 22
<212> TYPE: DNA
<213> ORGANISM: Artificial Sequence
<220> FEATURE:
<223> OTHER INFORMATION: Synthetic Oligonucleotides

<400> SEQUENCE: 21
cagccggtgt aaaatcgcat ga        22

<210> SEQ ID NO 22
<211> LENGTH: 24
<212> TYPE: DNA
<213> ORGANISM: Artificial Sequence
<220> FEATURE:
<223> OTHER INFORMATION: Synthetic Oligonucleotides

<400> SEQUENCE: 22
cgtaaacgaa tcgcaatcgg aaga        24

```
<210> SEQ ID NO 23
<211> LENGTH: 22
<212> TYPE: DNA
<213> ORGANISM: Artificial Sequence
<220> FEATURE:
<223> OTHER INFORMATION: Synthetic Oligonucleotides

<400> SEQUENCE: 23
gagccggtgt aaaatcgcat ga                                              22

<210> SEQ ID NO 24
<211> LENGTH: 24
<212> TYPE: DNA
<213> ORGANISM: Artificial Sequence
<220> FEATURE:
<223> OTHER INFORMATION: Synthetic Oligonucleotides

<400> SEQUENCE: 24
ggtaaacgaa tcgcaatcgg aaga                                            24

<210> SEQ ID NO 25
<211> LENGTH: 22
<212> TYPE: DNA
<213> ORGANISM: Artificial Sequence
<220> FEATURE:
<223> OTHER INFORMATION: Synthetic Oligonucleotides

<400> SEQUENCE: 25
tagccggtgt aaaatcgcat ga                                              22

<210> SEQ ID NO 26
<211> LENGTH: 24
<212> TYPE: DNA
<213> ORGANISM: Artificial Sequence
<220> FEATURE:
<223> OTHER INFORMATION: Synthetic Oligonucleotides

<400> SEQUENCE: 26
tgtaaacgaa tcgcaatcgg aaga                                            24

<210> SEQ ID NO 27
<211> LENGTH: 160
<212> TYPE: DNA
<213> ORGANISM: Artificial Sequence
<220> FEATURE:
<223> OTHER INFORMATION: Synthetic Oligonucleotides

<400> SEQUENCE: 27
aagccggtgt aaaatcgcat gaacttgacc gtactcgcat tatggaaaac caaaattatt     60
atattggaaa aattctagag tgcgaatgca acggttggtt aaaatctgat ggccgcactg    120
attacgttaa attatttctt ccgattgcga ttcgtttaca                          160

<210> SEQ ID NO 28
<211> LENGTH: 160
<212> TYPE: DNA
<213> ORGANISM: Artificial Sequence
<220> FEATURE:
<223> OTHER INFORMATION: Synthetic Oligonucleotides

<400> SEQUENCE: 28
cagccggtgt aaaatcgcat gaacttgacc gtactcgcat tatggaaaac caaaattatt     60
atattggaaa aattctagag tgcgaatgca acggttggtt aaaatctgat ggccgcactg    120
attacgttaa attatttctt ccgattgcga ttcgtttacc                          160
```

<210> SEQ ID NO 29
<211> LENGTH: 160
<212> TYPE: DNA
<213> ORGANISM: Artificial Sequence
<220> FEATURE:
<223> OTHER INFORMATION: Synthetic Oligonucleotides

<400> SEQUENCE: 29

```
gagccggtgt aaaatcgcat gaacttgacc gtactcgcat tatggaaaac caaaattatt      60
atattggaaa aattctagag tgcgaatgca acggttggtt aaaatctgat ggccgcactg     120
attacgttaa attatttctt ccgattgcga ttcgtttacg                           160
```

<210> SEQ ID NO 30
<211> LENGTH: 160
<212> TYPE: DNA
<213> ORGANISM: Artificial Sequence
<220> FEATURE:
<223> OTHER INFORMATION: Synthetic Oligonucleotides

<400> SEQUENCE: 30

```
tagccggtgt aaaatcgcat gaacttgacc gtactcgcat tatggaaaac caaaattatt      60
atattggaaa aattctagag tgcgaatgca acggttggtt aaaatctgat ggccgcactg     120
attacgttaa attatttctt ccgattgcga ttcgtttact                           160
```

<210> SEQ ID NO 31
<211> LENGTH: 1464
<212> TYPE: DNA
<213> ORGANISM: Artificial Sequence
<220> FEATURE:
<223> OTHER INFORMATION: engineered ligase variant

<400> SEQUENCE: 31

```
atgattctta aaattctgaa cgaaattgca agcattggtt ccactaaaca aaaacaagcc      60
attctggaaa aaataaaga caatgaactg ttaaagcgcg tgtatcgcct gacctattcg     120
cgtggcctgc aatactatat taaaaaatgg cccaaaccgg gcattgcgac gcagagcttc     180
ggcatgctga ccctgaccga tatgctggat tttatcgagt ttactcttgc gacgcgcaaa     240
cttaccggca acgctgctat tagagaattg acgggctata ttaccgatgg caaaaaagat     300
gatgttgagg tgctgcgtcg cgtcatgatg cgtgatctgg agtgcggtgc gtcagtgagc     360
atcgctaaca aagtgtggcc gggtttgatc ccggaacagc cacagatgct tgcaagcagc     420
tacgatgaaa agggcattaa caaaaatatc aaatttccgg ctttcgccca gctgaaagcg     480
gatggcgcgc gctgcttcgc cgaggtacgc ggtgacgaac tggacgacgt tcgtctgctg     540
tctcgcgctg gcaatgaata tctgggtctg gatctgctga agaagaact gattaagatg     600 accgccgagg cgcgccaaat ccaccccgaa ggggtgctga ttgatggcga actggtgtat     660
cacgaacagg ttgcaaaaga gccgagggg ttgatttcc tgtttgatgc ctacccggag     720
aatagcaaag cgaaagaatt tgcggaagtg gcggaatccc gcaccgcaag caatggtatc     780
gcaaataaat cgctgaaggg caccatttct gagaagaag cacagtgtat gaagttccag     840
gtgtgggact acgtgccact ggttgagatc tactccctgc cagcgtttcg cctgaaatac     900
gatgtgcgtt tttcaaaact ggaacagatg acgagcggat atgataaagt aatttaatc     960 gagaaccagg tcgtgaacaa cctggatgaa gcaaagtta tctataaaaa atatattgat    1020
cagggcttag aaggcattat cctgaagaac attgatggcc tttgggaaaa tgcacgcagc    1080
aaaaacctgt ataaatttaa agaagtgatt gatgtagatc tgaagattgt tggtatttac    1140
```

```
ccgcatcgca aagacccgac caaagcaggt ggtttcatcc tggaatctga atgcggtaaa    1200
attaaagtga acgcaggcag tggtttgaaa gataaagctg gtgttaaaag tcacgaactg    1260
gatcgcacgc gcatcatgga aaccagaac tattatatcg gcaaaattct ggaatgcaaa     1320
tgcaacgggt ggcttaagag cgatgggcgc aaagactatg ttaaattgtt cctgccgatt    1380
gcgattcgcc ttcgcgaaga caaaactaag gcgaatactt tcgaagatgt gttcggtgat    1440
tttcatgaag tcacgggtct gtaa                                           1464
```

<210> SEQ ID NO 32
<211> LENGTH: 487
<212> TYPE: PRT
<213> ORGANISM: Artificial Sequence
<220> FEATURE:
<223> OTHER INFORMATION: engineered ligase variant

<400> SEQUENCE: 32

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Arg Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Ala Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
    290                 295                 300
```

```
Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
            325                 330                 335

Lys Tyr Ile Asp Gln Gly Leu Glu Gly Ile Ile Leu Lys Asn Ile Asp
        340                 345                 350

Gly Leu Trp Glu Asn Ala Arg Ser Lys Asn Leu Tyr Lys Phe Lys Glu
    355                 360                 365

Val Ile Asp Val Asp Leu Lys Ile Val Gly Ile Tyr Pro His Arg Lys
370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
            405                 410                 415

Ser His Glu Leu Asp Arg Thr Arg Ile Met Glu Asn Gln Asn Tyr Tyr
        420                 425                 430

Ile Gly Lys Ile Leu Glu Cys Lys Cys Asn Gly Trp Leu Lys Ser Asp
    435                 440                 445

Gly Arg Lys Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu
            485

<210> SEQ ID NO 33
<211> LENGTH: 1464
<212> TYPE: DNA
<213> ORGANISM: Artificial Sequence
<220> FEATURE:
<223> OTHER INFORMATION: engineered ligase variant

<400> SEQUENCE: 33
atgattctta aaattctgaa cgaaattgca agcattggtt ccactaaaca aaaacaagcc      60
attctggaaa aaataaaga caatgaactg ttaaagcgcg tgtatcgcct gacctattcg     120
cgtggcctgc aatactatat taaaaaatgg cccaaaccgg gcattgcgac gcagagcttc     180
ggcatgctga ccctgaccga tatgctggat tttatcgagt ttactcttgc gacgcgcaaa     240
cttaccggca cgctgctat tagagaattg acgggctata ttaccgatgg caaaaaagat     300
gatgttgagg tgctgcgtcg cgtcatgatg cgtgatctgg agtgcggtgc gtcagtgagc     360
atcgctaaca aagtgtggaa gggtttgatc ccggaacagc cacagatgct tgcaagcagc     420
tacgatgaaa agggcattaa caaaaatatc aaatttccgg ctttcgccca gctgaaagcg     480
gatggcgcgc gctgcttcgc cgaggtacgc ggtgacgaac tggacgacgt tcgtctgctg     540
tctcgcgctg gcaatgaata tctgggtctg atctgctga agaagaact gattaagatg     600
accgccgagg cgcgccaaat ccaccccgaa ggggtgctga ttgatggcga actggtgtat     660
cacgaacagg ttgcaaaaga gccggagggg ttggatttcc tgtttgatgc ctacccggag     720
aatagcaaag cgaaagaatt tgcggaagtg gcggaatccc gcaccgcaag caatggtatc     780
gcaaataaat cgctgaaggg caccattct gagaaagaag cacagtgtat gaagttccag     840
gtgtgggact acgtgccact ggttgagatc tactccctgc agcgtttcg cctgaaatac     900
gatgtgcgtt ttcaaaaact ggaacagatg acgagcggat atgataaagt aatttaatc     960
```

-continued

```
gagaaccagg tcgtgaacaa cctggatgaa gcaaaagtta tctataaaaa atatattgat    1020
cagggcttag aaggcattat cctgaagaac attgatggcc tttgggaaaa tgcacgcagc    1080
aaaaacctgt ataaatttaa agaagtgatt gatgtagatc tgaagattgt tggtatttac    1140
ccgcatcgca aagacccgac caaagcaggt ggtttcatcc tggaatctga atgcggtaaa    1200
attaaagtga acgcaggcag tggtttgaaa gataaagctg gtgttaaaag tcacgaactg    1260
gatcgcacgc gcatcatgga aaaccagaac tattatatcg gcaaaattct ggaatgcaaa    1320
tgcaacgggt ggcttaagag cgatgggcgc aaagactatg ttaaattgtt cctgccgatt    1380
gcgattcgcc ttcgcgaaga caaaactaag gcgaatactt tcgaagatgt gttcggtgat    1440
tttcatgaag tcacgggtct gtaa                                           1464
```

<210> SEQ ID NO 34
<211> LENGTH: 487
<212> TYPE: PRT
<213> ORGANISM: Artificial Sequence
<220> FEATURE:
<223> OTHER INFORMATION: engineered ligase variant

<400> SEQUENCE: 34

```
Met Ile Leu Lys Ile Leu Asn Glu Ile Ala Ser Ile Gly Ser Thr Lys
 1               5                  10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Arg Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Lys Gly
        115                 120                 125

Leu Ile Pro Glu Gln Pro Gln Met Leu Ala Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Ala Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270
```

```
Glu Ala Gln Cys Met Lys Phe Gln Val Trp Asp Tyr Val Pro Leu Val
            275                 280                 285

Glu Ile Tyr Ser Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Asp Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Lys Cys Asn Gly Trp Leu Lys Ser Asp
        435                 440                 445

Gly Arg Lys Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 35
<211> LENGTH: 1467
<212> TYPE: DNA
<213> ORGANISM: Artificial Sequence
<220> FEATURE:
<223> OTHER INFORMATION: engineered ligase variant

<400> SEQUENCE: 35
atgattctta aaattctgaa cgaaattgca agcattggtt ccactaaaca aaaacaagcc      60
attctggaaa aaataaaga caatgaactg ttaaagcgcg tgtatcgcct gacctattcg      120
cgtggcctgc aatactatat taaaaaatgg cccaaaccgg gcattgcgac gcagagcttc      180
ggcatgacta ccctgaccga tatgctggat tttatcgagt ttactcttgc gacgcgcaaa      240
cttaccggca acgctgctat tagagaattg acgggctata ttaccgatgg caaaaaagat      300
gatgttgagg tgctgcgtcg cgtcatgatg cgtgatctgg agtgcggtgc gtcagtgagc      360
atcgctaaca aagtgtggaa gggtttgatc ccggaacagc cacagatgct tgcaagcagc      420
tacgatgaaa agggcattaa caaaagaatc aaatttccgg ctttcgccca gctgaaagcg      480
gatggcgcgc gctgcttcgc cgaggtacgc ggtgacgaac tggacgacgt tcgtctgctg      540
tctcgcgctg gcaatgaata tctgggtctg atctgctga agaagaact gattaagatg      600 accgccgagg cgcgccaaat ccaccccgaa ggggtgctga ttgatggcga actggtgtat      660
cacgaacagg ttgcaaaaga gccggagggg ttggatttcc tgtttgatgc ttacccgcct      720
aatagcaaag cgaaagaatt tgcggaagtg gcggaatccc gcaccgcaag caatggtatc      780
gcaaataaat cgctgaaggg caccatttct gagaagaag cacagtgtat gaagttccag      840
```

-continued

```
gtgtgggact acgtgccact ggttgagatc tactccctgc cagcgtttcg cctgaaatac    900
gatgtgcgtt tttcaaaact ggaacagatg acgagcggat atgataaagt aattttaatc    960
gagaaccagg tcgtgaacaa cctggatgaa gcaaaagtta tctataaaaa atatattgat   1020
cagggcttag aaggcattat cctgaagaac attgatggcc tttgggaaaa tgcacgcagc   1080
aaaaacctgt ataaatttaa agaagtgatt tgggtagatc tgaagattgt tggtatttac   1140
ccgcatcgca aagacccgac caaagcaggt ggtttcatcc tggaatctga atgcggtaaa   1200
attaaagtga acgcaggcag tggtttgaaa gataaagctg gtgttaaaag tcacgaactg   1260
gatcgcacgc gcatcatgga aaaccagaac tattatatcg gcaaaattct ggaatgcaaa   1320
tgcaacgggt ggcttaagag cgatgggcgc aaaccctatg tgaaattgtt cctgccgatt   1380
gcgattcgcc ttcgcgaaga caaaactaag gcgaatactt tcgaagatgt gttcggtgat   1440
tttcatgaag tcactggtct gtaataa                                       1467
```

<210> SEQ ID NO 36
<211> LENGTH: 487
<212> TYPE: PRT
<213> ORGANISM: Artificial Sequence
<220> FEATURE:
<223> OTHER INFORMATION: engineered ligase variant

<400> SEQUENCE: 36

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Thr Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Arg Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Lys Gly
        115                 120                 125

Leu Ile Pro Glu Gln Pro Gln Met Leu Ala Ser Ser Tyr Asp Glu Lys
    130                 135                 140

Gly Ile Asn Lys Arg Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Ala Lys Glu Pro Glu Gly Leu Asp Phe Leu Phe Asp Ala Tyr Pro Pro
225                 230                 235                 240

Asn Ser Lys Ala Lys Glu Phe Ala Glu Val Ala Glu Ser Arg Thr Ala
```

| | | | | 245 | | | | 250 | | | | 255 | | |
|---|---|---|---|---|---|---|---|---|---|---|---|---|---|---|
| Ser | Asn | Gly | Ile | Ala | Asn | Lys | Ser | Leu | Lys | Gly | Thr | Ile | Ser | Glu | Lys |
| | | | 260 | | | | | 265 | | | | 270 | | | |
| Glu | Ala | Gln | Cys | Met | Lys | Phe | Gln | Val | Trp | Asp | Tyr | Val | Pro | Leu | Val |
| | | | 275 | | | | | 280 | | | | | 285 | | |
| Glu | Ile | Tyr | Ser | Leu | Pro | Ala | Phe | Arg | Leu | Lys | Tyr | Asp | Val | Arg | Phe |
| | | 290 | | | | | 295 | | | | | 300 | | | |
| Ser | Lys | Leu | Glu | Gln | Met | Thr | Ser | Gly | Tyr | Asp | Lys | Val | Ile | Leu | Ile |
| 305 | | | | | 310 | | | | | 315 | | | | | 320 |
| Glu | Asn | Gln | Val | Val | Asn | Asn | Leu | Asp | Glu | Ala | Lys | Val | Ile | Tyr | Lys |
| | | | | 325 | | | | | 330 | | | | | 335 | |
| Lys | Tyr | Ile | Asp | Gln | Gly | Leu | Glu | Gly | Ile | Ile | Leu | Lys | Asn | Ile | Asp |
| | | | 340 | | | | | 345 | | | | | 350 | | |
| Gly | Leu | Trp | Glu | Asn | Ala | Arg | Ser | Lys | Asn | Leu | Tyr | Lys | Phe | Lys | Glu |
| | | | | 355 | | | | | 360 | | | | | 365 | |
| Val | Ile | Trp | Val | Asp | Leu | Lys | Ile | Val | Gly | Ile | Tyr | Pro | His | Arg | Lys |
| | | 370 | | | | | 375 | | | | | 380 | | | |
| Asp | Pro | Thr | Lys | Ala | Gly | Gly | Phe | Ile | Leu | Glu | Ser | Glu | Cys | Gly | Lys |
| 385 | | | | | 390 | | | | | 395 | | | | | 400 |
| Ile | Lys | Val | Asn | Ala | Gly | Ser | Gly | Leu | Lys | Asp | Lys | Ala | Gly | Val | Lys |
| | | | | 405 | | | | | 410 | | | | | 415 | |
| Ser | His | Glu | Leu | Asp | Arg | Thr | Arg | Ile | Met | Glu | Asn | Gln | Asn | Tyr | Tyr |
| | | | 420 | | | | | 425 | | | | | 430 | | |
| Ile | Gly | Lys | Ile | Leu | Glu | Cys | Lys | Cys | Asn | Gly | Trp | Leu | Lys | Ser | Asp |
| | | | 435 | | | | | 440 | | | | | 445 | | |
| Gly | Arg | Lys | Pro | Tyr | Val | Lys | Leu | Phe | Leu | Pro | Ile | Ala | Ile | Arg | Leu |
| | | | 450 | | | | | 455 | | | | | 460 | | |
| Arg | Glu | Asp | Lys | Thr | Lys | Ala | Asn | Thr | Phe | Glu | Asp | Val | Phe | Gly | Asp |
| 465 | | | | | 470 | | | | | 475 | | | | | 480 |
| Phe | His | Glu | Val | Thr | Gly | Leu | | | | | | | | | |
| | | | 485 | | | | | | | | | | | | |

<210> SEQ ID NO 37
<211> LENGTH: 1464
<212> TYPE: DNA
<213> ORGANISM: Artificial Sequence
<220> FEATURE:
<223> OTHER INFORMATION: engineered ligase variant

<400> SEQUENCE: 37

| | |
|---|---|
| atgattctta aaattctgaa cgaaattgca agcattggtt ccactaaaca aaaaaaagcc | 60 |
| attctggaaa aaataaaga caatgaactg ttaaagcgcg tgtatcgcct gacctattcg | 120 |
| cgtggcctgc aatactatat taaaaaatgg cccaaaccgg cattgcgac gcagagcttc | 180 |
| ggcatgacta ccctgaccga tatgctggat tttatcgagt ttactcttgc gacgcgcaaa | 240 |
| cttaccggca acgctgctat tagagaattg acgggctata ttaccgatgg caaaaaagat | 300 |
| gatgttgagg tgctgcgtcg cgtcatgatg cgtgatctgg agtgcggtgc gtcagtgagc | 360 |
| atcgctaaca agtgtggaa gggtttgatc ccggaacagc cacagatgct tgcaagcagc | 420 |
| tacgatgaaa agggcattaa caaaaatatc aaatttccgg ctttcgccca gctgaaagcg | 480 |
| gatggcgcgc gctgcttcgc cgaggtacgc ggtgacgaac tggacgacgt tcgtctgctg | 540 |
| tctcgcgctg gcaatgaata tctgggtctg gatctgctga agaagaact gattaagatg | 600 |
| accgccgagg cgcgccaaat ccaccccgaa ggggtgctga ttgatggcga actggtgtat | 660 |

```
cacgaacagg ttgcaaaaga gccggagggg ttggatgctc tgtttgatcg atacccggaa    720
aatagcaaag cgaaagaatt tgcggaagtg gcggaatccc gcaccgcaag caatggtatc    780
gcaaataaat cgctgaaggg caccatttct gagaaagaag cacagtgtat gaagttccag    840
gtgtgggact acgtgccact ggttgagatc tactccctgc cagcgtttcg cctgaaatac    900
gatgtgcgtt tttcaaaact ggaacagatg acgagcggat atgataaagt aattttaatc    960
gagaaccagg tcgtgaacaa cctggatgaa gcaaaagtta tctataaaaa atatattgat   1020
cagggcttag aaggcattat cctgaagaac attgatggcc tttgggaaaa tgcacgcagc   1080
aaaaacctgt ataaatttaa agaagtgatt tgggtagatc tgaagattgt tggtatttac   1140
ccgcatcgca aagacccgac caaagcaggt ggtttcatcc tggaatctga atgcggtaaa   1200
attaaagtga acgcaggcag tggtttgaaa gataaagctg gtgttaaaag tcacgaactg   1260
gatcgcacgc gcatcatgga aaccagaac tattatatcg gcaaaattct ggaatgcaaa   1320
tgcaacgggt ggcttaagag cgatgggcgc aaaccctatg tgaaattgtt cctgccgatt   1380
gcgattcgcc ttcgcgaaga caaaactaag gcgaatactt tcgaagatgt gttcggtgat   1440
tttcatgaag tcacgggtct gtaa                                           1464
```

<210> SEQ ID NO 38
<211> LENGTH: 487
<212> TYPE: PRT
<213> ORGANISM: Artificial Sequence
<220> FEATURE:
<223> OTHER INFORMATION: engineered ligase variant

<400> SEQUENCE: 38

```
Met Ile Leu Lys Ile Leu Asn Glu Ile Ala Ser Ile Gly Ser Thr Lys
1               5                   10                  15

Gln Lys Lys Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Thr Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Arg Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Lys Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220
```

```
Ala Lys Glu Pro Glu Gly Leu Asp Ala Leu Phe Asp Arg Tyr Pro Glu
225                 230                 235                 240

Asn Ser Lys Ala Lys Glu Phe Ala Glu Val Ala Glu Ser Arg Thr Ala
            245                 250                 255

Ser Asn Gly Ile Ala Asn Lys Ser Leu Lys Gly Thr Ile Ser Glu Lys
        260                 265                 270

Glu Ala Gln Cys Met Lys Phe Gln Val Trp Asp Tyr Val Pro Leu Val
    275                 280                 285

Glu Ile Tyr Ser Leu Pro Ala Phe Arg Leu Lys Tyr Asp Val Arg Phe
290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Trp Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Lys Cys Asn Gly Trp Leu Lys Ser Asp
        435                 440                 445

Gly Arg Lys Pro Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 39
<211> LENGTH: 1464
<212> TYPE: DNA
<213> ORGANISM: Artificial Sequence
<220> FEATURE:
<223> OTHER INFORMATION: engineered ligase variant

<400> SEQUENCE: 39
atgattctta aaattctgaa cgaaattgca agcattggtt ccactaaaca aaacaagcc      60 attctggaaa aaataaaga caatgaactg ttaaagcgcg tgtatcgcct gacctattcg     120
cgtggcctgc aatactatat taaaaaatgg cccaaaccgg gcattgcgac gcagagcttc     180
ggcatgctta ccctgaccga tatgctggat tttatcgagt ttactcttgc gacgcgcaaa     240
cttaccggca acgctgctat tagaaaattg acgggctata ttaccgatgg caaaaaagat     300
gatgttgagg tgctgcgtcg cgtcatgatg cgtgatctgg agtgcggtgc gtcagtgagc     360
atcgctaaca agtgtggaa gggtttgatc ccggaacagc cacagatgct tgcaagcagc     420
tacgatgaaa agggcattaa caaaaatatc aaatttccgg ctttcgccca gctgaaagcg     480
gatggcgcgc gctgcttcgc cgaggtacgc ggtgacgaac tggacgacgt tcgtctgctg     540
```

-continued

```
tctcgcgctg gcaatgaata tctgggtctg gatctgctga aagaagaact gattaagatg      600
accgccgagg cgcgccaaat ccaccccgaa ggggtgctga ttgatggcga actggtgtat      660
cacgaacagg ttgcaaaaga gccggagggg ttggatgctc tgtttgatcg ataccecgcct    720 aatagcaaag cgaaagaatt tgcggaagtg gcggaatccc gcaccgcaag caatggtatc      780
gcaaataaat cgctgaaggg caccatttct gagaaagaag cacagtgtat gaagttccag      840
gtgtgggact acgtgccact ggttgagatc tactccctgc cagcgtttcg cctgaaatac      900
gatgtgcgtt tttcaaaact ggaacagatg acgagcggat atgataaagt aattttaatc      960
gagaaccagg tcgtgaacaa cctggatgaa gcaaaagtta tctataaaaa atatattgat     1020
cagggcttag aaggcattat cctgaagaac attgatggcc tttgggaaaa tgcacgcagc     1080
aaaaacctgt ataaatttaa agaagtgatt gatgtagatc tgaagattgt tggtatttac     1140
ccgcatcgca aagacccgac caaagcaggt ggtttcatcc tggaatctga atgcggtaaa     1200
attaaagtga acgcaggcag tggtttgaaa gataaagctg tgttaaaag tcacgaactg      1260 gatcgcacgc gcatcatgga aaaccagaac tattatatcg gcaaaattct ggagtgcaaa     1320
tgcaacgggt ggcttaagag cgctgggcgc aaagacggtc tgaaattgtt cctgccgatt     1380
gcgattcgcc ttcgcgaaga caaaactaag gcgaatactt tcgaagatgt gttcggtgat     1440
tttcatgaag tcacgggtct gtaa                                           1464
```

<210> SEQ ID NO 40
<211> LENGTH: 487
<212> TYPE: PRT
<213> ORGANISM: Artificial Sequence
<220> FEATURE:
<223> OTHER INFORMATION: engineered ligase variant

<400> SEQUENCE: 40

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Arg Lys Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Lys Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190
```

Leu Lys Glu Glu Leu Ile Lys Met Thr Ala Glu Ala Arg Gln Ile His
            195                 200                 205
Pro Glu Gly Val Leu Ile Asp Gly Glu Leu Val Tyr His Glu Gln Val
        210                 215                 220
Ala Lys Glu Pro Glu Gly Leu Asp Ala Leu Phe Asp Arg Tyr Pro Pro
225                 230                 235                 240
Asn Ser Lys Ala Lys Glu Phe Ala Glu Val Ala Glu Ser Arg Thr Ala
                245                 250                 255
Ser Asn Gly Ile Ala Asn Lys Ser Leu Lys Gly Thr Ile Ser Glu Lys
            260                 265                 270
Glu Ala Gln Cys Met Lys Phe Gln Val Trp Asp Tyr Val Pro Leu Val
        275                 280                 285
Glu Ile Tyr Ser Leu Pro Ala Phe Arg Leu Lys Tyr Asp Val Arg Phe
    290                 295                 300
Ser Lys Leu Glu Gln Met Thr Ser Gly Tyr Asp Lys Val Ile Leu Ile
305                 310                 315                 320
Glu Asn Gln Val Val Asn Asn Leu Asp Glu Ala Lys Val Ile Tyr Lys
                325                 330                 335
Lys Tyr Ile Asp Gln Gly Leu Glu Gly Ile Ile Leu Lys Asn Ile Asp
            340                 345                 350
Gly Leu Trp Glu Asn Ala Arg Ser Lys Asn Leu Tyr Lys Phe Lys Glu
        355                 360                 365
Val Ile Asp Val Asp Leu Lys Ile Val Gly Ile Tyr Pro His Arg Lys
    370                 375                 380
Asp Pro Thr Lys Ala Gly Gly Phe Ile Leu Glu Ser Glu Cys Gly Lys
385                 390                 395                 400
Ile Lys Val Asn Ala Gly Ser Gly Leu Lys Asp Lys Ala Gly Val Lys
                405                 410                 415
Ser His Glu Leu Asp Arg Thr Arg Ile Met Glu Asn Gln Asn Tyr Tyr
            420                 425                 430
Ile Gly Lys Ile Leu Glu Cys Lys Cys Asn Gly Trp Leu Lys Ser Ala
        435                 440                 445
Gly Arg Lys Asp Gly Leu Lys Leu Phe Leu Pro Ile Ala Ile Arg Leu
    450                 455                 460
Arg Glu Asp Lys Thr Lys Ala Asn Thr Phe Glu Asp Val Phe Gly Asp
465                 470                 475                 480
Phe His Glu Val Thr Gly Leu
                485

<210> SEQ ID NO 41
<211> LENGTH: 1464
<212> TYPE: DNA
<213> ORGANISM: Artificial Sequence
<220> FEATURE:
<223> OTHER INFORMATION: engineered ligase variant

<400> SEQUENCE: 41
atgattctta aaattctgaa cgaaattgca agcattggtt ccactaaaca aaaacaagcc     60
attctggaaa aaataaaga caatgaactg ttaaagcgcg tgtatcgcct gacctattcg    120
cgtggcctgc aatactatat taaaaaatgg cccaaaccgg cattgcgac gcagagcttc    180 ggcatgctta ccctgaccga tatgctggat tttatcgagt ttactcttgc gacgcgcaaa    240
cttaccggca acgctgctat tagagaattg acgggctata ttaccgatgg caaaaaagat    300
gatgttgagg tgctgcgtcg cgtcatgatg cgtgatctgg agtgcggtgc gtcagtgagc    360

```
atcgctaaca aagtgtggaa gggtttgatc ccggaacagc cacagatgct tgcaagcagc    420
tacgatgaaa agggcattaa caaaagaatc aaatttccgg ctttcgccca gctgaaagcg    480
gatggcgcgc gctgcttcgc cgaggtacgc ggtgacgaac tggacgacgt tcgtctgctg    540
tctcgcgctg gcaatgaata tctgggtctg gatctgctga agaagaact  gattaagatg    600 accgccgagg cgcgccaaat ccaccccgaa ggggtgctga ttgatggcga actggtgtat    660
cacgaacagg ttgcaaaaga gccggagggg ttggatgctc tgtttgataa ttacccggaa    720
aatagcaaag cgaaagaatt tgcggaagtg gcggaatccc gcaccgcaag caatggtatc    780
gcaaataaat cgctgaaggg caccatttct gagaaagaag cacagtgtat gaagttccag    840
gtgtgggact acgtgccact ggttgagatc tactccctgc cagcgtttcg cctgaaatac    900
gatgtgcgtt tttcaaaact ggaacagatg acgagcggat atgataaagt aattttaatc    960
gagaaccagg tcgtgaacaa cctggatgaa gcaaaagtta tctataaaaa atatattgat   1020
cagggcttag aaggcattat cctgaagaac attgatggcc tttgggaaaa tgcacgcagc   1080
aaaaacctgt ataaatttaa agaagtgatt gatgtagatc tgaagattgt tggtatttac   1140
ccgcatcgca aagacccgac caaagcaggt ggtttcatcc tggaatctga atgcggtaaa   1200
attaaagtga acgcaggcag tggttttgaaa gataaagctg tgttaaaag  tcacgaactg   1260 gatcgcacgc gcatcatgga aaccagaac  tattatatcg caaaattct  ggagtgcaaa   1320 tgcaacgggt ggcttaagag cgatgggcgc aaagactatc tgaaattgtt cctgccgatt   1380
gcgattcgcc ttcgcgaaga caaaactaag gcgaatactt tcgaagatgt gttcggtgat   1440
tttcatgaag tcacgggtct gtaa                                          1464
```

<210> SEQ ID NO 42
<211> LENGTH: 487
<212> TYPE: PRT
<213> ORGANISM: Artificial Sequence
<220> FEATURE:
<223> OTHER INFORMATION: engineered ligase variant

<400> SEQUENCE: 42

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Arg Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Lys Gly
        115                 120                 125

Leu Ile Pro Glu Gln Pro Gln Met Leu Ala Ser Ser Tyr Asp Glu Lys
    130                 135                 140

Gly Ile Asn Lys Arg Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
```

```
                    165                 170                 175
Val Arg Leu Leu Ser Arg Ala Gly Asn Glu Tyr Leu Gly Leu Asp Leu
                180                 185                 190

Leu Lys Glu Glu Leu Ile Lys Met Thr Ala Glu Ala Arg Gln Ile His
            195                 200                 205

Pro Glu Gly Val Leu Ile Asp Gly Glu Leu Val Tyr His Glu Gln Val
        210                 215                 220

Ala Lys Glu Pro Glu Gly Leu Asp Ala Leu Phe Asp Asn Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
                260                 265                 270

Glu Ala Gln Cys Met Lys Phe Gln Val Trp Asp Tyr Val Pro Leu Val
            275                 280                 285

Glu Ile Tyr Ser Leu Pro Ala Phe Arg Leu Lys Tyr Asp Val Arg Phe
        290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
                340                 345                 350

Gly Leu Trp Glu Asn Ala Arg Ser Lys Asn Leu Tyr Lys Phe Lys Glu
            355                 360                 365

Val Ile Asp Val Asp Leu Lys Ile Val Gly Ile Tyr Pro His Arg Lys
        370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
                420                 425                 430

Ile Gly Lys Ile Leu Glu Cys Lys Cys Asn Gly Trp Leu Lys Ser Asp
            435                 440                 445

Gly Arg Lys Asp Tyr Leu Lys Leu Phe Leu Pro Ile Ala Ile Arg Leu
        450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 43
<211> LENGTH: 1464
<212> TYPE: DNA
<213> ORGANISM: Artificial Sequence
<220> FEATURE:
<223> OTHER INFORMATION: engineered ligase variant

<400> SEQUENCE: 43
atgattctta aaattctgaa cgaaattgca agcattggtt ccactaaaca aaacaagcc       60 attctggaaa aaataaaga caatgaactg ttaaagcgcg tgtatcgcct gacctattcg      120
cgtggcctgc aatactatat taaaaaatgg cccaaaccgg gcattgcgac gcagagcttc    180
ggcatgctga ccctgaccga tatgctggat tttatcgagt ttactcttgc gacgcgcaaa    240
```

```
cttaccggca acgctcggat tagaaaattg acgggctata ttaccgatgg caaaaaagat    300
gatgttgagg tgctgcgtcg cgtcatgatg cgtgatctgg agtgcggtgc gtcagtgagc    360
atcgctaaca aagtgtggaa gggtttgatc ccggaacagc cacagatgct tgcaagcagc    420
tacgatgaaa agggcattaa caaaagaatc aaatttccgg ctttcgccca gctgaaagcg    480
gatggcgcgc gctgcttcgc cgaggtacgc ggtgacgaac tggacgacgt tcgtctgctg    540
tctcgcgctg gcaatgaata tctgggtctg gatctgctga agaagaact gattaagatg     600 accgccgagg cgcgccaaat ccaccccgaa ggggtgctga ttgatggcga actggtgtat    660
cacgaacagg ttgcaaaaga gccggagggg ttggatgctc tgtttgataa ttacccgcct    720
aatagcaaag cgaaagaatt tgcggaagtg gcggaatccc gcaccgcaag caatggtatc    780
gcaaataaat cgctgaaggg caccatttct gagaagaag cacagtgtat gaagttccag     840
gtgtgggact acgtgccact ggttgagatc tactccctgc cagcgtttcg cctgaaatac    900
gatgtgcgtt tttcaaaact ggaacagatg acgagcggat atgataaagt aattttaatc    960
gagaaccagg tcgtgaacaa cctggatgaa gcaaaagtta tctataaaaa atatattgat   1020
cagggcttag aaggcattat cctgaagaac attgatggcc tttgggaaaa tgcacgcagc   1080
aaaaacctgt ataaatttaa agaagtgatt gatgtagatc tgaagattgt tggtatttac   1140
ccgcatcgca aagacccgac caaagcaggt ggtttcatcc tggaatctga atgcggtaaa   1200
attaaagtga acgcaggcag tggtttgaaa gataaagctg gtgttaaaag tcacgaactg   1260
gatcgcacgc gcatcatgga aaaccagaac tattatatcg gcaaaattct ggagtgcaaa   1320
tgcaacgggt ggcttaagag cgatgggcgc aaagactatg ttaaattgtt cctgccgatt   1380
gcgattcgcc ttcgcgaaga caaaactaag gcgaatactt tcgaagatgt gttcggtgat   1440
tttcatgaag tcacgggtct gtaa                                          1464
```

<210> SEQ ID NO 44
<211> LENGTH: 487
<212> TYPE: PRT
<213> ORGANISM: Artificial Sequence
<220> FEATURE:
<223> OTHER INFORMATION: engineered ligase variant

<400> SEQUENCE: 44

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Arg Ile Arg Lys Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Lys Gly
        115                 120                 125

Leu Ile Pro Glu Gln Pro Gln Met Leu Ala Ser Ser Tyr Asp Glu Lys
    130                 135                 140

Gly Ile Asn Lys Arg Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
            165                 170                 175

Val Arg Leu Leu Ser Arg Ala Gly Asn Glu Tyr Leu Gly Leu Asp Leu
        180                 185                 190

Leu Lys Glu Glu Leu Ile Lys Met Thr Ala Glu Ala Arg Gln Ile His
    195                 200                 205

Pro Glu Gly Val Leu Ile Asp Gly Glu Leu Val Tyr His Glu Gln Val
210                 215                 220

Ala Lys Glu Pro Glu Gly Leu Asp Ala Leu Phe Asp Asn Tyr Pro Pro
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Asp Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Lys Cys Asn Gly Trp Leu Lys Ser Asp
        435                 440                 445

Gly Arg Lys Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 45
<211> LENGTH: 1464
<212> TYPE: DNA
<213> ORGANISM: Artificial Sequence
<220> FEATURE:
<223> OTHER INFORMATION: engineered ligase variant

<400> SEQUENCE: 45
atgattctta aaattctgaa cgaaattgca agcattggtt ccactaaaca aaaaaaagcc    60

```
attctggaaa aaataaaga caatgaactg ttaaagcgcg tgtatcgcct gacctattcg     120
cgtggcctgc aatactatat taaaaaatgg cccaaaccgg gcattgcgac gcagagcttc     180
ggcatgacta ccctgaccga tatgctggat tttatcgagt ttactcttgc gacgcgcaaa     240
cttaccggca acgctgctat tagagaattg acgggctata ttaccgatgg caaaaaagat     300
gatgttgagg tgctgcgtcg cgtcatgatg cgtgatctgg agtgcggtgc gtcagtgagc     360
atcgctaaca aagtgtggaa gggtttgatc ccggaacagc cacagatgct tgcaagcagc     420
tacgatgaaa agggcattaa caaaaacatc aaatttccgg ctttcgccca gctgaaagcg     480
gatggcgcgc gctgcttcgc cgaggtacgc ggtgacgaac tggacgacgt tcgtctgctg     540
tctcgcaaag gtaatgaata tctgggtctg gatctgctga agaagaact  gattaagatg     600 accgccgagg cgcgccaaat ccaccccgaa ggggtgctga ttgatggcga actggtgtat     660
cacgaacagg ttgcaaaaga gccggagggg aaagacgctc tgtttgatcg ataccccggaa    720 aatagcaaag cgaaagaatt tgcggaagtg gcggaatccc gcaccgcaag caatggtatc     780
gcaaataaat cgctgaaggg caccattcct gagaaagaag cacagtgtat gaagttccag     840
gtgtgggact acgtgccact ggttgagatc tactccctgc cagcgtttcg cctgaaatac     900
gatgtgcgtt tttcaaaact ggaacagatg acgagcggat atgataaagt aattttaatc     960
gagaaccagg tcgtgaacaa cctggatgaa gcaaaagtta tctataaaaa atatattgat    1020
cagggcttag aaggcattat cctgaagaac attgatggcc tttgggaaaa tgcacgcagc    1080
aaaaacctgt ataaatttaa agaagtgatt tgggtagatc tgaagattgt tggtatttac    1140
ccgcatcgca aagaccctac caaagcaggt ggtttcatcc tggaatctga atgcggtaaa    1200
attaaagtga acgcaggcag tggtttgaaa gataaagctg gtgttaaaag tcacgaactg    1260
gatcgcacgc gcatcatgcg gaaccagaac tattatatcg gcaaaattct ggaatgcaaa    1320
tgcaacgggt ggcttaagag cgatgggcgc aagccctatg tgaaattgtt cctgccgatt    1380
gcgattcgcc ttcgcggaga caaaactaag gcgaatactt tcgaagatgt gttcggtgat    1440
tttcatgaag tcacgggtct gtaa                                             1464
```

<210> SEQ ID NO 46  
<211> LENGTH: 487  
<212> TYPE: PRT  
<213> ORGANISM: Artificial Sequence  
<220> FEATURE:  
<223> OTHER INFORMATION: engineered ligase variant

<400> SEQUENCE: 46

```
Met Ile Leu Lys Ile Leu Asn Glu Ile Ala Ser Ile Gly Ser Thr Lys
1               5                   10                  15

Gln Lys Lys Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Thr Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Arg Glu Leu Thr Gly Tyr Ile Thr Asp
                85                  90                  95

Gly Lys Lys Asp Asp Val Glu Val Leu Arg Arg Val Met Met Arg Asp
            100                 105                 110
```

```
Leu Glu Cys Gly Ala Ser Val Ser Ile Ala Asn Lys Val Trp Lys Gly
            115                 120                 125
Leu Ile Pro Glu Gln Pro Gln Met Leu Ala Ser Ser Tyr Asp Glu Lys
        130                 135                 140
Gly Ile Asn Lys Asn Ile Lys Phe Pro Ala Phe Ala Gln Leu Lys Ala
145                 150                 155                 160
Asp Gly Ala Arg Cys Phe Ala Glu Val Arg Gly Asp Glu Leu Asp Asp
                165                 170                 175
Val Arg Leu Leu Ser Arg Lys Gly Asn Glu Tyr Leu Gly Leu Asp Leu
            180                 185                 190
Leu Lys Glu Glu Leu Ile Lys Met Thr Ala Glu Ala Arg Gln Ile His
        195                 200                 205
Pro Glu Gly Val Leu Ile Asp Gly Glu Leu Val Tyr His Glu Gln Val
210                 215                 220
Ala Lys Glu Pro Glu Gly Lys Asp Ala Leu Phe Asp Arg Tyr Pro Glu
225                 230                 235                 240
Asn Ser Lys Ala Lys Glu Phe Ala Glu Val Ala Glu Ser Arg Thr Ala
                245                 250                 255
Ser Asn Gly Ile Ala Asn Lys Ser Leu Lys Gly Thr Ile Ser Glu Lys
            260                 265                 270
Glu Ala Gln Cys Met Lys Phe Gln Val Trp Asp Tyr Val Pro Leu Val
        275                 280                 285
Glu Ile Tyr Ser Leu Pro Ala Phe Arg Leu Lys Tyr Asp Val Arg Phe
290                 295                 300
Ser Lys Leu Glu Gln Met Thr Ser Gly Tyr Asp Lys Val Ile Leu Ile
305                 310                 315                 320
Glu Asn Gln Val Val Asn Asn Leu Asp Glu Ala Lys Val Ile Tyr Lys
                325                 330                 335
Lys Tyr Ile Asp Gln Gly Leu Glu Gly Ile Ile Leu Lys Asn Ile Asp
            340                 345                 350
Gly Leu Trp Glu Asn Ala Arg Ser Lys Asn Leu Tyr Lys Phe Lys Glu
        355                 360                 365
Val Ile Trp Val Asp Leu Lys Ile Val Gly Ile Tyr Pro His Arg Lys
370                 375                 380
Asp Pro Thr Lys Ala Gly Gly Phe Ile Leu Glu Ser Glu Cys Gly Lys
385                 390                 395                 400
Ile Lys Val Asn Ala Gly Ser Gly Leu Lys Asp Lys Ala Gly Val Lys
                405                 410                 415
Ser His Glu Leu Asp Arg Thr Arg Ile Met Arg Asn Gln Asn Tyr Tyr
            420                 425                 430
Ile Gly Lys Ile Leu Glu Cys Lys Cys Asn Gly Trp Leu Lys Ser Asp
        435                 440                 445
Gly Arg Lys Pro Tyr Val Lys Leu Phe Leu Pro Ile Ala Ile Arg Leu
450                 455                 460
Arg Gly Asp Lys Thr Lys Ala Asn Thr Phe Glu Asp Val Phe Gly Asp
465                 470                 475                 480
Phe His Glu Val Thr Gly Leu
                485

<210> SEQ ID NO 47
<211> LENGTH: 1464
<212> TYPE: DNA
<213> ORGANISM: Artificial Sequence
<220> FEATURE:
<223> OTHER INFORMATION: engineered ligase variant
```

<400> SEQUENCE: 47

```
atgattctta aaattctgaa cgaaattgca agcattggtt ccactaaaca aaaaaaagcc      60
attctggaaa aaataaaga caatgaactg ttaaagcgcg tgtatcgcct gacctattcg     120
cgtggcctgc aatactatat taaaaaatgg cccaaaccgg gcattgcgac gcagagcttc     180
ggcatgacta ccctgaccga tatgctggat tttatcgagt ttactcttgc gacgcgcaaa     240
cttaccggca acgctgctat tagagaattg acgggctata ttaccgatgg caaaaaagat     300
gatgttgagg tgctgcgtcg cgtcatgatg cgtgatctgg agtgcggtgc gtcagtgagc     360
atcgctaaca aagtgtggaa gggttttgatc ccggaacagc cacagatgct tgcaagcagc     420
tacgatgaaa agggcattaa caaaaatatc aaatttccgg ctttcgccca gctgaaagcg     480
gatggcgcgc gctgcttcgc cgaggtacgc ggtgacgaac tggacgacgt tcgtctgctg     540
tctcgcgctg gcaatgaata tctgggtctg gatctgctga agaagaact gattaagatg      600
accgccgagg cgcgccaaat ccaccccgaa gggtgctga ttgatggcga actggtgtat      660
cacgaacagg ttgcaaaaga gccggagggg ttggatgctc tgtttgatcg ataccccggaa    720
aatagcaaag cgaaagaatt tgcggaagtg gcggaatccc gcaccgcaag caatggtatc     780
gcaaataaat cgctgaaggg caccatttct gagaaagaag cacagtgtat gaagttccag     840
gtgtgggact acgtgccact ggttgagatc tactccctgc cagcgtttcg cctgaaatac     900
gatgtgcgtt tttcaaaact ggaacagatg acgagcggat atgataaagt aattttaatc     960
gagaaccagg tcgtgaacaa cctggatgaa gcaaaagtta tctataaaaa atatattgat    1020
cagggcttag aaggcattat cctgaagaac attgatggcc tttgggaaaa tgcacgcagc    1080
aaaaacctgt ataaatttaa agaagtgatt tgggtagatc tgaagattgt tggtattac      1140
ccgcatcgca aaaaacctac caagcaggt ggtttcatcc tggaatctga atgcggtaaa     1200
attaaagtga acgcaggcag tggtttgaaa gataaagcag tgttaaaag tcacgaactg    1260
gatcgcacgc gcatcatgga gaaccagaac tattatatcg gcaaaattct ggaatgcaaa    1320
tgcaacgggt ggcttaagag cgatgggcgc aagccccgtg tgaaattgtt cctgccgatt    1380
gcgattcgcc ttcgcggaga caaaactaag gcgaatactt tcgaagatgt gttcggtgat    1440
tttcatgaag tcacgggtct gtaa                                          1464
```

<210> SEQ ID NO 48
<211> LENGTH: 486
<212> TYPE: PRT
<213> ORGANISM: Artificial Sequence
<220> FEATURE:
<223> OTHER INFORMATION: engineered ligase variant

<400> SEQUENCE: 48

```
Met Ile Leu Lys Ile Leu Asn Glu Ile Ala Ser Ile Gly Ser Thr Lys
1               5                   10                  15

Gln Lys Lys Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Thr Leu
    50                  55                  60

Thr Asp Met Leu Asp Phe Ile Glu Phe Thr Leu Ala Thr Arg Lys Leu
65                  70                  75                  80

Thr Gly Asn Ala Ala Ile Arg Glu Leu Thr Gly Tyr Ile Thr Asp Gly
```

```
                85                  90                  95
Lys Lys Asp Asp Val Glu Val Leu Arg Arg Val Met Met Arg Asp Leu
            100                 105                 110

Glu Cys Gly Ala Ser Val Ser Ile Ala Asn Lys Val Trp Lys Gly Leu
        115                 120                 125

Ile Pro Glu Gln Pro Gln Met Leu Ala Ser Ser Tyr Asp Glu Lys Gly
    130                 135                 140

Ile Asn Lys Asn Ile Lys Phe Pro Ala Phe Ala Gln Leu Lys Ala Asp
145                 150                 155                 160

Gly Ala Arg Cys Phe Ala Glu Val Arg Gly Asp Glu Leu Asp Asp Val
                165                 170                 175

Arg Leu Leu Ser Arg Ala Gly Asn Glu Tyr Leu Gly Leu Asp Leu Leu
            180                 185                 190

Lys Glu Glu Leu Ile Lys Met Thr Ala Glu Ala Arg Gln Ile His Pro
        195                 200                 205

Glu Gly Val Leu Ile Asp Gly Glu Leu Val Tyr His Glu Gln Val Ala
    210                 215                 220

Lys Glu Pro Glu Gly Leu Asp Ala Leu Phe Asp Arg Tyr Pro Glu Asn
225                 230                 235                 240

Ser Lys Ala Lys Glu Phe Ala Glu Val Ala Glu Ser Arg Thr Ala Ser
                245                 250                 255

Asn Gly Ile Ala Asn Lys Ser Leu Lys Gly Thr Ile Ser Glu Lys Glu
            260                 265                 270

Ala Gln Cys Met Lys Phe Gln Val Trp Asp Tyr Val Pro Leu Val Glu
        275                 280                 285

Ile Tyr Ser Leu Pro Ala Phe Arg Leu Lys Tyr Asp Val Arg Phe Ser
    290                 295                 300

Lys Leu Glu Gln Met Thr Ser Gly Tyr Asp Lys Val Ile Leu Ile Glu
305                 310                 315                 320

Asn Gln Val Val Asn Asn Leu Asp Glu Ala Lys Val Ile Tyr Lys Lys
                325                 330                 335

Tyr Ile Asp Gln Gly Leu Glu Gly Ile Ile Leu Lys Asn Ile Asp Gly
            340                 345                 350

Leu Trp Glu Asn Ala Arg Ser Lys Asn Leu Tyr Lys Phe Lys Glu Val
        355                 360                 365

Ile Trp Val Asp Leu Lys Ile Val Gly Ile Tyr Pro His Arg Lys Lys
    370                 375                 380

Pro Thr Lys Ala Gly Gly Phe Ile Leu Glu Ser Glu Cys Gly Lys Ile
385                 390                 395                 400

Lys Val Asn Ala Gly Ser Gly Leu Lys Asp Lys Ala Gly Val Lys Ser
                405                 410                 415

His Glu Leu Asp Arg Thr Arg Ile Met Glu Asn Gln Asn Tyr Tyr Ile
            420                 425                 430

Gly Lys Ile Leu Glu Cys Lys Cys Asn Gly Trp Leu Lys Ser Asp Gly
        435                 440                 445

Arg Lys Pro Arg Val Lys Leu Phe Leu Pro Ile Ala Ile Arg Leu Arg
    450                 455                 460

Gly Asp Lys Thr Lys Ala Asn Thr Phe Glu Asp Val Phe Gly Asp Phe
465                 470                 475                 480

His Glu Val Thr Gly Leu
                485

<210> SEQ ID NO 49
```

<211> LENGTH: 1464
<212> TYPE: DNA
<213> ORGANISM: Artificial Sequence
<220> FEATURE:
<223> OTHER INFORMATION: engineered ligase variant

<400> SEQUENCE: 49

```
atgattctta aaattctgaa cgaaattgca agcattaagt ccactaaaca aaaaaagcc      60
attctggaaa aaataaaga caatgaactg ttaaagcgcg tgtatcgcct gacctattcg     120
cgtggcctgc aatactatat taaaaaatgg cccaaaccgg gcattgcgac gcagagcttc     180
ggcatgacta ccctgaccga tatgctggat tttatcgagt ttactcttgc gacgcgcaaa     240
cttaccggca acgctgctat tagagaattg acgggctata ttaccgatgg caaaaaagat     300
gatgttgagg tgctgcgtcg cgtcatgatg cgtgatctgg agtgcggtgc gtcagtgagc     360
atcgctaaca aagtgtggaa gggtttgatc ccggaacagc cacagatgct tgcaagcagc     420
tacgatgaaa agggcattaa caaaaacatc aaatttccgg ctttcgccca gctgaaagcg     480
gatggcgcgc gctgcttcgc cgaggtacgc ggtgacgaac tggacgacgt tcgtctgctg     540
tctcgcaaag gtaatgaata tctgggtctg atctgctga agaagaact gattaagatg     600
accgccgagg cgcgccaaat ccaccccgaa ggggtgctga ttgatggcga actggtgtat     660
cacgaacagg ttgcaaaaga gccggagggg ttaaaagctc tgtttgatcg atacccggaa     720
aatagcaaag cgaaagaatt tgcggaagtg gcggaatccc gcaccgcaag caatggtatc     780
gcaaataaat cgctgaaggg caccatttct gagaagaag cacagtgtat gaagttccag     840
gtgtgggact acgtgccact ggttgagatc tactccctgc cagcgtttcg cctgaaatac     900
gatgtgcgtt tttcaaaact ggaacagatg acgagcggat atgataaagt aatttttaatc     960
gagaaccagg tcgtgaacaa cctggatgaa gcaaagtta tctataaaaa atatattgat   1020
cagggcttag aaggcattat cctgaagaac attgatggcc tttgggaaaa tgcacgcagc   1080
aaaaacctgt ataaatttaa agaagtgatt tgggtagatc tgaagattgt tggtatttac   1140
ccgcatcgca agacaaaac caaagcaggt ggtttcatcc tggaatctga atgcggtaaa   1200
attaaagtga acgcaggcag tggtttgaaa gataaagctg tgttaaaag tcacgaactg   1260
gatcgcacgc gcatcatgga gaaccagaac tattatatcg gcaaaattct ggaatgcaaa   1320
tgcaacgggt ggcttaagag cgatgggcgc ggtccctatg tgaaattgtt cctgccgatt   1380
gcgattcgcc ttcgcgaaga caaaactaag gcgaatactt cgaagatgt gttcggtgat   1440
tttcatgaag tcacgggtct gtaa                                         1464
```

<210> SEQ ID NO 50
<211> LENGTH: 487
<212> TYPE: PRT
<213> ORGANISM: Artificial Sequence
<220> FEATURE:
<223> OTHER INFORMATION: engineered ligase variant

<400> SEQUENCE: 50

```
Met Ile Leu Lys Ile Leu Asn Glu Ile Ala Ser Ile Lys Ser Thr Lys
1               5                   10                  15

Gln Lys Lys Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Thr Thr
    50                  55                  60
```

```
Leu Thr Asp Met Leu Asp Phe Ile Glu Phe Thr Leu Ala Thr Arg Lys
 65                  70                  75                  80

Leu Thr Gly Asn Ala Ala Ile Arg Glu Leu Thr Gly Tyr Ile Thr Asp
                 85                  90                  95

Gly Lys Lys Asp Asp Val Glu Val Leu Arg Arg Val Met Met Arg Asp
                100                 105                 110

Leu Glu Cys Gly Ala Ser Val Ser Ile Ala Asn Lys Val Trp Lys Gly
                115                 120                 125

Leu Ile Pro Glu Gln Pro Gln Met Leu Ala Ser Ser Tyr Asp Glu Lys
130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Lys Gly Asn Glu Tyr Leu Gly Leu Asp Leu
                180                 185                 190

Leu Lys Glu Glu Leu Ile Lys Met Thr Ala Glu Ala Arg Gln Ile His
                195                 200                 205

Pro Glu Gly Val Leu Ile Asp Gly Glu Leu Val Tyr His Glu Gln Val
210                 215                 220

Ala Lys Glu Pro Glu Gly Leu Lys Ala Leu Phe Asp Arg Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
                260                 265                 270

Glu Ala Gln Cys Met Lys Phe Gln Val Trp Asp Tyr Val Pro Leu Val
                275                 280                 285

Glu Ile Tyr Ser Leu Pro Ala Phe Arg Leu Lys Tyr Asp Val Arg Phe
                290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
                340                 345                 350

Gly Leu Trp Glu Asn Ala Arg Ser Lys Asn Leu Tyr Lys Phe Lys Glu
                355                 360                 365

Val Ile Trp Val Asp Leu Lys Ile Val Gly Ile Tyr Pro His Arg Lys
                370                 375                 380

Asp Lys Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
                420                 425                 430

Ile Gly Lys Ile Leu Glu Cys Lys Cys Asn Gly Trp Leu Lys Ser Asp
                435                 440                 445

Gly Arg Gly Pro Tyr Val Lys Leu Phe Leu Pro Ile Ala Ile Arg Leu
                450                 455                 460

Arg Glu Asp Lys Thr Lys Ala Asn Thr Phe Glu Asp Val Phe Gly Asp
465                 470                 475                 480
```

Phe His Glu Val Thr Gly Leu
            485

<210> SEQ ID NO 51
<211> LENGTH: 1464
<212> TYPE: DNA
<213> ORGANISM: Artificial Sequence
<220> FEATURE:
<223> OTHER INFORMATION: engineered ligase variant

<400> SEQUENCE: 51

| | | | | | |
|---|---|---|---|---|---|
| atgattctta | aaattctgaa | cgaaattgca | agcattggtt | ccactaaaca | aaaaaaagcc | 60 |
| attctggaaa | aaaataaaga | caatgaactg | ttaaagcgcg | tgtatcgcct | gacctattcg | 120 |
| cgtggcctgc | aatactatat | taaaaaatgg | cccaaaccgg | gcattgcgac | gcagagcttc | 180 |
| ggcatgacta | ccctgaccga | tatgctggat | tttatcgagt | ttactcttgc | gacgcgcaaa | 240 |
| cttaccggca | acgctgctat | tagagaattg | acgggctata | ttaccgatgg | caaaaaagat | 300 |
| gatgttgagg | tgctgcgtcg | cgtcatgatg | cgtgatctgg | agtgcggtgc | gtcagtgagc | 360 |
| atcgctaaca | aagtgtggaa | gggtttgatc | ccggaacagc | cacagatgct | tgcaagcagc | 420 |
| tacgatgaaa | agggcattaa | caaaaatatc | aaatttccgg | ctttcgccca | gctgaaagcg | 480 |
| gatggcgcgc | gctgcttcgc | cgaggtacgc | ggtgacgaac | tggacgacgt | tcgtctgctg | 540 |
| tctcgcaaag | gtaatgaata | tctgggtctg | gatctgctga | agaagaact | gattaagatg | 600 |
| accgccgagg | cgcgccaaat | ccaccccgaa | ggggtgctga | ttgatggcga | actggtgtat | 660 |
| cacgaacagg | ttgcaaaaga | gccggagggg | ttggatgctc | tgtttgatcg | atacccggaa | 720 |
| aatagcaaag | cgaaagaatt | tgcggaagtg | gcggaatccc | gcaccgcaag | caatggtatc | 780 |
| gcaaataaat | cgctgaaggg | caccatttct | gagaaagaag | cacagtgtat | gaagttccag | 840 |
| gtgtgggact | acgtgccact | ggttgagatc | tactccctgc | cagcgtttcg | cctgaaatac | 900 |
| gatgtgcgtt | tttcaaaact | ggaacagatg | acgagcggat | atgataaagt | aattttaatc | 960 |
| gagaaccagg | tcgtgaacaa | cctggatgaa | gcaaaagtta | tctataaaaa | atatattgat | 1020 |
| cagggcttag | aaggcattat | cctgaagaac | attgatggcc | tttgggaaaa | tgcacgcagc | 1080 |
| aaaaacctgt | ataaatttaa | agaagtgatt | tgggtagctc | tgaagattgt | tggtatttac | 1140 |
| ccgcatcgca | aagacaaaac | caaagcaggt | ggtttcatcc | tggaatctga | atgcggtaaa | 1200 |
| attaaagtga | acgcaggcag | tggtttgaaa | gataaagcag | tgttaaaag | tcacgaactg | 1260 |
| gatcgcacgc | gcatcatgga | gaaccagaac | tattatatcg | gcaaaattct | ggaatgcaaa | 1320 |
| tgcaacgggt | ggcttaagag | cgatgggcgc | aaaccctatg | tgaaattgtt | cctgccgatt | 1380 |
| gcgattcgcc | ttcgcgaaga | caaaactaag | gcgaatactt | tcgaagatgt | gttcggtgat | 1440 |
| tttcatgaag | tcacgggtct | gtaa | | | | 1464 |

<210> SEQ ID NO 52
<211> LENGTH: 487
<212> TYPE: PRT
<213> ORGANISM: Artificial Sequence
<220> FEATURE:
<223> OTHER INFORMATION: engineered ligase variant

<400> SEQUENCE: 52

Met Ile Leu Lys Ile Leu Asn Glu Ile Ala Ser Ile Gly Ser Thr Lys
1               5                   10                  15

Gln Lys Lys Ala Ile Leu Glu Lys Asn Lys Asp Asn Glu Leu Leu Lys
            20                  25                  30

-continued

```
Arg Val Tyr Arg Leu Thr Tyr Ser Arg Gly Leu Gln Tyr Ile Lys
             35                  40                  45

Lys Trp Pro Lys Pro Gly Ile Ala Thr Gln Ser Phe Gly Met Thr Thr
 50                  55                  60

Leu Thr Asp Met Leu Asp Phe Ile Glu Phe Thr Leu Ala Thr Arg Lys
 65                  70                  75                  80

Leu Thr Gly Asn Ala Ala Ile Arg Glu Leu Thr Gly Tyr Ile Thr Asp
                 85                  90                  95

Gly Lys Lys Asp Asp Val Glu Val Leu Arg Arg Val Met Met Arg Asp
                100                 105                 110

Leu Glu Cys Gly Ala Ser Val Ser Ile Ala Asn Lys Val Trp Lys Gly
            115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Lys Gly Asn Glu Tyr Leu Gly Leu Asp Leu
                180                 185                 190

Leu Lys Glu Glu Leu Ile Lys Met Thr Ala Glu Ala Arg Gln Ile His
    195                 200                 205

Pro Glu Gly Val Leu Ile Asp Gly Glu Leu Val Tyr His Glu Gln Val
    210                 215                 220

Ala Lys Glu Pro Glu Gly Leu Asp Ala Leu Phe Asp Arg Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
                260                 265                 270

Glu Ala Gln Cys Met Lys Phe Gln Val Trp Asp Tyr Val Pro Leu Val
            275                 280                 285

Glu Ile Tyr Ser Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
    355                 360                 365

Val Ile Trp Val Ala Leu Lys Ile Val Gly Ile Tyr Pro His Arg Lys
    370                 375                 380

Asp Lys Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
                420                 425                 430

Ile Gly Lys Ile Leu Glu Cys Lys Cys Asn Gly Trp Leu Lys Ser Asp
            435                 440                 445

Gly Arg Lys Pro Tyr Val Lys Leu Phe Leu Pro Ile Ala Ile Arg Leu
```

```
                450            455            460
Arg Glu Asp Lys Thr Lys Ala Asn Thr Phe Glu Asp Val Phe Gly Asp
465                 470                475                 480

Phe His Glu Val Thr Gly Leu
                485

<210> SEQ ID NO 53
<211> LENGTH: 1464
<212> TYPE: DNA
<213> ORGANISM: Artificial Sequence
<220> FEATURE:
<223> OTHER INFORMATION: engineered ligase variant

<400> SEQUENCE: 53
atgattctta aaattctgaa cgaaattgca agcattaagt ccactaaaca aaaaaaagcc      60
attctggaaa aaaataaaga caatgaactg ttaaagcgcg tgtatcgcct gacctattcg     120
cgtggcctgc aatactatat taaaaaatgg cccaaaccgg gcattgcgac gcagagcttc     180
ggcatgacta ccctgaccga tatgctggat tttatcgagt ttactcttgc gacgcgcaaa     240
cttaccggca acgctgctat tagagaattg acgggctata ttaccgatgg caaaaaagat     300
gatgttgagg tgctgcgtcg cgtcatgatg cgtgatctgg agtgcggtgc gtcagtgagc     360
atcgctaaca aagtgtggaa gggttttgat ccggaacagc cacagatgct tgcaagcagc     420
tacgatgaaa agggcattaa caaaaacatc aaatttccgg ctttcgccca gctgaaagcg     480
gatggcgcgc gctgcttcgc cgaggtacgc ggtgacgaac tggacgacgt tcgtctgctg     540
tctcgcaaag gtaatgaata tctgggtctg gatctgctga agaagaact gattaagatg     600
accgccgagg cgcgccaaat ccaccccgaa ggggtgctga ttgatggcga actggtgtat     660
cacgaacagg ttgcaaaaga gccggagggg ttaaaagctc tgtttgatcg ataccccggaa    720
aatagcaaag cgaaagaatt tgcggaagtg gcggaatccc gcaccgcaag caatggtatc     780
gcaaataaat cgctgaaggg caccatttct gagaaagaag cacagtgtat gaagttccag     840
gtgtgggact acgtgccact ggttgagatc tactccctgc cagcgtttcg cctgaaatac     900
gatgtgcgtt tttcaaaact ggaacagatg acgagcggat atgataaagt aatttttaatc    960
gagaaccagg tcgtgaacaa cctgctggaa gcaaaagtta tctataaaa atatattgat     1020
cagggcttag aaggcattat cctgaagaac attgatggcc tttgggaaaa tgcacgcagc    1080
aaaaacctgt ataaatttaa agaagtgatt tgggtagatc tgaagattgt tggtatttac    1140
ccgcatcgca aagaccctac caaagcaggt ggtttcatcc tggaatctga atgcggtaaa    1200
attaaagtga acgcaggcag tggtttgaaa gataaagcag gtgttaaaag tcacgaactg    1260
gatcgcacgc gcatcatgga gaaccagaac tattatatcg gcaaaattct ggaatgcaaa    1320
tgcaacgggt ggcttaagag cgatgggcgc aagcccggtg tgaaattgtt cctgccgatt    1380
gcgattcgcc ttcgcggaga caaaactaag gcgaatactt tcgaagatgt gttcggtgat    1440
tttcatgaag tcacgggtct gtaa                                           1464

<210> SEQ ID NO 54
<211> LENGTH: 487
<212> TYPE: PRT
<213> ORGANISM: Artificial Sequence
<220> FEATURE:
<223> OTHER INFORMATION: engineered ligase variant

<400> SEQUENCE: 54

Met Ile Leu Lys Ile Leu Asn Glu Ile Ala Ser Ile Lys Ser Thr Lys
```

-continued

```
1               5                   10                  15
Gln Lys Lys Ala Ile Leu Glu Lys Asn Lys Asp Asn Glu Leu Leu Lys
             20                  25                  30
Arg Val Tyr Arg Leu Thr Tyr Ser Arg Gly Leu Gln Tyr Tyr Ile Lys
             35                  40                  45
Lys Trp Pro Lys Pro Gly Ile Ala Thr Gln Ser Phe Gly Met Thr Thr
             50                  55                  60
Leu Thr Asp Met Leu Asp Phe Ile Glu Phe Thr Leu Ala Thr Arg Lys
 65                  70                  75                  80
Leu Thr Gly Asn Ala Ala Ile Arg Glu Leu Thr Gly Tyr Ile Thr Asp
             85                  90                  95
Gly Lys Lys Asp Asp Val Glu Val Leu Arg Arg Val Met Met Arg Asp
             100                 105                 110
Leu Glu Cys Gly Ala Ser Val Ser Ile Ala Asn Lys Val Trp Lys Gly
             115                 120                 125
Leu Ile Pro Glu Gln Pro Gln Met Leu Ala Ser Tyr Asp Glu Lys
             130                 135                 140
Gly Ile Asn Lys Asn Ile Lys Phe Pro Ala Phe Ala Gln Leu Lys Ala
145                 150                 155                 160
Asp Gly Ala Arg Cys Phe Ala Glu Val Arg Gly Asp Glu Leu Asp Asp
             165                 170                 175
Val Arg Leu Leu Ser Arg Lys Gly Asn Glu Tyr Leu Gly Leu Asp Leu
             180                 185                 190
Leu Lys Glu Glu Leu Ile Lys Met Thr Ala Glu Ala Arg Gln Ile His
             195                 200                 205
Pro Glu Gly Val Leu Ile Asp Gly Glu Leu Val Tyr His Glu Gln Val
             210                 215                 220
Ala Lys Glu Pro Glu Gly Leu Lys Ala Leu Phe Asp Arg Tyr Pro Glu
225                 230                 235                 240
Asn Ser Lys Ala Lys Glu Phe Ala Glu Val Ala Glu Ser Arg Thr Ala
             245                 250                 255
Ser Asn Gly Ile Ala Asn Lys Ser Leu Lys Gly Thr Ile Ser Glu Lys
             260                 265                 270
Glu Ala Gln Cys Met Lys Phe Gln Val Trp Asp Tyr Val Pro Leu Val
             275                 280                 285
Glu Ile Tyr Ser Leu Pro Ala Phe Arg Leu Lys Tyr Asp Val Arg Phe
             290                 295                 300
Ser Lys Leu Glu Gln Met Thr Ser Gly Tyr Asp Lys Val Ile Leu Ile
305                 310                 315                 320
Glu Asn Gln Val Val Asn Asn Leu Leu Glu Ala Lys Val Ile Tyr Lys
             325                 330                 335
Lys Tyr Ile Asp Gln Gly Leu Glu Gly Ile Ile Leu Lys Asn Ile Asp
             340                 345                 350
Gly Leu Trp Glu Asn Ala Arg Ser Lys Asn Leu Tyr Lys Phe Lys Glu
             355                 360                 365
Val Ile Trp Val Asp Leu Lys Ile Val Gly Ile Tyr Pro His Arg Lys
             370                 375                 380
Asp Pro Thr Lys Ala Gly Gly Phe Ile Leu Glu Ser Glu Cys Gly Lys
385                 390                 395                 400
Ile Lys Val Asn Ala Gly Ser Gly Leu Lys Asp Lys Ala Gly Val Lys
             405                 410                 415
Ser His Glu Leu Asp Arg Thr Arg Ile Met Glu Asn Gln Asn Tyr Tyr
             420                 425                 430
```

-continued

```
Ile Gly Lys Ile Leu Glu Cys Lys Cys Asn Gly Trp Leu Lys Ser Asp
        435                 440                 445

Gly Arg Lys Pro Gly Val Lys Leu Phe Leu Pro Ile Ala Ile Arg Leu
    450                 455                 460

Arg Gly Asp Lys Thr Lys Ala Asn Thr Phe Glu Asp Val Phe Gly Asp
465                 470                 475                 480

Phe His Glu Val Thr Gly Leu
                485
```